US011744822B2

(12) United States Patent
Charo et al.

(10) Patent No.: US 11,744,822 B2
(45) Date of Patent: Sep. 5, 2023

(54) REDUCING TUMOR BURDEN BY ADMINISTERING CCR1 ANTAGONISTS IN COMBINATION WITH PD-1 INHIBITORS OR PD-L1 INHIBITORS

(71) Applicant: CHEMOCENTRYX, INC., Mountain View, CA (US)

(72) Inventors: Israel Charo, Mountain View, CA (US); Heiyoun Jung, Menlo Park, CA (US); Thomas J. Schall, Menlo Park, CA (US); Penglie Zhang, Foster City, CA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 617 days.

(21) Appl. No.: 16/742,139

(22) Filed: Jan. 14, 2020

(65) Prior Publication Data

US 2020/0289472 A1 Sep. 17, 2020

Related U.S. Application Data

(62) Division of application No. 15/480,992, filed on Apr. 6, 2017, now Pat. No. 10,568,870.

(60) Provisional application No. 62/319,689, filed on Apr. 7, 2016.

(51) Int. Cl.

| | |
|---|---|
| *A61K 39/00* | (2006.01) |
| *A61K 31/4192* | (2006.01) |
| *C07K 16/28* | (2006.01) |
| *A61P 35/00* | (2006.01) |
| *A61K 45/06* | (2006.01) |
| *A61K 9/00* | (2006.01) |
| *A61K 31/4178* | (2006.01) |
| *A61K 31/496* | (2006.01) |
| *A61K 39/395* | (2006.01) |
| *C07K 16/30* | (2006.01) |

(52) U.S. Cl.

CPC ........ *A61K 31/4192* (2013.01); *A61K 9/0053* (2013.01); *A61K 31/4178* (2013.01); *A61K 31/496* (2013.01); *A61K 39/39558* (2013.01); *A61K 45/06* (2013.01); *A61P 35/00* (2018.01); *C07K 16/2827* (2013.01); *C07K 16/3015* (2013.01); *A61K 2039/505* (2013.01); *A61K 2039/54* (2013.01); *C07K 2317/76* (2013.01)

(58) Field of Classification Search

CPC ........ A61K 39/39558; A61K 2039/505; A61K 2300/00; A61P 35/00; C07K 16/2827

See application file for complete search history.

(56) References Cited

U.S. PATENT DOCUMENTS

| | | | |
|---|---|---|---|
| 5,817,677 | A | 10/1998 | Linz et al. |
| 7,524,845 | B2 | 4/2009 | Zhang et al. |
| 7,576,106 | B2 | 8/2009 | Zhang et al. |
| 7,629,344 | B2 | 12/2009 | Li et al. |
| 7,842,693 | B2 | 11/2010 | Pennell et al. |
| 7,888,354 | B2 | 2/2011 | Nakamura et al. |
| 8,168,757 | B2 | 5/2012 | Finnefrock et al. |
| 8,343,975 | B2 | 1/2013 | Zhang et al. |
| 8,354,509 | B2 | 1/2013 | Carven et al. |
| 8,552,154 | B2 | 10/2013 | Freeman et al. |
| 8,741,295 | B2 | 6/2014 | Olive |
| 8,907,053 | B2 | 12/2014 | Sasikumar et al. |
| 9,044,442 | B2 | 6/2015 | Sasikumar et al. |
| 9,096,642 | B2 | 8/2015 | Sasikumar et al. |
| 9,169,248 | B2 | 10/2015 | Chen et al. |
| 9,212,224 | B2 | 12/2015 | Cogswell et al. |
| 9,233,940 | B2 | 1/2016 | Sasikumar et al. |
| 9,328,116 | B2 | 5/2016 | Chen et al. |
| 9,750,722 | B2 | 9/2017 | Chen et al. |
| 10,568,870 | B2 | 2/2020 | Charo et al. |
| 2004/0192750 | A1 | 9/2004 | Sanner et al. |
| 2006/0276428 | A1 | 12/2006 | Elzein et al. |
| 2007/0088036 | A1 | 4/2007 | Zhang et al. |
| 2007/0093467 | A1 | 4/2007 | Zhang et al. |
| 2008/0004278 | A1 | 1/2008 | Dyckman et al. |
| 2008/0058341 | A1 | 3/2008 | Zhang et al. |
| 2008/0269280 | A1 | 10/2008 | Zhang et al. |
| 2008/0300257 | A1 | 12/2008 | Li et al. |
| 2009/0143377 | A1 | 6/2009 | Ng et al. |
| 2009/0252779 | A1 | 10/2009 | Zhang et al. |
| 2010/0069396 | A1 | 3/2010 | Zhang et al. |
| 2010/0113776 | A1 | 5/2010 | Nakamura et al. |

(Continued)

FOREIGN PATENT DOCUMENTS

| | | | |
|---|---|---|---|
| DE | 19539091 | A1 | 4/1997 |
| EP | 1 319 657 | A1 | 6/2003 |
| EP | 2 221 298 | A1 | 8/2010 |
| JP | 2007-513969 | A | 5/2007 |
| JP | 2008-546749 | A | 12/2008 |
| JP | 2010-528038 | A | 8/2010 |
| JP | 2012-502107 | A | 1/2012 |
| WO | 02/10141 | A1 | 2/2002 |
| WO | 2005/056015 | A1 | 6/2005 |

(Continued)

OTHER PUBLICATIONS

Gilchrist et al, Frontiers in Endocrinology vol. 13 16 pages (Mar. 2, 2022) (Year: 2022).*

(Continued)

*Primary Examiner* — Sheela J. Huff

(74) *Attorney, Agent, or Firm* — Mintz Levin Cohn Ferris Glovsky and Popeo PC

(57) ABSTRACT

The present invention provides methods for reducing tumor burden, tumor growth, tumor progression, and/or metastasis in a subject suffering from a solid tumor cancer such as triple negative breast cancer. The methods include administering to a subject in need thereof a therapeutically effective amount of a PD-L1 inhibitor or a PD-1 inhibitor in combination with a small molecule chemokine receptor antagonist that blocks CCR1.

10 Claims, 10 Drawing Sheets

(56) References Cited

U.S. PATENT DOCUMENTS

2010/0173911 A1 7/2010 Li et al.
2010/0240618 A1 9/2010 Pennell et al.
2011/0098308 A1 4/2011 Zhang et al.
2011/0230521 A1 9/2011 Cook et al.
2012/0010214 A1 1/2012 Li et al.
2012/0108614 A1 5/2012 Chong
2014/0099254 A1 4/2014 Chang
2014/0171420 A1 6/2014 Chen et al.
2014/0179733 A1 6/2014 Chen et al.
2014/0294898 A1 10/2014 Miller et al.
2014/0341917 A1 11/2014 Nastri et al.
2015/0073024 A1 3/2015 Sasikumar et al.
2015/0125463 A1 5/2015 Cogswell et al.
2015/0203580 A1 7/2015 Papadopoulos et al.
2015/0216970 A1* 8/2015 Grogan .............. C07K 16/3015 530/389.7
2015/0291549 A1 10/2015 Chupak et al.
2015/0320859 A1 11/2015 Maecker et al.
2015/0344544 A1* 12/2015 Wong ...................... A61P 19/02 530/387.3
2016/0194295 A1 7/2016 Sasikumar et al.
2016/0194307 A1 7/2016 Chupak et al.
2016/0222060 A1 8/2016 Miller et al.
2016/0303084 A1 10/2016 Chen et al.
2018/0071257 A1 3/2018 Chen et al.
2021/0093613 A1 4/2021 Chen et al.

FOREIGN PATENT DOCUMENTS

WO 2007/002293 A2 1/2007
WO 2007/026834 A1 3/2007
WO 2008/045484 A1 4/2008
WO 2010/030815 A1 3/2010
WO 2009/063953 A1 3/2011
WO 2011/029855 A1 3/2011
WO 2011/161699 A2 12/2011
WO 2011/161699 A3 12/2011
WO 2012/168944 A1 12/2012
WO 2013/132317 A9 9/2013
WO 2013/144704 A1 10/2013
WO 2013/0173223 A1 11/2013
WO 2014/089495 A1 6/2014
WO 2014/151634 A1 9/2014
WO 2015/026634 A1 2/2015
WO 2015/033299 A1 3/2015
WO 2015/033301 A1 3/2015
WO 2015/033303 A1 3/2015
WO 2015/036927 A1 3/2015
WO 2015/044900 A1 4/2015
WO 2015/160641 A2 10/2015
WO 2015/160641 A3 10/2015
WO 2016/039749 A1 3/2016
WO 2016/057624 A1 4/2016
WO 2016/077518 A1 5/2016
WO 2016/100285 A1 6/2016
WO 2016/100608 A1 6/2016
WO 2016/142833 A1 9/2016
WO 2016/142835 A1 9/2016
WO 2016/142852 A1 9/2016
WO 2016/142886 A2 9/2016
WO 2016/142886 A3 9/2016
WO 2016/142894 A1 9/2016
WO 2016/149351 A1 9/2016

OTHER PUBLICATIONS

International Search Report and Written Opinion, PCT Application No. PCT/US2013/073692, dated Apr. 8, 2014, 9 pages.
International Search Report and Written Opinion corresponding to PCT/US2013/077257 dated Jun. 25, 2014; 10 pages.
International Search Report dated Aug. 28, 2017 corresponding to PCT/US2017/026290 filed Apr. 6, 2017; 4 pages.
Written Opinion of the ISA dated Aug. 28, 2017 corresponding to PCT/US2017/026290 filed Apr. 6, 2017; 7 pages.
Extended European Search Report corresponding to EP 13866291.1 dated Apr. 18, 2016; 13 pages.
Extended European Search Report corresponding to EP 13859762 dated Sep. 29, 2016, 7 pages.
Extended European Search Report corresponding to EP 17779801.4 dated Nov. 5, 2019; 15 pages.
Ajuebor, Maureen N. et al., "Role of chemokines and chemokine receptors in the gastrointestinal tract," *Immunology* (2002; accepted Jul. 17, 2001); 105:137-143.
Amin, Kawa et al., CC Chemokine Receptors CCR1 and CCR4 are Expressed on Airway Mast Cells in Alelrgic Asthma, *J. Allergy, Clin. Immunol.* (Dec. 2005); 116(6):1383-1385.
Anderson, Matthew W. et al., "C-C Chemokine Receptor 1 Expression in Human Hematolymphoid Nepolasia," *Am. J. Clin. Pathol.* (Mar. 1, 2010); 133(3):473-483.
Borregaard, Jeanett et al., "Evaluation of the effect of the specific CCR1 antagonist CP-481715 on the clinical and cellular responses observed following epicutaneous nickel challenge in human subjects," *Contact Dermatitis* (Feb. 18, 2008); 59:212-219.
Brand, Francois-Xavier et al., Prospect for Anti-HER2 Receptor Therapy in Breast Cancer, *Anticancer Research* (2006; Accepted Sep. 26, 2005) 26:463-470.
Chen, Lieping et al., "Anti-PD-1/PD-L1 therapy of human cancer: past, present, and future," *J Clin Invest.* (Sep. 2015) 125(9):3384-3391.
Chemical Abstracts STN Record for CAS RN 1355557-26-4, entered Feb. 2, 2012.
Chemical Abstracts STN Record for CAS RN 1385289-59-7, entered Aug. 2, 2012.
Chemical Abstracts STN Record for CAS RN 1376355-87-1, entered Jun. 7, 2012.
Dairaghi, Daniel J. et al., "CCR1 blockade reduces tumor burden and osteolysis in vivo in a mouse model of myeloma bone disease," *Blood* (Aug. 16, 2012); 120(7):1449-1457.
Danziger, D. J. et al., "Automated Site-Directed Drug Design: A General Algorithm for Knowledge Acquisition about Hydrogen-Bonding Regions at Protein Surfaces," *Proceedings of the Royal Society of London. Series B, Biological Sciences* (Mar. 22, 1989); 236(1283):101-113.
Dorwald, Florencio Zaragoza "Side Reactions in Organic Synthesis: A Guide to Successful Synthesis Design," © 2005 Wiley-VCH Verlag GmbH & Co. KGaA, Wienheim, prface and chapter 1, pp. 1-16.
Gao, Wei et al., "Targeting of the chemokine receptor CCR1 suppresses development of acute and chronic cardiac allograft rejection," *J. Clin. Invest.* (2000; accepted Nov. 23, 1999); 105(1):35-44.
Garcia-Teijido, Paula et al., "Tumor-Infiltrating Lymphocytes in Triple Negative Breast Cancer: The Future of Immune Targeting," *Clinical Medicine Insights: Oncology* (Apr. 5, 2016) 10(supple1):31-39.
Gladue, Ronald P., "Current status of CCR1 antagonists in clinical trials," *Chemokine Biology—Basic Research and Clinical Application*, vol. II (© 2007 Birkhäuser Verlag Basel/Switzerland); pp. 103-113.
Gladue, Ronald P. et al., "CCR1 Antagonists: What Have We Learned From Clinical Trials," *Current Topics in Medicinal Chemistry* (revised Jan. 7, 2010); 10(13):1268-1277.
Hamanishi, Junzo et al., "PD-1/PD-L1 blockade in cancer treatment: perspectives and issues," *Int J Clin Oncol* (published online Feb. 22, 2016) 21:462-473.
Helal, Christopher J. et al., "Potent and cellularly active 4-aminoimidazole inhibitors of cyclin-dependent kinase 5/p25 for the treatment of Alzheimer's disease," *Bioorg. Med. Chem. Lett.* (Aug. 4, 2009); 19:5703-5707.
Hesselgesser, Joseph et al., "Identification and Characterization of Small Molecule Functional Antagonists of the CCR1 Chemokine Receptor," *J. Biol. Chem.* (Apr. 1, 1998); 273(25):15687-15692.
Joubert, Philippe et al., "Expression and Regulation of CCR1 by Airway Smooth Muscle Cells in Asthma," *J. Immunol.* (Feb. 1, 2008); 180:1268-1275.

(56) References Cited

OTHER PUBLICATIONS

Jung, Heiyoun et al., "Combination therapy of chemokine receptor inhibition plus PDL-1 blockade potentiates anti-tumor effects in a murine model of breast cancer," *Journal for ImmunoTherapy of Cancer* (Nov. 4, 2015) 3(Suppl2):P227; 1 page.
Jung, Heiyoun et al., "Abstract 564: Combination therapy of chemokine receptor inhibition plus PD-L1 blockade potentiates antitumor effects in a murine model of breast cancer," *Cancer Research* (Jul. 2016); 76(14):564 and $107^{th}$ Annual Meeting of the American Association for Cancer Research (AACR); New Orleans, LA, USA; Apr. 16-20, 2016; 4 pages.
Klinke, David J., II, "Is immune checkpoint modulation a potential therapeutic option in triple negative breast cancer?" *Breast Cancer Research* (Nov. 7, 2014) 16:457; 2 pages.
Liang, Meina et al., "Species selectivity of a small molecule antagonist for the CCR1 chemokine receptor," *Eur. J. Pharmacol.* (2000; accepted Nov. 30, 1999); 389(1):41-49.
Liang, Meina et al., "Identification and Characterization of a Potent, Selective, and Orally Active Antagonist of the CC Chemokine Receptor-1," *J. Biol. Chem.* (Mar. 29, 2000); 275(25):19000-19008.
Ng, Howard P. et al., "Discovery of Novel Non-Peptide CCR1 Receptor Antagonists," *J. Med. Chem.* (Jun. 21, 1999); 42(22):4680-4694.
Pease, James et al., "Chemokine Receptor Antagonists," *J. Med. Chem.* (Aug. 29, 2012); 55:9363-9392.
Rottman, James B. et al., "Leukocyte recruitment during onsent of experimental allergic encephalomyelitis is CCR1 dependent," *Eur. J. Immunol.* (May 15, 2000); 30:2372-2377.
Strome, Scott E. et al., "A Mechanistic Perspective of Monoclonal Antibodies in Cancer Therapy Beyond Target-Related Effects," *The Oncologist* (accepted for publication Jun. 27, 2007) 12:1084-1095.
Vallet S. et al., "CCR1 as a target for multiple myeloma," (Abstract, only) *Expert Opin. Ther. Targets* (Sep. 2011; Epub May 24, 2011); 15(9):1037-47.
Goodman, Alice, "Anti-PD-L1 Agent Shows Activity in Early Study of Triple-Negative Breast Cancer," *The ASCO Post* (Jun. 10, 2015); 4 pages.
Jung, Heiyoun, "Abstract A90: Combination therapy of chemokine receptor inhibition plus PDL-1 blockade potentiates anti-tumor effects in a murine model of breast cancer," *Molecular Cancer Therapeutics* (Dec. 2015) 14(12 Suppl 2);Proceedings of the AACR-NCI-EORTC International Conference: Molecular Targets and Cancer Therapeutics (Nov. 5-9, 2015; Boston, MA; Philadelphia PA): AACR; 3 pages.

* cited by examiner

Analysis of mRNA data from The Cancer Genome Atlas (TCGA)
RSEM: RNA-Seq by Expectation-Maximization ****: p<0.0001

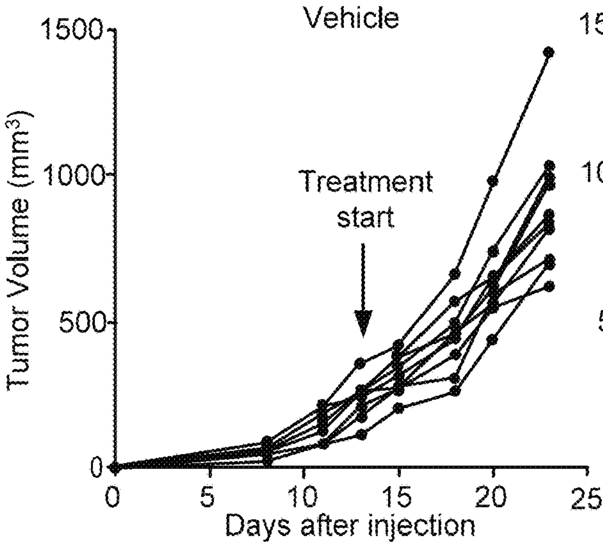

FIG. 3A
Vehicle
Tumor Volume (mm³)
Treatment start
Days after injection

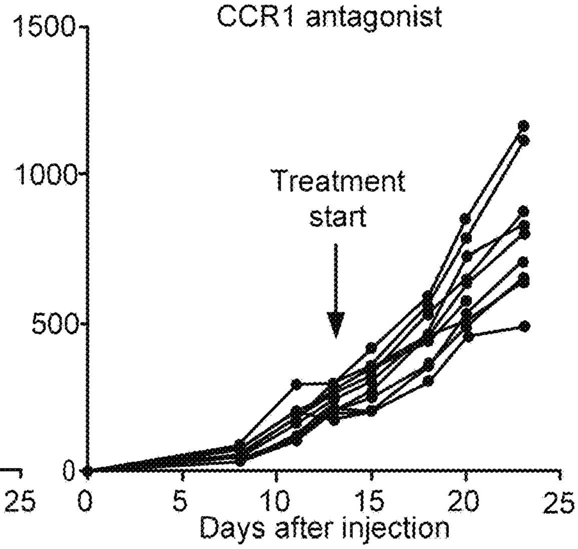

FIG. 3B
CCR1 antagonist
Treatment start
Days after injection

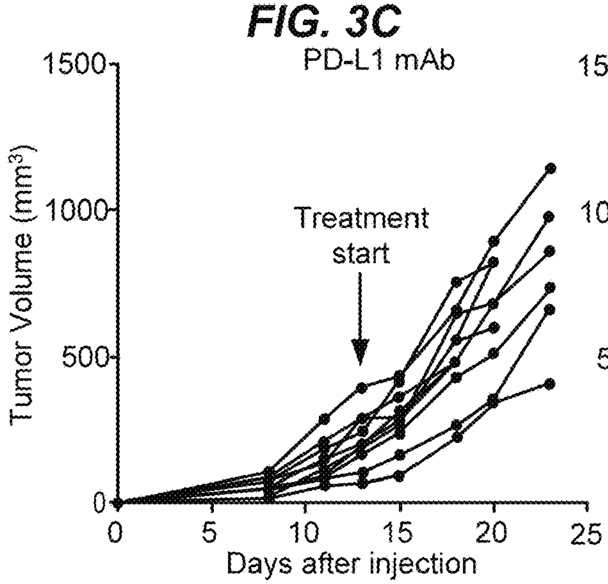

FIG. 3C
PD-L1 mAb
Tumor Volume (mm³)
Treatment start
Days after injection

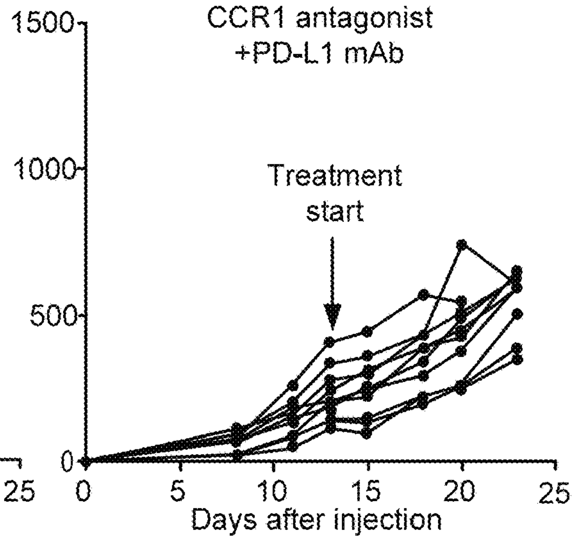

FIG. 3D
CCR1 antagonist
+PD-L1 mAb
Treatment start
Days after injection

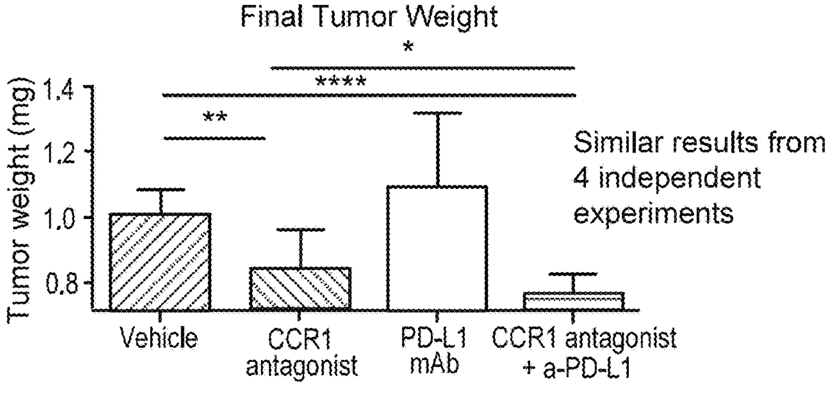

FIG. 3E
Final Tumor Weight
Tumor weight (mg)
Similar results from
4 independent
experiments
Vehicle
CCR1 antagonist
PD-L1 mAb
CCR1 antagonist + a-PD-L1

Normal mouse 4T1 tumor bearing mouse

G-MDSCs: $CD11b^{pos}Ly6G^{high}Ly6C^{high}$ M-MDSCs: $CD11b^{pos}Ly6G^{neg}Ly6C^{high}$ Gate is based on isotype control staining G-MDSCs: CD11b$^{pos}$Ly6G$^{high}$Ly6C$^{high}$ M-MDSCs: CD11b$^{pos}$Ly6G$^{neg}$Ly6C$^{high}$ Macrophages: CD11b$^{pos}$Ly6G$^{neg}$Ly6C$^{neg}$F4/80$^{pos}$

: p<0.005, *: p<0.0005

*: p<0.05, ****: p<0.0001

REDUCING TUMOR BURDEN BY ADMINISTERING CCR1 ANTAGONISTS IN COMBINATION WITH PD-1 INHIBITORS OR PD-L1 INHIBITORS

CROSS-REFERENCES TO RELATED APPLICATIONS

This application is a divisional of U.S. patent application Ser. No. 15/480,992 filed Apr. 6, 2017, now U.S. Pat. No. 10,568,876, which is an application claiming benefit under 35 U.S.C. § 119(e) of U.S. Provisional Application No. 62/319,689 filed Apr. 7, 2016, each of which are incorporated herein by reference in their entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Cancerous tumors exploit numerous mechanisms to evade the body's natural cytotoxic immune response such that the tumors are tolerated by the immune system. These mechanisms include dysfunctional T-cell signaling, suppressive regulatory cells, and immune checkpoints that normally act to downregulate the intensity of adaptive immune responses and protect healthy tissues from collateral damage. For instance, tumors develop immune resistance, particularly to T cells that are specific to tumor antigens, by recruiting myeloid-derived suppressor cells (MDSCs) to the tumors and their surrounding microenvironment.

MDSCs express chemokine receptors such as the chemokine receptor CCR1, and have immunosuppressive functions. MDSCs play a key role in a tumor's ability to suppress immune responses. Another key component to this suppression is the activation of immune checkpoints which, in turn, restricts T cell activation and infiltration into tumors. Immune checkpoints refer to inhibitory pathways of the immune system that are essential to maintaining self-tolerance and controlling immune responses in peripheral tissues to minimize collateral tissue damage.

Programmed Death-1 (PD-1) is one of numerous immune checkpoint receptors that are expressed by activated T cells and mediate immunosuppression. Ligands of PD-1 include Programmed Death Ligand-1 (PD-L1) and Programmed Death Ligand-2 (PD-L2) which are expressed on antigen-presenting cells as well as on many human cancer cells. PD-L1 and PD-L2 can downregulate T cell activation and cytokine secretion upon binding to PD-1.

It has been shown that PD-1/PD-L1 interaction inhibitors can mediate potent antitumor activity and are effective for treating some cancers. Inhibition of CCR1 has been associated with reducing tumor burden in a mouse model of myeloma bone disease (Dairaghi et al., *Blood,* 2012, 12(7): 1449-1457). There remains a need for an effective treatment for cancers such as solid tumor cancers.

BRIEF SUMMARY OF THE INVENTION

In one aspect, provided herein is a method for treating a subject having a solid tumor cancer. The method comprises administering to the subject in need thereof a therapeutically effective amount of a CCR1 chemokine receptor antagonist and a therapeutically effective amount of a PD-1 inhibitor or a PD-L1 inhibitor.

In another aspect, provided herein is a composition for treating a subject having a solid tumor cancer. The composition comprises a therapeutically effective amount of a CCR1 chemokine receptor antagonist and a therapeutically effective amount of a PD-1 inhibitor or a PD-L1 inhibitor, and a pharmaceutically acceptable carrier or excipient.

In yet another aspect, provided herein is a kit for treating a subject having a solid tumor cancer. The kit comprises a therapeutically effective amount of a CCR1 chemokine receptor antagonist and a therapeutically effective amount of a PD-1 inhibitor or a PD-L1 inhibitor, with instruction for effective administration.

Other objects, features, and advantages of the present invention will be apparent to one of skill in the art from the following detailed description and figures.

BRIEF DESCRIPTION OF THE DRAWINGS

FIG. 1A), CCL7 (MCP-3; FIG. 1B), and PD-L1 (FIG. 1D) was seen in triple negative breast cancer patients. The expression level of CCL3 (MIP-1α) is depicted in FIG. 1C. FIG. 1E shows that CCR1 and PD-L1 expression correlated well in human breast cancer patient samples.

FIGS. 3A-3E illustrate that combination therapy of a CCR1 antagonist with an anti-PD-L1 antibody decreases the progression of aggressive, metastatic tumors (e.g., established 4T1 tumors). 4T1 mammary carcinoma mice were administered vehicle (FIG. 3A), CCR1 antagonist alone (FIG. 3B), PD-L1 antibody alone (FIG. 3C), or a combination of the CCR1 antagonist and the PD-L1 antibody (FIG. 3D). Comparison of final tumor weight in FIG. 3E shows that the combination therapy was effective at minimizing or reducing tumor progression.

FIG. 4A illustrates that mice administered the CCR1 antagonist had fewer metastatic nodes per lung compared to similar mice administered vehicle. FIG. 4B provides images of the metastatic nodes in the lungs.

FIG. 6B shows that the highest percentage of CCR1 expressing cells are G-MDSCs.

FIG. 7A compares the percentage of G-MDSCs in tumor infiltrating immune cells and tumor weight. FIG. 7B compares the percentage of $CD8^+$ T cells in tumor infiltrating immune cells and tumor weight.

FIG. 9A shows that the CCR1 antagonist decreases G-MDSC infiltration into 4T1 tumors. FIG. 9B shows the level of M-MDSC infiltration in 4T1 tumors in treated mice. FIG. 9C shows increases of CD8 T cell infiltration into 4T1 tumors in mice treated with CCR1 antagonist alone or in combination with a PD-L1 mAb. FIG. 9D shows the level of B cell infiltration into 4T1 tumors of treated mice.

FIG. 10 also shows how this pathway may promote tumor progression.

DETAILED DESCRIPTION OF THE INVENTION

I. Introduction

Figure 1A:
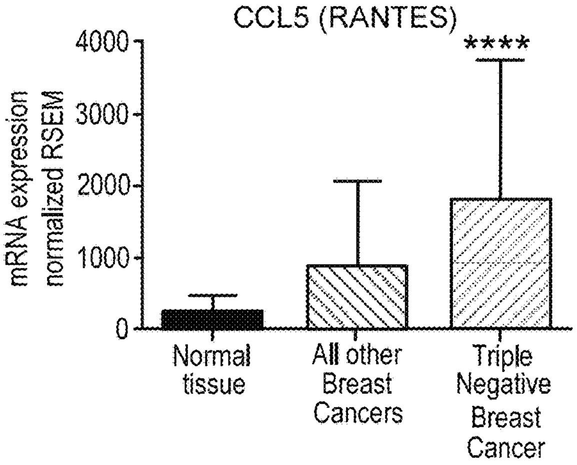
FIGS. 1A-1E show expression levels of ligands for chemokine receptor CCR1 (CCL3, CCL5, and CCL7), PD-L1, and CCR1 in samples from breast cancer patients. Significantly elevated expression of CCL5 (RANTES.

Provided herein are methods, compositions and kits for treating a cancer such a solid tumor cancer in a subject in need thereof by administering a combination therapy of a CCR1 antagonist and either a PD-1 inhibitor or a PD-L1 inhibitor. The present invention is based, in part, on the synergistic effect of both the CCR1 antagonist in combination with either the PD-1 inhibitor or PD-L1 inhibitor reducing or decreasing tumor burden, tumor progression, and/or metastasis. In some instances, a therapy comprising a CCR1 antagonist alone can reduce metastasis, e.g., lung metastasis.

II. Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkane" or "heterocycloalkyl" refers to a cycloalkyl group that contains from one to five heteroatoms selected from N, O, and S, wherein the nitrogen and sulfur atoms are optionally oxidized, and the nitrogen atom(s) are optionally quaternized. The heterocycloalkane may be a monocyclic, a bicyclic or a polycylic ring system. Non limiting examples of heterocycloalkane groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkane group can be attached to the remainder of the molecule through a ring carbon or a heteroatom.

The term "alkylene" by itself or as part of another substituent means a divalent radical derived from an alkane, as exemplified by $—CH_2CH_2CH_2CH_2—$. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, ∿∿, that intersects a single, double or triple bond in any chemical structure depicted herein, represent the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or $—NR^aR^b$ is meant to include piperidinyl, pyrrolidinyl, morpholinyl, azetidinyl and the like.

The term "di-($C_{1-4}$alkyl)amino-$C_{1-4}$ alkyl" refers to an amino group bearing two $C_{1-4}$ alkyl groups that can be the same or different (e.g., methyl, ethyl, propyl, isopropyl, n-butyl, sec-butyl, isobutyl and tert-butyl) and which is attached to the remainder of the molecule through a $C_{1-4}$ alkyl group (a one to four carbon alkylene linking group).

Examples of di-($C_{1-4}$ alkyl)amino-$C_{1-4}$ alkyl groups include dimethylaminomethyl, 2-(ethyl(methyl)amino)ethyl, 3-(dimethylamino)butyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "heteroaryl-alkyl" is meant to include those radicals in which a heteroaryl group is attached to an alkyl group (e.g., pyridylmethyl, thiazolylethyl, and the like).

The above terms (e.g., "alkyl," "aryl" and "heteroaryl"), in some embodiments, will refer to both substituted and unsubstituted forms of the indicated radical. Preferred substituents for each type of radical are provided below.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —$CO_2$R', —CONR'R", —OC(O)NR'R", —NR"C(O)R', —NR'—C(O)NR"R'", —NR"C$(O)_2$R', —NH—C($NH_2$)═NH, —NR'C($NH_2$)═NH, —NH—C($NH_2$)═NR', —S(O)R', —S$(O)_2$R', —S$(O)_2$NR'R", —NR'S$(O)_2$R", —CN and —$NO_2$ in a number ranging from zero to (2 m'+1), where m' is the total number of carbon atoms in such radical. R', R" and R'" each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C$(O)_2$R', —NR'—C(O)NR"R'", —NH—C($NH_2$)═NH, —NR'C($NH_2$)═NH, —NH—C($NH_2$)═NR', —S(O)R', —S$(O)_2$R', —S$(O)_2$NR'R", —NR'S$(O)_2$R", —$N_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—$(CH_2)_q$-U-, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-($CH_2$), —B—, wherein A and B are independently —$CH_2$—, —O—, —NH—, —S—, —S(O)—, —S$(O)_2$—, —S$(O)_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—X—$(CH_2)_t$—, where s and t are independently integers of from 0 to 3, and X is —O—, —NR'—, —S—, —S(O)—, —S$(O)_2$—, or —S$(O)_2$NR'—. The substituent R' in —NR'— and —S$(O)_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14($^{14}C$), or non-radioactive isotopes, such as deuterium ($^2H$) or carbon-13 ($^{13}C$). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

Compounds of the invention having formulae I-V can exist in different isomeric forms. As used herein, the terms cis or trans are used in their conventional sense in the chemical arts, i.e., referring to the position of the substituents to one another relative to a reference plane, e.g., a double bond, or a ring system, such as a decalin-type ring system or a hydroquinolone ring system: in the cis isomer, the substituents are on the same side of the reference plane, in the trans isomer the substituents are on opposite sides. Additionally, different conformers are contemplated by the present invention, as well as distinct rotamers. Conformers are conformational isomers that can differ by rotations about one or more σ bonds. Rotamers are conformers that differ by rotation about only a single σ bond.

The term "cancer" refers to a disease characterized by the uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

The term "PD-1" or "PD-1 receptor" refers to the programmed death-1 protein, a T-cell co-inhibitor, also known as CD279. The amino acid sequence of the human full-length PD-1 protein is set forth, for example, in GenBank Accession Number NP_005009.2. PD-1 is a 288 amino acid protein with an extracellular N-terminal domain which is IgV-like, a transmembrane domain and an intracellular domain containing an immunoreceptor tyrosine-based inhibitory (ITIM) motif and an immunoreceptor tyrosine-based switch (ITSM) motif (Chattopadhyay et al., *Immunol Rev,* 2009, 229(1):356-386). The term "PD-1" includes recombinant PD-1 or a fragment thereof, or variants thereof. The PD-1 receptor has two ligands, PD-ligand-1 (PD-L1) and PD-ligand-2 (PD-L2).

The term "PD-L1" or "programmed death ligand 1" refers to a ligand of the PD-1 receptor also known as CD274 and B7H 1. The amino acid sequence of the human full-length PD-L1 protein is set forth, for example, in GenBank Accession Number NP_054862.1 PD-L1 is a 290 amino acid protein with an extracellular IgV-like domain, a transmembrane domain and a highly conserved intracellular domain of approximately 30 amino acids. PD-L1 is constitutively expressed on many cells such as antigen presenting cells (e.g., dendritic cells, macrophages, and B-cells) and on hematopoietic and non-hematopoietic cells (e.g., vascular endothelial cells, pancreatic islets, and sites of immune privilege). PD-L1 is also expressed on a wide variety of tumors, virally-infected cells and autoimmune tissue.

The programmed death 1 (PD-1/PD-L1) pathway acts as a checkpoint to limit T-cell-mediated immune responses. Both PD-1 ligands, PD-L1 and PD-L2, can engage the PD-1 receptor and induce PD-1 signaling and reversible inhibition of T-cell activation and proliferation. When PD-1 ligands on the surface or cancer cells or neighboring cells, these ligands bind to PD-1 receptor positive immune effector cells and utilize the PD-1 pathway to evade an immune response.

The term "immune checkpoint inhibitor" or "immune checkpoint blockade" refers to any agent, molecule, compound, chemical, protein, polypeptide, macromolecule, etc. that blocks or inhibits in a statistically, clinically, or biologically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative immune checkpoint molecules that may be targeted for blocking or inhibition include, but are not limited to, CTLA-4, 4-1BB (CD137), 4-1BBL (CD137L), PDL1, PDL2, PD-1, B7-H3, B7-H4, BTLA, HVEM, TIM3, GALS, LAG3, TIM3, B7H3, B7H4, VISTA, KIR, 2B4 (belongs to the CD2 family of molecules and is expressed on all NK, γδ, and memory CD8+ (αβ) T cells), CD160 (also referred to as BY55) and CGEN-15049. Illustrative immune checkpoint inhibitors include durvalumab (anti-PD-L1 antibody; MEDI4736), pembrolizumab (anti-PD-1 monoclonal antibody), nivolumab (anti-PD-1 antibody), pidilizumab (CT-011; humanized anti-PD-1 monoclonal antibody), AMP224 (recombinant B7-DC-Fc fusion protein), BMS-936559 (anti-PD-L1 antibody), atezolizumab (MPLDL3280A; human Fc-optimized anti-PD-L1 monoclonal antibody), avuelumab (MSB0010718C; human anti-PD-L1 antibody), ipilimumab (anti-CTLA-4 checkpoint inhibitor), tremelimumab (CTLA-4 blocking antibody), and anti-OX40.

The terms "CCR1 antagonist" and "CCR1 chemokine receptor antagonist" are used interchangeably and refer to a small molecule that antagonizes the interaction of the chemokine receptor CCR1 and any one of its ligands. Such a compound could inhibit processes normally triggered by the receptor ligand interaction.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" (ORR) refers to the sum of complete response (CR) rate and partial response (PR) rate.

As used herein, "overall survival" refers to the percentage of individuals in a group who are likely to be alive after a particular duration of time.

III. Detailed Descriptions of Embodiments

In one aspect, the present invention provides a method for treating a subject having a solid tumor cancer. The method comprises administering to the subject in need thereof a therapeutically effective amount of a CCR1 chemokine receptor antagonist and a therapeutically effective amount of a PD-1 inhibitor or a PD-L1 inhibitor.

In some embodiments, the method comprises administering to the subject in need thereof a therapeutically effective amount of a CCR1 chemokine receptor antagonist and a therapeutically effective amount of a PD-1 inhibitor.

In some embodiments, the method comprises administering to the subject in need thereof a therapeutically effective amount of a CCR1 chemokine receptor antagonist and a therapeutically effective amount of a PD-L1 inhibitor.

In some embodiments, the CCR1 chemokine receptor antagonist is selected from compounds of formulae I-V, below, more particularly selected from compounds 1.001, 3.002, 4.005, 5.005, and 3.001 or a pharmaceutically acceptable salt thereof.

In some embodiments, the CCR1 chemokine receptor antagonist is selected from the group consisting of BL-5923, UCB-35625, BX-471, BI-638683, PS-031291, MLN-3701, AZD-4818, MLN-3897, CP-481715, F-18-CCR1, AOP-RANTES, PS-375179, and NSC-651016.

In some embodiments, the PD-1 inhibitor is selected from the group consisting of pembrolizumab, nivolumab, IBI-308, mDX-400, BGB-108, MEDI-0680, SHR-1210, PF-06801591, PDR-001, GB-226, STI-1110, biosimilars thereof, biobetters thereof, and bioequivalents thereof.

In some embodiments, the PD-1 inhibitor is selected from the group consisting of pembrolizumab, nivolumab, IBI-308, mDX-400, BGB-108, MEDI-0680, SHR-1210, PF-06801591, PDR-001, GB-226, and STI-1110.

In some embodiments, the PD-L1 inhibitor is selected from the group consisting of durvalumab, atezolizumab, avelumab, BMS-936559, ALN-PDL, TSR-042, KD-033, CA-170, STI-1014, KY-1003, biosimilars thereof, biobetters thereof, and bioequivalents thereof.

In some embodiments, the PD-L1 inhibitor is selected from the group consisting of durvalumab, atezolizumab, avelumab, BMS-936559, ALN-PDL, TSR-042, KD-033, CA-170, CA-327, STI-1014, KY-1003, biosimilars thereof, biobetters thereof, and bioequivalents thereof.

In some embodiments, the PD-L1 inhibitor is selected from the group consisting of durvalumab, atezolizumab, avelumab, BMS-936559, ALN-PDL, TSR-042, KD-033, CA-327, STI-1014, KY-1003, biosimilars thereof, biobetters thereof, and bioequivalents thereof.

In some embodiments, the PD-L1 inhibitor is selected from the group consisting of durvalumab, atezolizumab, avelumab, BMS-936559, ALN-PDL, TSR-042, KD-033, CA-170, STI-1014, and KY-1003.

In some embodiments, the PD-1 and/or PD-L1 inhibitor is selected from the compounds disclosed in US2015291549, WO16039749, WO15034820, and US2014294898 (BRISTOL MYERS SQUIBB CO) which are thereby incorporated by reference.

In some embodiments, the PD-1 and/or PD-L1 inhibitor is selected from the compounds disclosed in WO14151634, WO15160641, WO16039749, WO16077518, WO16100608, WO16149351, WO2016057624, WO2016100285, US2016194307, US2016222060, and US2014294898 (BRISTOL MYERS SQUIBB CO) which are thereby incorporated by reference.

In some embodiments, the PD-1 or PD-L1 inhibitor is selected from the compounds disclosed in U.S. Provisional Patent Application Nos. 62/355,119 or 62/440,100 which are hereby incorporated by reference.

In some embodiments, the PD-1 and/or PD-L1 inhibitor is selected from the group consisting of:

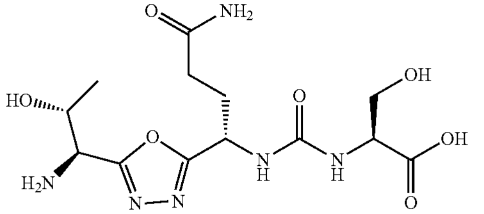

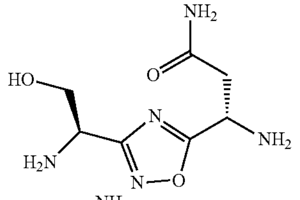

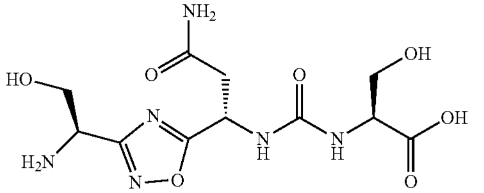

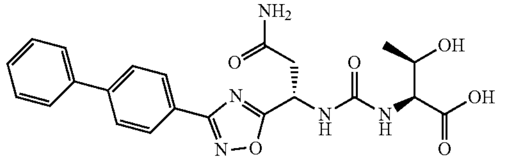

and

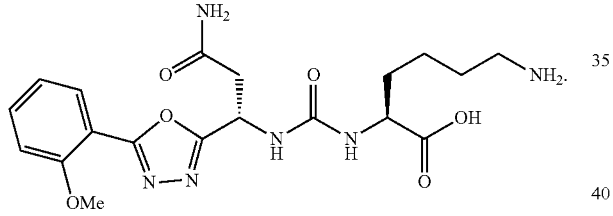

In some embodiments, the PD-1 anchor PD-L1 inhibitor is selected from the compounds disclosed in WO16142886, WO16142894, WO16142852, WO16142833, WO15033301, WO15033299, WO11161699, WO12168944, WO13132317, WO13144704, WO15033303, WO15036927, WO15044900, WO16142835, US2015073024, U.S. Pat. Nos. 8,907,053, 9,044,442, 9,096,642, 9,233,940, and US2016194295 (Aurigene discovery tech ltd) which are thereby incorporated by reference.

In some embodiments, the PD-1 anchor PD-L1 inhibitor is selected from the group consisting of durvalumab, atezolizumab, pembrolizumab, nivolumab, AP-106, AP-105, MSB-2311, CBT-501, avelumab, AK-105, IO-102, IO-103, PDR-001, CX-072, SHR-1316, JTX-4014, GNS-1480, recombinant humanized anti-PD1 mAb (Shanghai Junshi Biosciences), REGN-2810, pelareorep, SHR-1210, PD1/PDL1 inhibitor vaccine (THERAVECTYS), BGB-A317, recombinant humanized anti-PD-1 mAb (Bio-Thera Solutions), Probody targeting PD-1 (CytomX), XmAb-20717, FS-118, PSI-001, SN-PDL01, SN-PD07, PD-1 modified TILs (Sangamo Therapeutics), PRS-332, FPT-155, jienuo mAb (Genor Biopharma), TSR-042, REGN-1979, REGN-2810, resminostat, FAZ-053, PD-1/CTLA-4 bispecific antibody (MacroGenics), MGA-012, MGD-013, M-7824, PD-1 based bispecific antibody (Beijing Hanmi Pharmaceutical), AK-112, AK-106, AK-104, AK-103, BI-754091, ENUM-244C8, MCLA-145, MCLA-134, anti-PD1 oncolytic monoclonal antibody (Transgene SA), AGEN-2034, 1B1-308, WBP-3155, JNJ-63723283, MEDT-0680, SSI-361, CBT-502, anti-PD-1 bispecific antibody, dual targeting anti-PD-1/LAG-3 mAbs (TESARO), dual targeting anti-PD-1/TIM-3 mAbs (TESARO), PF-06801591, LY-3300054, BCD-100, STI-1110, pembrolizumab biosimilar, nivolumab biosimilar, PD-L1-TGF-beta therapy, KY-1003, STI-1014, GLS-010, AM-0001, GX-P2, KD-033, PD-L1/BCMA bispecific antibody (Immune Pharmaceuticals), PD-1/Ox40 targeting bispecific antibody (Immune Pharmaceuticals), BMS-936559, anti-PD-1/VEGF-A DARPins (Molecular Partners), mDX-400, ALN-PDL, PD-1 inhibitor peptide (Aurigene), siRNA loaded dendritic cell vaccine (Alnylam Pharmaceuticals), GB-226, PD-L1 targeting CAR-TNK-based immunotherapy (TNK Therapeutics/NantKwest), INSIX RA, INDUS-903, AMP-224, anti-CTLA-4/anti-PD-1 bispecific humanized antibody (Akeso Biopharma), B7-H1 vaccine (State Key Laboratory of Cancer Biology/Fourth Military Medical University), and GX-D1.

The CCR1 chemokine receptor antagonist and the PD-1 inhibitor or PD-L1 inhibitor can be administered concomitantly. In some cases, the CCR1 chemokine receptor antagonist and the PD-1 inhibitor are administered concomitantly. In some cases, the CCR1 chemokine receptor antagonist and the PD-L1 inhibitor are administered concomitantly. In some cases, the CCR1 chemokine receptor antagonist and the PD-1 inhibitor or the PD-L1 inhibitor are administered in a combination formulation. The CCR1 chemokine receptor antagonist and the PD-1 inhibitor can be administered in a combination formulation. Optionally, the CCR1 chemokine receptor antagonist and the PD-L1 inhibitor are administered in a combination formulation.

In other embodiments, the CCR1 chemokine receptor antagonist and the PD-1 inhibitor or the PD-L1 inhibitor are administered sequentially. In some cases, the CCR1 chemokine receptor antagonist and the PD-1 inhibitor are administered sequentially. In some cases, the CCR1 chemokine receptor antagonist and the PD-L1 inhibitor are administered sequentially. The CCR1 chemokine receptor antagonist can be administered prior to administration of the PD-1 inhibitor or the PD-L1 inhibitor.

In some embodiments, the CCR1 chemokine receptor antagonist can be administered prior to administration of the PD-L1 inhibitor. The CCR1 chemokine receptor antagonist can be administered after the administration of the PD-1 inhibitor or the PD-L1 inhibitor.

In some embodiments, the CCR1 chemokine receptor antagonist can be administered after administration of the PD-L1 inhibitor.

In some embodiments, the subject is a human subject.

In some embodiments, the solid tumor cancer can be a brain cancer, breast cancer, bladder cancer, bone cancer, colorectal cancer, lung cancer, kidney cancer, liver cancer, stomach cancer, prostate cancer, sarcoma, melanoma, carcinoma, and lymphoma.

In some embodiments, the solid tumor cancer is breast cancer.

In some embodiments, the solid tumor cancer is triple negative breast cancer.

In a second aspect, the present invention provides a composition for treating a subject having a solid tumor cancer. The composition comprises a therapeutically effective amount of a CCR1 chemokine receptor antagonist and a therapeutically effective amount of a PD-1 inhibitor or a PD-L1 inhibitor, and a pharmaceutically acceptable carrier or excipient.

In some embodiments, the composition comprises a therapeutically effective amount of a CCR1 chemokine receptor antagonist and a therapeutically effective amount of a PD-L1 inhibitor, and a pharmaceutically acceptable carrier or excipient.

In some embodiments, the CCR1 chemokine receptor antagonist is a compound selected from formulae I-V below.

In some embodiments, the CCR1 chemokine receptor antagonist is selected from the group consisting of 1.001, 3.002, 4.005, 5.005, and 3.001 or a pharmaceutically acceptable salt thereof.

In some embodiments, the CCR1 chemokine receptor antagonist is selected from the group consisting of BL-5923, UCB-35625, BX-471, BI-638683, PS-031291, MLN-3701, AZD-4818, MLN-3897, CP-481715, F-18-CCR1, AOP-RANTES, PS-375179, and NSC-651016.

In some embodiments, the PD-1 inhibitor is selected from the group consisting of pembrolizumab, nivolumab, IBI-308, mDX-400, BGB-108, MEDI-0680, SHR-1210, PF-06801591, PDR-001, GB-226, STI-1110, biosimilars thereof, biobetters thereof, and bioequivalents thereof.

In some embodiments, the PD-1 inhibitor is selected from the group consisting of pembrolizumab, nivolumab, IBI-308, mDX-400, BGB-108, MEDI-0680, SHR-1210, PF-06801591, PDR-001, GB-226, and STI-1110.

In some embodiments, the PD-L1 inhibitor is selected from the group consisting of durvalumab, atezolizumab, avelumab, BMS-936559, ALN-PDL, TSR-042, KD-033, CA-170, CA-327, STI-1014, KY-1003, biosimilars thereof, biobetters thereof, and bioequivalents thereof.

In some embodiments, the PD-L1 inhibitor is selected from the group consisting of durvalumab, atezolizumab, avelumab, BMS-936559, ALN-PDL, TSR-042, KD-033, CA-170, STI-1014, KY-1003, biosimilars thereof, biobetters thereof, and bioequivalents thereof.

In some embodiments, the PD-L1 inhibitor is selected from the group consisting of durvalumab, atezolizumab, avelumab, BMS-936559, ALN-PDL, TSR-042, KD-033, CA-170, STI-1014, and KY-1003.

In some embodiments, the PD-1 and/or PD-L1 inhibitor is selected from the compounds disclosed in WO14151634, WO15160641, WO16039749, WO16077518, WO16100608, WO16149351, WO2016057624, WO2016100285, US2016194307, US2016222060, US2014294898, US2015291549, and US2016194307 (BRISTOL MYERS SQUIBB CO) which are thereby incorporated by reference.

In some embodiments, the PD-1 or PD-L1 inhibitor is selected from the compounds disclosed in U.S. Provisional Patent Application Nos. 62/355,119 or 62/440,100 which are hereby incorporated by reference.

In some embodiments, the PD-1 and/or PD-L1 inhibitor is selected from the group consisting of:

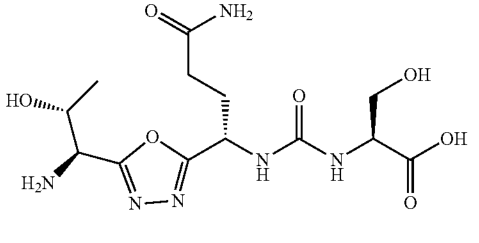

-continued

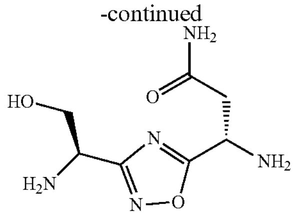

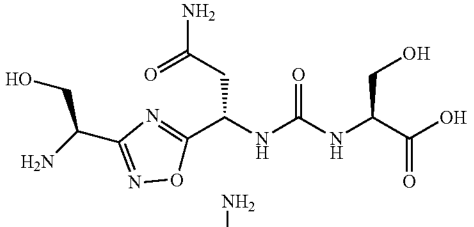

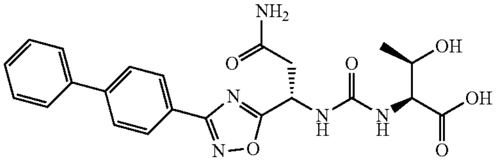

and

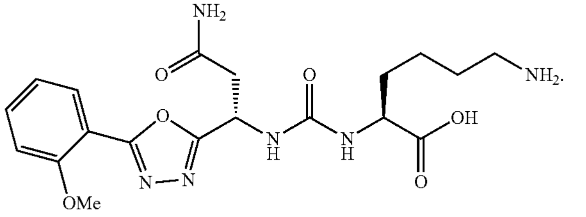

In some embodiments, the PD-1 and/or PD-L1 inhibitor is selected from the compounds disclosed in WO16142886, WO16142894, WO16142852, WO16142833, WO15033301, WO15033299, WO11161699, WO12168944, WO13132317, WO13144704, WO15033303, WO15036927, WO15044900, WO16142835, US2015073024, U.S. Pat. Nos. 8,907,053, 9,044,442, 9,096,642, 9,233,940, and US2016194295 (Aurigene discovery tech ltd) which are thereby incorporated by reference.

In some embodiments, the PD-1 and/or PD-L1 inhibitor is selected from the group consisting of durvalumab, atezolizumab, pembrolizumab, nivolumab, AP-106, AP-105, MSB-2311, CBT-501, avelumab, AK-105, IO-102, IO-103, PDR-001, CX-072, SHR-1316, JTX-4014, GNS-1480, recombinant humanized anti-PD1 mAb (Shanghai Junshi Biosciences), REGN-2810, pelareorep, SHR-1210, PD1/PDL1 inhibitor vaccine (THERAVECTYS), BGB-A317, recombinant humanized anti-PD-1 mAb (Bio-Thera Solutions), Probody targeting PD-1 (CytomX), XmAb-20717, FS-118, PSI-001, SN-PDL01, SN-PD07, PD-1 modified TILs (Sangamo Therapeutics), PRS-332, FPT-155, jienuo mAb (Genor Biopharma), TSR-042, REGN-1979, REGN-2810, resminostat, FAZ-053, PD-1/CTLA-4 bispecific antibody (MacroGenics), MGA-012, MGD-013, M-7824, PD-1 based bispecific antibody (Beijing Hanmi Pharmaceutical), AK-112, AK-106, AK-104, AK-103, BI-754091, ENUM-244C8, MCLA-145, MCLA-134, anti-PD1 oncolytic monoclonal antibody (Transgene SA), AGEN-2034, IBI-308, WBP-3155, JNJ-63723283, MEDI-0680, SSI-361, CBT-502, anti-PD-1 bispecific antibody, dual targeting anti-PD-1/LAG-3 mAbs (TESARO), dual targeting anti-PD-1/TIM-3 mAbs (TESARO), PF-06801591, LY-3300054, BCD-100, STI-1110, pembrolizumab biosimilar, nivolumab biosimilar, PD-L1-TGF-beta therapy, KY-1003, STI-1014, GLS-010, AM-0001, GX-P2, KD-033, PD-L1/BCMA bispecific antibody (Immune Pharmaceuticals), PD-1/Ox40 targeting bispecific antibody (Immune Pharmaceuticals), BMS-936559, anti-PD-1NEGF-A DARPins (Molecular Partners), mDX-400, ALN-PDL, PD-1 inhibitor peptide (Aurigene), siRNA loaded dendritic cell vaccine (Alnylam Pharmaceuticals), GB-226, PD-L1 targeting CAR-TNK-based immunotherapy (TNK Therapeutics/NantKwest), INSIX RA, INDUS-903, AMP-224, anti-CTLA-4/anti-PD-1 bispecific humanized antibody (Akeso Biopharma), B7-H1 vaccine (State Key Laboratory of Cancer Biology/Fourth Military Medical University), and GX-D1.

In some embodiments, the CCR1 chemokine receptor antagonist and the PD-1 inhibitor or the PD-L1 inhibitor are formulated for concomitant administration.

In other embodiments, the CCR1 chemokine receptor antagonist and the PD-1 inhibitor or the PD-L1 inhibitor are formulated for sequential administration.

In yet another aspect, provided herein is a kit for treating a subject having a solid tumor cancer. The kit comprises a therapeutically effective amount of a CCR1 chemokine receptor antagonist and a therapeutically effective amount of a PD-1 inhibitor or a PD-L1 inhibitor, with instruction for effective administration.

In some embodiments, the kit comprises a therapeutically effective amount of a CCR1 chemokine receptor antagonist and a therapeutically effective amount of a PD-L1 inhibitor, with instruction for effective administration.

In some embodiments, the CCR1 chemokine receptor antagonist is selected from the group consisting of 1.001, 3.002, 4.005, 5.005, and 3.001, or a pharmaceutically acceptable salt thereof.

In some embodiments, the CCR1 chemokine receptor antagonist is selected from the group consisting of BL-5923, UCB-35625, BX-471, BI-638683, PS-031291, MLN-3701, AZD-4818, MLN-3897, CP-481715, F-18-CCR1, AOP-RANTES, PS-375179, and NSC-651016.

In some embodiments, the PD-1 inhibitor is selected from the group consisting of pembrolizumab, nivolumab, IBI-308, mDX-400, BGB-108, MEDI-0680, SHR-1210, PF-06801591, PDR-001, GB-226, STI-1110, biosimilars thereof, biobetters thereof, and bioequivalents thereof.

In some embodiments, the PD-1 inhibitor is selected from the group consisting of pembrolizumab, nivolumab, IBI-308, mDX-400, BGB-108, MEDI-0680, SHR-1210, PF-06801591, PDR-001, GB-226, and STI-1110.

In some embodiments, the PD-L1 inhibitor is selected from the group consisting of durvalumab, atezolizumab, avelumab, BMS-936559, ALN-PDL, TSR-042, KD-033, CA-170, CA-327, STI-1014, KY-1003, biosimilars thereof, biobetters thereof, and bioequivalents thereof.

In some embodiments, the PD-L1 inhibitor is selected from the group consisting of durvalumab, atezolizumab, avelumab, BMS-936559, ALN-PDL, TSR-042, KD-033, CA-170, STI-1014, KY-1003, biosimilars thereof, biobetters thereof, and bioequivalents thereof.

In some embodiments, the PD-L1 inhibitor is selected from the group consisting of durvalumab, atezolizumab, avelumab, BMS-936559, ALN-PDL, TSR-042, KD-033, CA-170, STI-1014, and KY-1003.

In some embodiments, the PD-1 anchor PD-L1 inhibitor is selected from the compounds disclosed in WO14151634, WO15160641, WO16039749, WO16077518, WO16100608, WO16149351, WO2016057624, WO2016100285, US2016194307, US2016222060, US2015291549, US2016194307 and US2014294898 (BRISTOL MYERS SQUIBB CO) which are thereby incorporated by reference.

In some embodiments, the PD-1 or PD-L1 inhibitor is selected from the compounds disclosed in U.S. Provisional Patent Application No. 62/355,119 or 62/440,100 which are hereby incorporated by reference.

In some embodiments, the PD-1 and/or PD-L1 inhibitor is selected from the group consisting of:

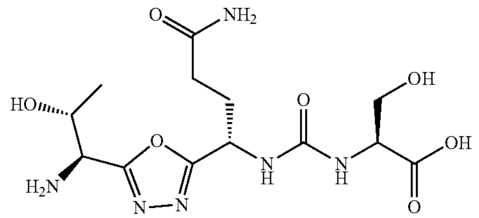

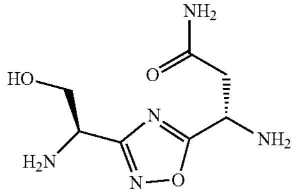

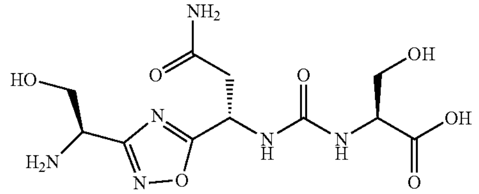

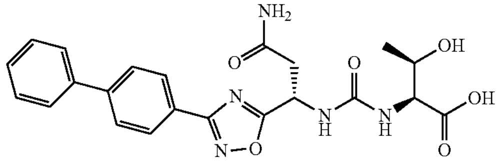

and

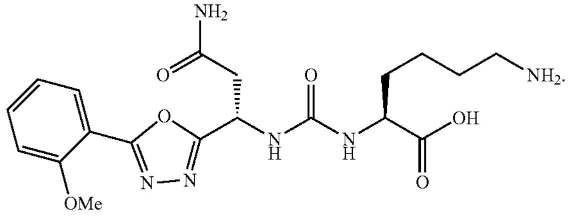

In some embodiments, the PD-1 anchor PD-L1 inhibitor is selected from the compounds disclosed in WO16142886, WO16142894, WO16142852, WO16142833, WO15033301, WO15033299, WO11161699, WO12168944, WO13132317, WO13144704, WO15033303, WO15036927, WO15044900, WO16142835, US2015073024, U.S. Pat. Nos. 8,907,053, 9,044,442, 9,096,642, 9,233,940, and US2016194295 (Aurigene discovery tech ltd) which are thereby incorporated by reference.

In some embodiments, the PD-1 anchor PD-L1 inhibitor is selected from the group consisting of durvalumab, atezolizumab, pembrolizumab, nivolumab, AP-106, AP-105, MSB-2311, CBT-501, avelumab, AK-105, IO-102, IO-103, PDR-001, CX-072, SHR-1316, JTX-4014, GNS-1480, recombinant humanized anti-PD1 mAb (Shanghai Junshi Biosciences), REGN-2810, pelareorep, SHR-1210, PD1/PDL1 inhibitor vaccine (THERAVECTYS), BGB-A317, recombinant humanized anti-PD-1 mAb (Bio-Thera Solutions), Probody targeting PD-1 (CytomX), XmAb-20717, FS-118, PSI-001, SN-PDL01, SN-PD07, PD-1 modified TILs (Sangamo Therapeutics), PRS-332, FPT-155, jienuo mAb (Genor Biopharma), TSR-042, REGN-1979, REGN-2810, resminostat, FAZ-053, PD-1/CTLA-4 bispecific antibody (MacroGenics), MGA-012, MGD-013, M-7824, PD-1 based bispecific antibody (Beijing Hanmi Pharmaceutical), AK-112, AK-106, AK-104, AK-103, BI-754091, ENUM-244C8, MCLA-145, MCLA-134, anti-PD1 oncolytic monoclonal antibody (Transgene SA), AGEN-2034, IBI-308, WBP-3155, JNJ-63723283, MEDI-0680, SSI-361, CBT-502, anti-PD-1 bispecific antibody, dual targeting anti-PD-1/LAG-3 mAbs (TESARO), dual targeting anti-PD-1/TIM-3 mAbs (TESARO), PF-06801591, LY-3300054, BCD-100, STI-1110, pembrolizumab biosimilar, nivolumab biosimilar, PD-L1-TGF-beta therapy, KY-1003, STI-1014, GLS-010, AM-0001, GX-P2, KD-033, PD-L1/BCMA bispecific antibody (Immune Pharmaceuticals), PD-1/Ox40 targeting bispecific antibody (Immune Pharmaceuticals), BMS-936559, anti-PD-1NEGF-A DARPins (Molecular Partners), mDX-400, ALN-PDL, PD-1 inhibitor peptide (Aurigene), siRNA loaded dendritic cell vaccine (Alnylam Pharmaceuticals), GB-226, PD-L1 targeting CAR-TNK-based immunotherapy (TNK Therapeutics/NantKwest), INSIX RA, INDUS-903, AMP-224, anti-CTLA-4/anti-PD-1 bispecific humanized antibody (Akeso Biopharma), B7-H1 vaccine (State Key Laboratory of Cancer Biology/Fourth Military Medical University), and GX-D1.

In some embodiments, the CCR1 chemokine receptor antagonist and the PD-1 inhibitor or the PD-L1 inhibitor are formulated for concomitant administration.

In other embodiments, the CCR1 chemokine receptor antagonist and the PD-1 inhibitor or the PD-L1 inhibitor are formulated for sequential administration.

A. CCR1 Antagonists

Methods, compositions, and kits provided herein include a CCR1 antagonist. In some embodiments, the CCR1 antagonist is selected from formulae I, II, III, IV and V described below, as well as the subformulae provided. In some embodiments, the CCR1 antagonist is selected from compounds 1.001, 3.002, 4.005, 5.005, or 3.001 as described below, or a pharmaceutically acceptable salt thereof. In some cases, the CCR1 antagonist can be any compound that can antagonize or inhibit the chemokine receptor CCR1 including, but not limited to, those described in, for example, U.S. Pat. Nos. 7,524,845; 7,576,106; 7,629,344; 8,343,975; 9,169,248; and U.S. Patent Application Nos. 2014/0171420 and 2014/0179733, the disclosures are herein incorporated by reference in their entirety for all purposes.

In some embodiments, a compound that inhibits one or more functions of CCR1 may be administered to a subject to treat a solid tumor cancer. In other embodiments, a compound that inhibits one or more functions of CCR1 is administered to stimulate (induce or enhance) an immune response, resulting in the beneficial stimulation of an anti-cancer response.

In some embodiments, provided herein is a method for decreasing lung metastasis by administering a CCR1 antagonist monotherapy. The CCR1 antagonist can be any one disclosed herein.

In some embodiments, the CCR1 antagonists have the formula:

(I)

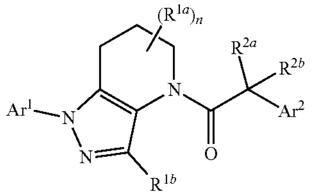

or a pharmaceutically acceptable salt, rotamer or optical isomer thereof.

In formula I, the subscript n is an integer of from 0 to 3; each $R^{1a}$ and $R^{1b}$ is a member independently selected from the group consisting of H, $C_{1-8}$ alkyl, $C_{1-8}$ haloalkyl, $C_{3-6}$ cycloalkyl, $—COR^a$, $—CO_2R^a$, $—CONR^aR^b$, $—NR^aR^b$, $—NR^aCOR^b$, $—OR^a$, $—X^1COR^a$, $—X^1CO_2R^a$, $—X^1CONR^aR^b$, $—X^1NR^aCOR^b$, $—X^1NR^aR^b$, and $—X^1OR^a$, wherein $X^1$ is a member selected from the group consisting of $C_{1-4}$ alkylene, and each $R^a$ and $R^b$ is independently selected from the group consisting of hydrogen, $C_{1-8}$ alkyl, $C_{1-8}$ haloalkyl, and $C_{3-6}$ cycloalkyl, and optionally two $R^{1a}$ groups on adjacent carbon atoms are joined to form a 5-, 6- or 7-membered carbocyclic or heterocyclic ring; each of $R^{2a}$ and $R^{2b}$ is a member independently selected from the group consisting of H, hydroxyl, $C_{1-8}$ alkyl, $C_{1-8}$ haloalkyl, $C_{1-8}$ alkoxy, $C_{1-4}$ alkoxy-$C_{1-4}$ alkyl, $C_{1-8}$ hydroxyalkyl, $C_{1-4}$ alkoxy-$C_{1-4}$ alkoxy, $C_{3-6}$ cycloalkyl, $C_{3-6}$ cycloalkyl-$C_{1-4}$ alkyl, 3- to 7-membered heterocycloalkyl, 3- to 7-membered heterocycloalkyl-$C_{1-4}$ alkyl, $—X^1CO_2R^a$, $—X^1CONR^aR^b$, $—X^1NR^aCOR^b$, $—X^1NR^aR^b$, wherein $X^1$, $R^a$ and $R^b$ are defined above.

The symbol $Ar^1$ represents a six- or ten-membered monocyclic or fused bicyclic aryl ring, or a five- to ten-membered monocyclic or fused bicyclic heteroaryl ring; each of which is substituted with from one to five substituents, $R^3$, $R^{3a}$, $R^{3b}$, $R^4$ and $R^{4a}$ which are independently selected from the group consisting of H, halogen, $—OR^c$, $—OC(O)R^c$, $—NR^cR^d$, $—SR^c$, $—R^c$, $—CN$, $—NO_2$, $—CO_2R^c$, $—CONR^cR^d$, $—C(O)R^c$, $—OC(O)NR^cR^d$, $—NR^dC(O)R^c$, $—NR^dC(O)_2R^c$, $—NR^c—C(O)NR^cR^d$, $—NH—C(NH_2)=NH$, $—NR^cC(NH_2)=NH$, $—NH—C(NH_2)=NR^c$, $—NH—C(NHR^c)=NH$, $—S(O)R^c$, $—S(O)_2R^c$, $—NR^cS(O)_2R^c$, $—S(O)_2NR^cR^d$, $—X^2OR^c$, $—O—X^2OR^c$, $—X^2OC(O)R^c$, $—X^2NR^cR^d$, $—O—X^2NR^cR^d$, $—X^2SR^c$, $—X^2CN$, $—X^2NO_2$, $—X^2CO_2R^c$, $—O—X^2CO_2R^c$, $—X^2CONR^cR^d$, $—O—X^2CONR^cR^d$, $—X^2C(O)R^c$, $—X^2OC(O)NR^cR^d$, $—X^2NR^dC(O)R^c$, $—X^2NR^dC(O)_2R^e$, $—X^2NR^cC(O)NR^cR^d$, $—X^2NH—C(NH_2)=NH$, $—X^2NR^eC(NH_2)=NH$, $—X^2NH—C(NH_2)=NR^e$, $—X^2NH—C(NHR^e)=NH$, $—X^2S(O)R^e$, $—X^2S(O)_2R^e$, $—X^2NR^cS(O)_2R^e$, $—X^2S(O)_2NR^cR^d$, $—X^2N_3$, $—NR^d—X^2OR^c$, $—NR^d—X^2NR^cR^d$, $—NR^d—X^2CO_2R^c$, and $—NR^d—X^2CONR^cR^d$, wherein each $X^2$ is a member independently selected from the group consisting of $C_{1-4}$ alkylene, and each $R^c$ and $R^d$ is independently selected from hydrogen, $C_{1-8}$ alkyl, $C_{1-8}$ hydroxyalkyl, $C_{1-8}$ haloalkyl and $C_{3-6}$ cycloalkyl, or optionally $R^c$ and $R^d$ when attached to the same nitrogen atom can be combined with the nitrogen atom to form a five or six-membered ring having from 0 to 2 additional heteroatoms as ring members; and each $R^e$ is independently selected from the group consisting of $C_{1-8}$ alkyl, $C_{1-8}$ hydroxyalkyl, $C_{1-8}$ haloalkyl and $C_{3-6}$ cycloalkyl.

The symbol $Ar^2$ represents a six- or ten-membered monocyclic or fused bicyclic aryl ring, or a five- to ten-membered monocyclic or fused bicyclic heteroaryl ring; each of which is substituted with from one to five substituents, $R^5$, $R^6$, $R^7$, $R^8$ and $R^9$, independently selected from the group consisting of H, halogen, $-OR^f$, $-OC(O)R^f$, $-NR^fR^g$, $-SR^f$, $-R^h$, $-CN$, $-NO_2$, $-CO_2R^f$, $-CONR^fR^g$, $-C(O)R^f$, $-OC(O)NR^fR^g$, $-NR^gC(O)R^f$, $-NR^gC(O)_2R^h$, $-NR^f-C(O)NR^fR^g$, $-NH-C(NH_2)=NH$, $-NR^hC(NH_2)=NH$, $-NH-C(NH_2)=NR^h$, $-NH-C(NHR^h)=NH$, $-S(O)R^h$, $-S(O)_2R^h$, $-NR^fS(O)_2R^h$, $-S(O)_2NR^fR^g$, $-NR^fS(O)_2NR^fR^g$, $-N_3$, $-X^3OR^f$, $-X^3OC(O)R^f$, $-X^3NR^fR^g$, $-X^3SR^f$, $-X^3CN$, $-X^3NO_2$, $-X^3CO_2R^f$, $-X^3CONR^fR^g$, $-X^3C(O)R^f$, $-X^3OC(O)NR^fR^g$, $-X^3NR^gC(O)R^f$, $-X^3NR^gC(O)_2R^h$, $-X^3NR^f-C(O)NR^fR^g$, $-X^3NH-C(NH_2)=NH$, $-X^3NR^hC(NH_2)=NH$, $-X^3NH-C(NH_2)=NR^h$, $-X^3NH-C(NHR^h)=NH$, $-X^3S(O)R^h$, $-X^3S(O)_2R^h$, $-X^3NR^fS(O)_2R^h$, $-X^3S(O)_2NR^fR^g$, $-Y$, $-X^3Y$, $-S(O)_2Y$, $-C(O)Y$, $-X^3N_3$, $-O-X^3OR^f$, $-O-X^3NR^fR^g$, $-O-X^3CO_2R^f$, $-O-X^3CONR^fR^g$, $-NR^g-X^3OR^f$, $-NR^g-X^3NR^fR^g$, $-NR^g-X^3CO_2R^f$, and $-NR^g-X^3CONR^fR^g$, wherein Y is a five or six-membered aryl, heteroaryl or heterocyclic ring, optionally substituted with from one to three substitutents selected from the group consisting of halogen, $-OR^f$, $OC(O)R^f$, $-NR^fR^g$, $-R^h$, $-SR^f$, $-CN$, $-NO_2$, $-CO_2R^f$, $-CONR^fR^g$, $-C(O)R^f$, $-NR^gC(O)R^f$, $-NR^gC(O)_2R^h$, $-S(O)R^h$, $-S(O)_2R^h$, $-NR^fS(O)_2R^h$, $-S(O)_2NR^fR^g$, $-X^3OR^f$, $X^3SR^f$, $-X^3CN$, $-X^3NO_2$, $-X^3CO_2R^f$, $-X^3CONR^fR^g$, $-X^3C(O)R^f$, $-X^3OC(O)NR^fR^g$, $-X^3NR^gC(O)R^f$, $-X^3NR^gC(O)_2R^h$, $-X^3NR^f-C(O)NR^fR^g$, $-X^3OC(O)R^f$, $-X^3S(O)R^h$, $-X^3S(O)_2R^h$, $-X^3NR^fR^g$, $-X^3NR^fS(O)_2R^h$, $-X^3S(O)_2NR^fR^g$, $-O-X^3OR^f$, $-O-X^3NR^fR^g$, $-O-X^3CO_2R^f$, $-O-X^3CONR^fR^g$, $-NR^g-X^3OR^f$, $-NR^g-X^3NR^fR^g$, $-NR^g-X^3CO_2R^f$, and $-NR^g-X^3CONR^fR^g$ and wherein each $X^3$ is independently selected from the group consisting of $C_{1-4}$ alkylene, and each $R^f$ and $R^g$ is independently selected from hydrogen, $C_{1-8}$ alkyl, $C_{1-8}$ hydroxyalkyl, $C_{1-8}$ haloalkyl and $C_{3-6}$ cycloalkyl, or when attached to the same nitrogen atom can be combined with the nitrogen atom to form a five or six-membered ring having from 0 to 2 additional heteroatoms as ring members, and each $R^h$ is independently selected from the group consisting of $C_{1-8}$ alkyl, $C_{2-8}$ alkenyl, $C_{2-8}$ alkynyl, $C_{1-8}$ hydroxyalkyl, $C_{1-8}$ haloalkyl and $C_{3-6}$ cycloalkyl; or when two of $R^5$, $R^6$, $R^7$, $R^8$ and $R^9$, are attached to adjacent ring vertices of $Ar^2$, are optionally combined to form a five or six membered ring having zero, one or two heteroatoms selected from O and N as ring members.

In some embodiments, the compounds of formula I are those in which $Ar^1$ is selected from the group consisting of phenyl, naphthyl, pyridyl, pyrazinyl, pyridazinyl, pyrimidinyl, triazinyl, quinolinyl, quinoxalinyl and purinyl, each of which is optionally substituted with $R^3$, $R^{3a}$, $R^{3b}$, $R^4$ and $R^{4a}$.

In other embodiments, the compounds of formula I are those in which $Ar^1$ is selected from the group consisting of phenyl, naphthyl and pyridyl, each of which is optionally substituted with $R^3$, $R^{3a}$, $R^{3b}$, $R^4$ and $R^{4a}$.

In still other embodiments, the compounds of formula I are those in which $Ar^2$ is selected from the group consisting of phenyl, pyrazolyl, imidazolyl, triazolyl, tetrazolyl, oxazolyl, isoxazolyl, oxadiazolyl, oxathiadiazolyl, pyrrolyl, thiazolyl, isothiazolyl, benzimidazolyl, benzoxazolyl, benzopyrazolyl, benzotriazolyl, pyrazolo[3,4-b]pyridine, pyrazolo[3,4-d]pyrimidine, imidazo[4,5-b]pyridine, imidazo[1,5-α]pyridine, and pyrrolo[2,3-b]pyridine, each of which is optionally substituted with $R^5$, $R^6$ and $R^7$.

In yet other embodiments, the compounds of formula I are those in which $Ar^2$ is selected from the group consisting of pyrazolyl, imidazolyl and triazolyl, each of which is substituted with $R^5$, $R^6$ and $R^7$.

In certain embodiments, the compounds of formula I are those in which $Ar^1$ is selected from the group consisting of phenyl, naphthyl and pyridyl, each of which is substituted with from one to five substituents, $R^3$, $R^{3a}$, $R^{3b}$, $R^4$ and $R^{4a}$; and $Ar^2$ is selected from the group consisting of pyrazolyl, imidazolyl and triazolyl, each of which is substituted with $R^5$, $R^6$ and $R^7$.

In selected embodiments, the compounds of formula I are those in which $Ar^1$ is phenyl, which is substituted with from one to five substituents, $R^3$, $R^{3a}$, $R^{3b}$, $R^4$ and $R^{4a}$, and $Ar^2$ is selected from the group consisting of pyrazolyl, imidazolyl, benzimidazolyl, benzopyrazolyl, pyrazolo[3,4-b]pyridine, pyrazolo[3,4-d]pyrimidine, imidazo[4,5-b]pyridine, imidazo[1,5-α]pyridine, and pyrrolo[2,3-b]pyridine, each of which is optionally substituted with $R^5$, $R^6$ and $R^7$.

Still other embodiments of the invention are the compounds of formulae Ia, Ia1, Ia2, Ib, Ic, Id, II, II, IIb, IIb1, IIb2, IIb2a, IIb2b, IIb2c, IIc, IIb3, IIb2d, IIb2e, IIb2f, III, IIIa, IIIb, IIIc, IIb1, IIIb1a, IIIb1b, IIIb1c, IIIb2, IIIb3a, IIIb3b, IIIb3c, IV, IVa, IVb, IVc, IVd, V, Va and Vb.

Accordingly, in some embodiments, the compounds are those of formula Ia:

(Ia)

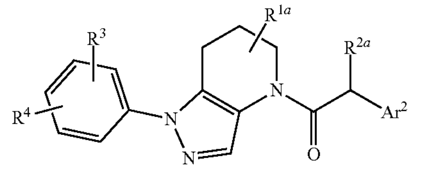

or a pharmaceutically acceptable salt, rotamer or optical isomer thereof, wherein $R^3$ and $R^4$ are independently selected from the group consisting of H, halogen, $-R^e$, $-CN$, and $-SO_2R^e$; and the groups $R^{1a}$, $R^{2a}$ and $Ar^2$ have the meanings provided with reference to formula I above, or the other embodiments provided.

In still other embodiments of formula I or Ia, $Ar^2$ is a heteroaryl group; in other embodiments, $Ar^2$ is a heteroaryl group, optionally substituted and attached to the remainder of the molecule through a nitrogen atom ring vertex; and in still other embodiments, $Ar^2$ has the formula:

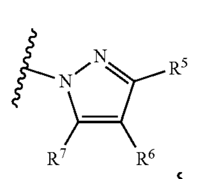

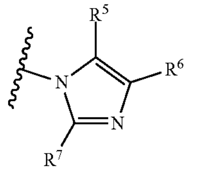

or

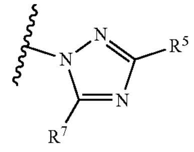

wherein $R^5$, $R^6$, and $R^7$ are independently selected from the group consisting of H, halogen, $-R^h$, $-CN$, $-SO_2R^h$, $-CO_2R^f$, $-CONR^fR^g$, and Y, wherein $-R^h$, $R^f$, $R^g$, and Y have the meanings provided above with respect to formula I.

In one group of selected embodiments, the compounds have the formula:

(Ia1)

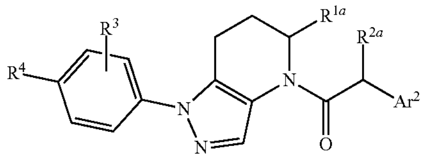

or a pharmaceutically acceptable salt, rotamer or optical isomer thereof, wherein $R^4$ is selected from the group consisting of F and Cl; and the groups $R^{1a}$, $R^{2a}$, $R^3$ and $Ar^2$ have the meanings provided with reference to formula I or Ia above, or the other embodiments provided.

In another group of selected embodiments, the compounds have the formula:

(Ia2)

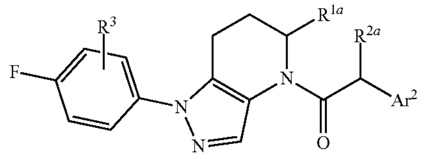

or a pharmaceutically acceptable salt, rotamer or optical isomer thereof, wherein $R^3$ is selected from the group consisting of H, halogen, $C_{1-8}$ alkyl, $C_{1-8}$ haloalkyl and $C_{1-8}$ alkoxy; $R^{10a}$ and $R^{2a}$ are independently selected from the group consisting of H, $C_{1-8}$ alkyl, $C_{1-8}$ haloalkyl, $C_{1-8}$ alkoxy and $C_{1-8}$ hydroxyalkyl; and $Ar^2$ has the meaning provided with reference to formula I or Ia above, or the embodiments provided.

In yet another group of selected embodiments, the compounds have the formula:

(Ib)

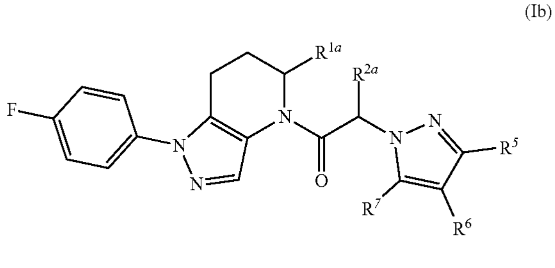

or a pharmaceutically acceptable salt, rotamer or optical isomer thereof, wherein $R^{1a}$ and $R^{2a}$ are independently selected from the group consisting of H, $C_{1-8}$ alkyl, $C_{1-8}$ haloalkyl, $C_{1-8}$ alkoxy and $C_{1-8}$ hydroxyalkyl; and $R^5$, $R^6$, and $R^7$ are independently selected from the group consisting of H, halogen, $—R^h$, —CN, $—SO_2R^h$, $—CO_2R^f$, $—CONR^fR^g$, and Y; wherein $—R^h$, $R^f$, $R^g$, and Y have the meanings provided above with respect to formula I.

In still another group of selected embodiments, the compounds have the formula:

(Ic)

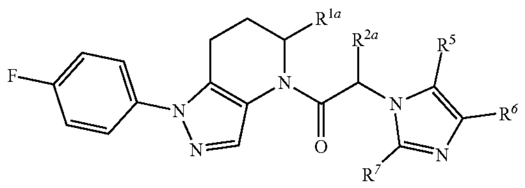

or a pharmaceutically acceptable salt, rotamer or optical isomer thereof, wherein $R^{1a}$ and $R^{2a}$ are independently selected from the group consisting of H, $C_{1-8}$ alkyl, $C_{1-8}$ haloalkyl, $C_{1-8}$ alkoxy and $C_{1-8}$ hydroxyalkyl; and $R^5$, $R^6$, and $R^7$ are independently selected from the group consisting of H, halogen, $—R^h$, —CN, $—SO_2R^h$, $—CO_2R^f$, $—CONR^fR^g$, and Y; wherein $—R^h$, $R^f$, $R^g$, and Y have the meanings provided above with respect to formula I.

In another group of selected embodiments, the compounds have the formula:

(Id)

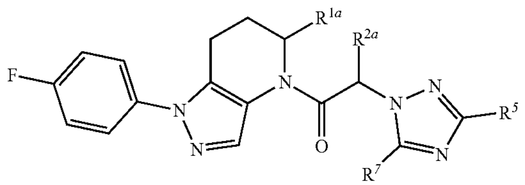

or a pharmaceutically acceptable salt, rotamer or optical isomer thereof, wherein $R^{1a}$ and $R^{2a}$ are each independently selected from the group consisting of H, $C_{1-8}$ alkyl, $C_{1-8}$ haloalkyl, $C_{1-8}$ alkoxy, and $C_{1-8}$ hydroxyalkyl; and $R^5$ and $R^7$ are each independently selected from the group consisting of H, halogen, $—R^h$, —CN, $—SO_2R^h$, $—CO_2R^f$, $—CONR^fR^g$, and Y; wherein $—R^h$, $R^f$, $R^g$, and Y have the meanings provided above with respect to formula I.

For any of the embodiments above, when Y is present, selected embodiments are those in which Y is selected from the group consisting of pyridyl, pyrimidinyl, imidazolyl, oxazolyl, oxadiazolyl, triazolyl, thiazolyl, imidazolinyl and pyrazolyl.

In some embodiments, the CCR1 antagonist is a compound selected from 1.001

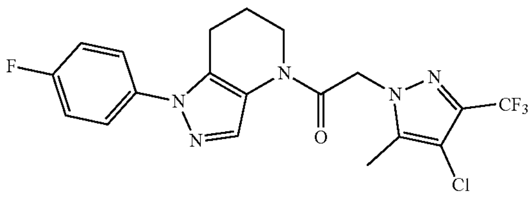

1.002

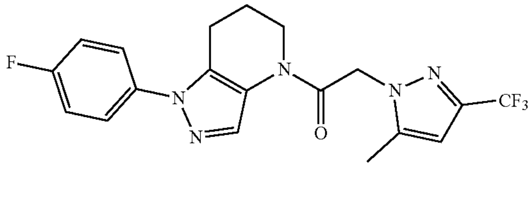

-continued 1.003

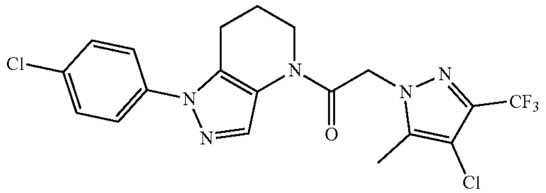

1.004

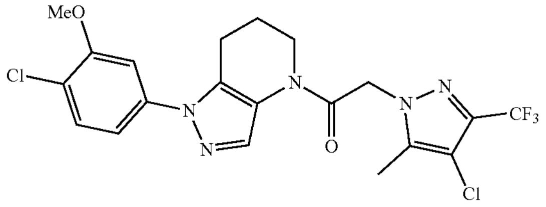

1.005

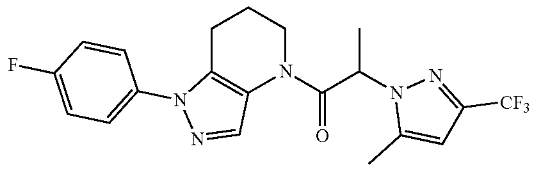

1.006

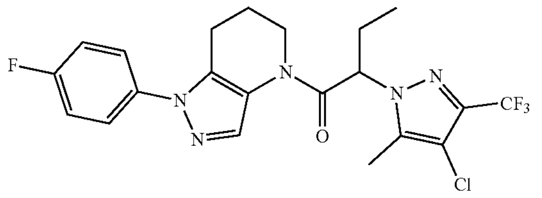

1.007

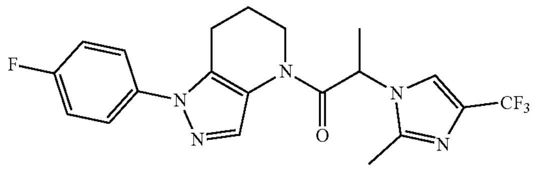

1.008

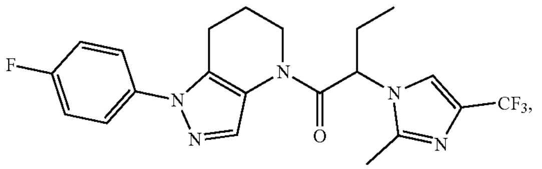

or a pharmaceutically acceptable salt thereof.

In a particular embodiment, the CCR1 antagonist is the compound 1.001,

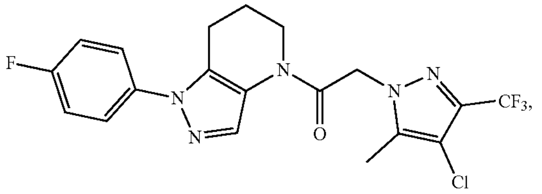 [SMILES: Cc1c(Cl)c(C(F)(F)F)nn1CC(=O)N1CCCc2c1cnn2-c1ccc(F)cc1]

or a pharmaceutically acceptable salt thereof.

In still other embodiments, the CCR1 antagonist is a compound of Formula II:

(II)

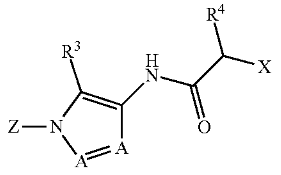

or pharmaceutically acceptable salt, hydrate, solvate, N-oxide or rotamer thereof. In Formula II, each A is independently selected from the group consisting of N and CH; X and Z are each independently selected from the group consisting (i) monocyclic or fused-bicyclic aryl and heteroaryl, wherein the heteroaryl group has from 1-4 heteroatoms as ring members selected from N, O and S;

(ii) monocyclic four-, five-, six- or seven-membered ring selected from the group consisting of cycloalkane, and heterocycloalkane, wherein the heterocycloalkane rings have from 1-3 heteroatoms as ring members selected from N, O and S;

wherein each of the rings in (i) and (ii) are optionally substituted with from 1 to 5 substituents selected from halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$SO_2R^a$, —$NR^aR^b$, —$CONR^aR^b$, aryl, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and hetereocycloalkane portions of the substituents are optionally further substituted with 1-3 $R^a$; and optionally, two substituents on adjacent ring vertices are connected to form an additional 5- or 6-membered ring which is saturated, unsaturated or aromatic having ring vertices selected from C, O, N and S;

$R^3$ is a member selected from the group consisting of H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$NR^aR^b$, —$CONR^aR^b$, aryl, 5- or 6-membered heteroaryl, and 3-, 4-, 5- or 6-membered heterocyclic wherein the heteroatoms present as ring vertices of the heteroaryl and heterocyclic rings are selected from N, O and S, and wherein the alkyl, cycloalkyl, aryl, heteroaryl and hetereocyclic portions of $R^3$ are optionally further substituted with 1-3 $R^a$;

$R^4$ is a member selected from the group consisting of H, —$OR^a$ and $C_{1-8}$ alkyl optionally substituted with —$OR^a$ or —$NR^aR^b$; or $R^4$ is combined with X to form a bicyclic fused ring system; and each $R^a$ and $R^b$ is independently selected from the group consisting of hydrogen, hydroxyl, halogen, cyano, $C_{1-8}$alkyl, $C_{1-8}$ alkoxy, $C_{1-8}$haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and —$SO_2$—$C_{1-8}$ alkyl.

One of skill in the art will appreciate that substituent recitations only refer to those that are generally stable (e.g., less than 20% degradation on storage), such that the group —OR$^a$ is not meant to include those components wherein R$^a$ is alkoxy (which would furnish a peroxy or —OO-alkyl group).

In some selected embodiments, the compounds of Formula II are represented by Formula IIa:

(IIa)

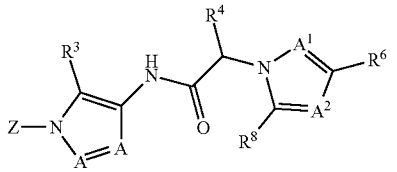

wherein A$^1$ is N or C(R$^5$); A$^2$ is N or C(R$^7$); and R$^5$, R$^6$, R$^7$ and R$^8$ are each independently selected from H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —OR$^a$, —CO$_2$R$^a$, —NR$^a$R$^b$, —CONR$^a$R$^b$, aryl, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and hetereocycloalkane portions of R$^5$, R$^6$, R$^7$ and R$^8$ are optionally further substituted with 1-3 R$^a$; and optionally, and optionally, R$^4$ and R$^5$, R$^4$ and R$^8$, or adjacent members of R$^5$, R$^6$, R$^7$ and R$^8$ are connected to form an additional 5- or 6-membered ring which is saturated, unsaturated or aromatic having ring vertices selected from C, O, N and S; or a pharmaceutically acceptable salt, hydrate, solvate, rotamer or N-oxide thereof.

In other selected embodiments, the compounds of Formula IIa are those wherein R$^8$ is other than H.

In other selected embodiments, the compounds of Formula IIa are represented by Formula IIb:

(IIb)

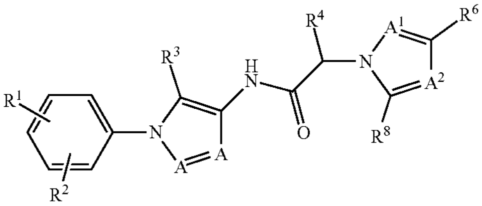

wherein R$^1$ and R$^2$ are each independently selected from H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —OR$^a$, —CO$_2$R$^a$, —SO$_2$R$^a$, —NR$^a$R$^b$, —CONR$^a$R$^b$, and 3-, 4-, 5- or 6-membered heterocycloalkane wherein the heteroatoms present as ring vertices of the heterocycloalkane ring are selected from N, O and S, and wherein the alkyl, cycloalkyl and hetereocycloalkane portions of R$^1$ and R$^2$ are optionally further substituted with 1-3 R$^a$.

In selected embodiments of Formula IIb, each R$^1$ and R$^2$ is independently selected from H, halogen, CN, $C_{1-8}$ alkyl, $C_{1-8}$ haloalkyl, —CO$_2$R$^a$ and —SO$_2$R$^a$.

In other selected embodiments for the compounds of Formula IIb, the compounds are represented by the structure:

(IIb1)

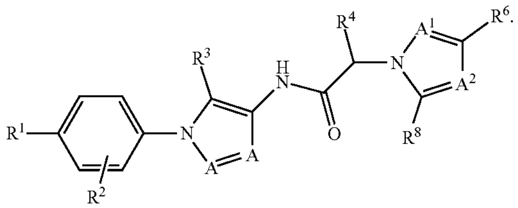

In other selected embodiments for the compounds of Formula IIb and IIb1, the ring portion having N, A$^1$ and A$^2$ as ring vertices is selected from:

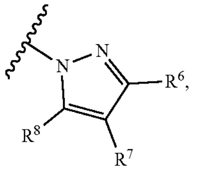

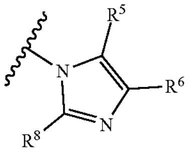

and

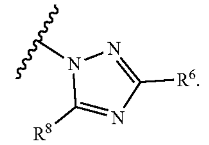

In still other selected embodiments for the compounds of Formula IIb and IIb1, the ring portion having N, A$^1$ and A$^2$ as ring vertices is selected from:

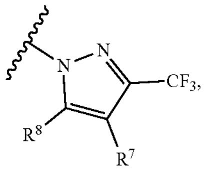

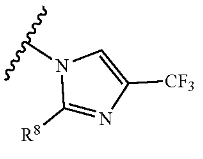

and

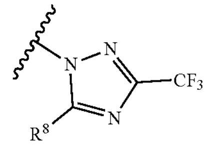

wherein R$^7$ is H or Cl, and R$^8$ is $C_{1-8}$ alkyl optionally substituted with 1 or 2 R$^a$.

In still other selected embodiments of Formula IIb or IIb1, R$^4$ is H or CH$_3$.

Returning to Formula II, some selected embodiments are those compounds represented by Formula IIb2:

(IIb2)

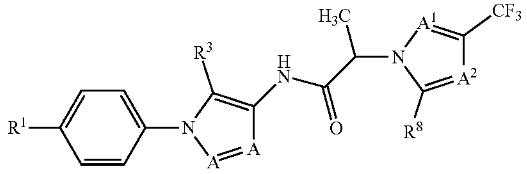

wherein $R^1$ is Cl or F; $R^3$ is selected from the group consisting of $C_{1-8}$ alkyl, $C_{1-8}$ haloalkyl, $C_{1-8}$ hydroxyalkyl, wherein the alkyl portions of $R^3$ are optionally further substituted with 1-3 $R^a$; and wherein $R^7$ and $R^8$ are not joined to form a ring In still other selected embodiments, the compounds of Formula II, IIb, IIb1 and IIb2 are represented by Formulae IIb2a, IIb2b and IIb2c.

(IIb2a)

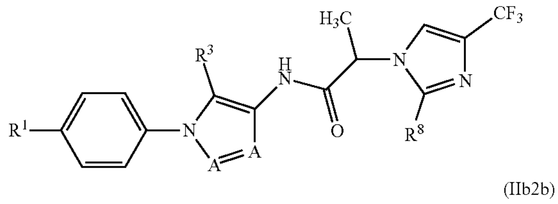

(IIb2b)

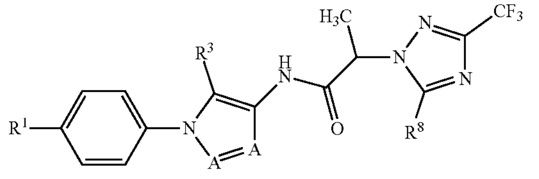

(IIb2c)

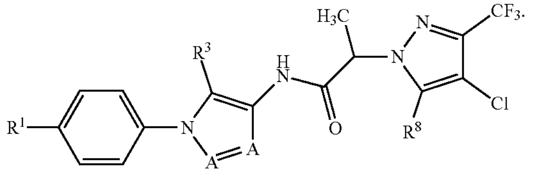

In some selected embodiments, the compounds are represented by Formula IIc:

(IIc)

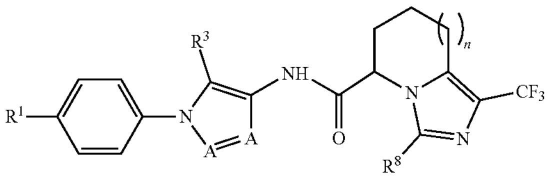

wherein the subscript n is 0 or 1.

In some selected embodiments, the compounds are represented by Formula IIb3:

(IIb3)

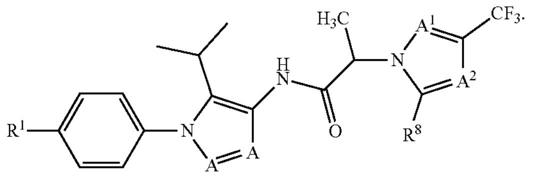

In some selected embodiments of Formula IIb, the compounds are represented by Formulae IIb2d, IIb2e and IIb2f.

(IIb2d)

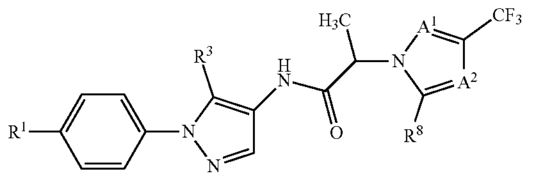

(IIb2e)

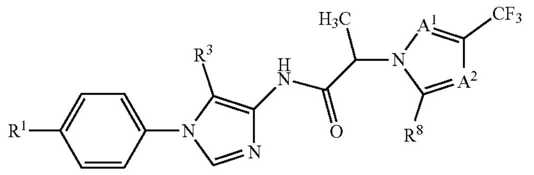

(IIb2f)

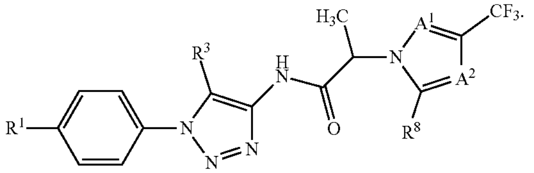

In selected embodiments of any of Formulae II, IIa, IIb, IIb1, IIb2, IIb2a, IIb2b, IIb2c, IIb2d, IIb2e, IIb2f, IIb3 and IIc, $R^3$ is $C_{1-8}$ alkyl.

In other embodiments, CCR1 antagonists that are useful in the methods and compositions herein are represented by Formula III:

(III)

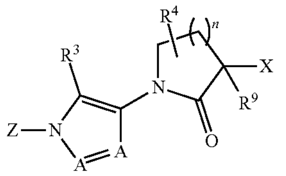

or pharmaceutically acceptable salt, hydrate, solvate, N-oxide or rotamer thereof. In Formula III, the letter n is an integer of from 0 to 3;

each A is independently selected from the group consisting of N and CH;

X and Z are each independently selected from the group consisting (i) monocyclic or fused-bicyclic aryl and heteroaryl, wherein the heteroaryl group has from 1-4 heteroatoms as ring members selected from N, O and S;

(ii) monocyclic four-, five-, six- or seven-membered ring selected from the group consisting of cycloalkane, and heterocycloalkane, wherein the heterocycloalkane rings have from 1-3 heteroatoms as ring members selected from N, O and S;

wherein each of the rings in (i) and (ii) are optionally substituted with from 1 to 5 substituents selected from halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, $—OR^a$, $—CO_2R^a$, $—SO_2R^a$, $—NR^aR^b$, $—CONR^aR^b$, aryl, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and hetereocycloalkane portions of the substituents are optionally further substituted with 1-3 $R^a$; and optionally, two substituents on adjacent ring vertices are connected to form an additional 5- or 6-membered ring which is saturated, unsaturated or aromatic having ring vertices selected from C, O, N and S;

$R^3$ is a member selected from the group consisting of H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$NR^aR^b$, —$CONR^aR^b$, aryl, 5- or 6-membered heteroaryl, and 3-, 4-, 5- or 6-membered heterocyclic wherein the heteroatoms present as ring vertices of the heteroaryl and heterocyclic rings are selected from N, O and S, and wherein the alkyl, cycloalkyl, aryl, heteroaryl and hetereocyclic portions of $R^3$ are optionally further substituted with 1-3 $R^a$;

$R^4$ is a member selected from the group consisting of H, —$OR^a$ and $C_{1-8}$ alkyl optionally substituted with —$OR^a$;

$R^9$ is a member selected from the group consisting of H and $C_{1-8}$ alkyl optionally substituted with —$OR^a$;

each $R^a$ and $R^b$ is independently selected from the group consisting of hydrogen, hydroxyl, halogen, cyano, $C_{1-8}$ alkyl, $C_{1-8}$ alkoxy, $C_{1-8}$haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and —$SO_2$—$C_{1-8}$ alkyl.

In some selected embodiments, the compounds of Formula III are represented by Formula IIIa:

(IIIa)

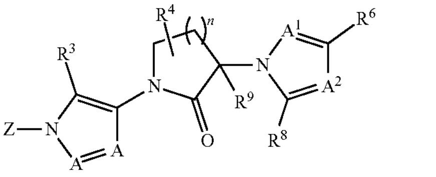

wherein $A^1$ is N or $C(R^5)$; $A^2$ is N or $C(R^7)$; and $R^5$, $R^6$, $R^7$ and $R^8$ are each independently selected from H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$NR^aR^b$, —$CONR^aR^b$, aryl, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and hetereocycloalkane portions of $R^5$, $R^6$, $R^7$ and $R^8$ are optionally further substituted with 1-3 $R^a$; and optionally, adjacent members of $R^5$, $R^6$, $R^7$ and $R^8$ are connected to form an additional 5- or 6-membered ring which is saturated, unsaturated or aromatic having ring vertices selected from C, O, N and S; or a pharmaceutically acceptable salt, hydrate, solvate, rotamer or N-oxide thereof.

In other selected embodiments, the compounds of Formula IIIa are those wherein $R^8$ is other than H.

In other selected embodiments, the compounds of Formula IIIa are represented by Formula IIIb:

(IIIb)

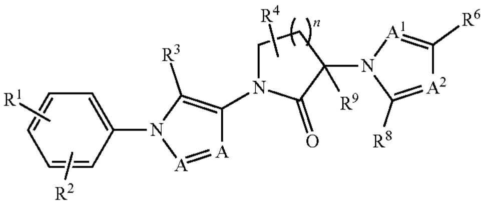

wherein $R^1$ and $R^2$ are each independently selected from H, halogen, CN, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —$SO_2R^a$, —$NR^aR^b$, —$CONR^aR^b$, and 3-, 4-, 5- or 6-membered heterocycloalkane wherein the heteroatoms present as ring vertices of the heterocycloalkane ring are selected from N, O and S, and wherein the alkyl, cycloalkyl and hetereocycloalkane portions of $R^1$ and $R^2$ are optionally further substituted with 1-3 $R^a$.

In selected embodiments of Formula IIIb, each $R^1$ and $R^2$ is independently selected from H, halogen, CN, $C_{1-8}$ alkyl, $C_{1-8}$ haloalkyl, —$CO_2R^a$ and —$SO_2R^a$.

In other selected embodiments for the compounds of Formula IIIb, the ring portion having N, $A^1$ and $A^2$ as ring vertices is selected from:

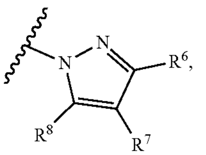

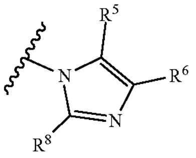

and

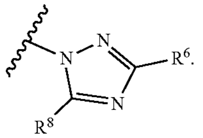

In still other selected embodiments for the compounds of Formula IIIb, the ring portion having N, $A^1$ and $A^2$ as ring vertices is selected from:

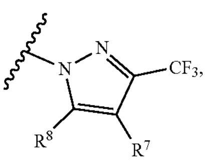

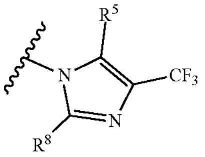

and

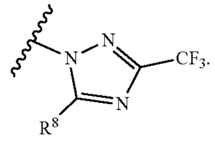

wherein $R^7$ is H or Cl, and $R^8$ is $C_{1-8}$ alkyl optionally substituted with 1 or 2 $R^a$.

In still other selected embodiments of Formula IIIb, $R^9$ is H or $CH_3$.

Returning to Formula III, some selected embodiments are those compounds represented by Formula IIIc:

(IIIc)

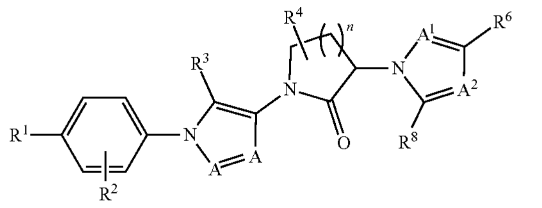

wherein the letter n is 1, 2 or 3. Other selected embodiments are those wherein n is 1.

In still other selected embodiments, the compounds of Formula IIIb are those represented by Formula IIIb1:

(IIIb1)

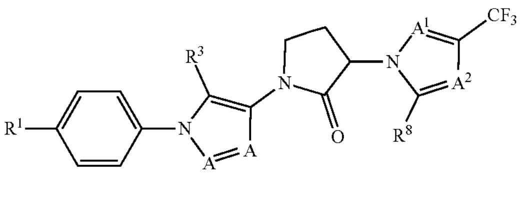

wherein $R^1$ is Cl or F.

In still other selected embodiments, the compounds of Formula IIIb1 are represented by Formulae IIIb1a, IIIb1b and IIIb1c.

(IIIb1a)

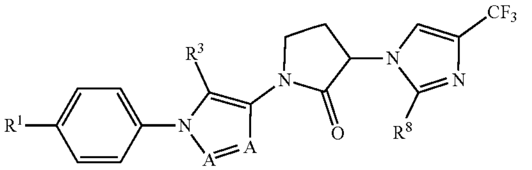

(IIIb1b)

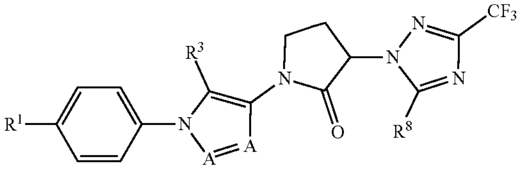

(IIIb1c)

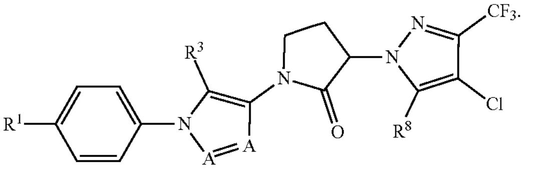

In some selected embodiments of Formula IIIb, the compounds are represented by Formula IIIb2:

(IIIb2)

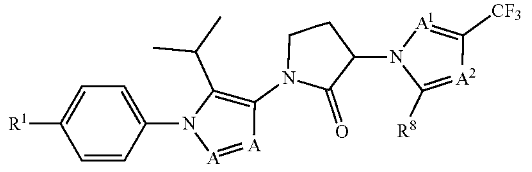

wherein $R^1$ is Cl or F.

In some selected embodiments of Formula IIIb, the compounds are represented by Formulae IIIb3a, IIIb3b and IIIb3c.

(IIIb3a)

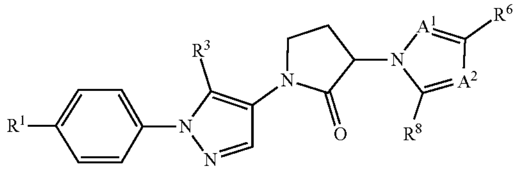

(IIIb3b)

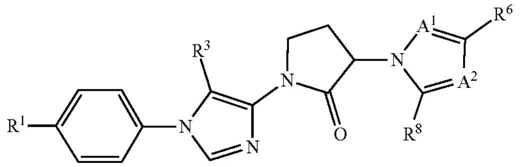

(IIIb3c)

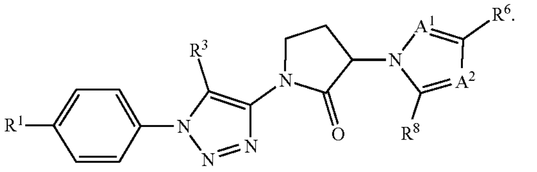

In selected embodiments of any of Formulae III, IIIa, IIIb, IIIc, IIIb1, IIIb1a, IIIb1b, IIIb1c, IIIb2, IIIb3a, IIIb3b and IIIb3c, $R^3$ is selected from H, $C_{1-8}$ alkyl, $C_{3-8}$ cycloalkyl and $C_{2-8}$ alkenyl.

In some selected embodiments, the CCR1 antagonist is selected from:

3.001

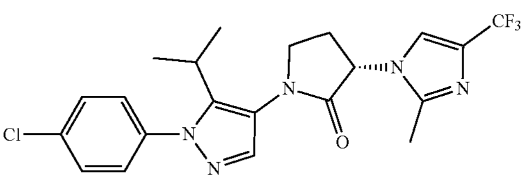

and 3.002

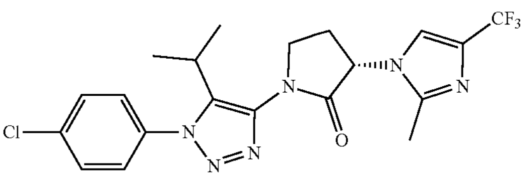

In some selected embodiments, the CCR1 antagonist is:

3.001

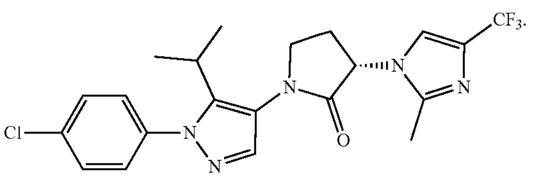

In some selected embodiments, the CCR1 antagonist is:

3.002

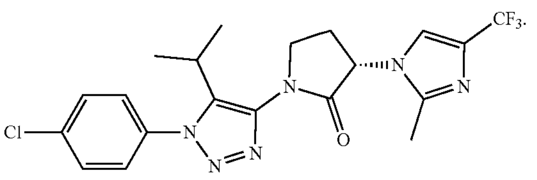

In other embodiments, CCR1 antagonists that are useful in the methods and compositions herein are represented by Formula IV:

(IV)

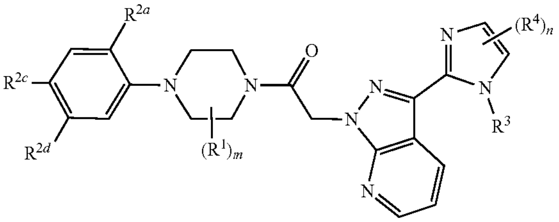

or pharmaceutically acceptable salt, hydrate or N-oxide thereof. In Formula IV, $R^1$ is $C_{1-4}$ alkyl or $C_{1-4}$ haloalkyl, and the subscript m is an integer from 0 to 1. In Formula IV, $R^{2a}$, $R^{2c}$, $R^{2d}$ are each a member independently selected from the group consisting of hydrogen, halogen, $C_{1-4}$ alkoxy, $C_{1-4}$ alkyl, —O—$C_{1-4}$ haloalkyl and $C_{1-4}$ haloalkyl; $R^3$ is a member selected from the group consisting of hydrogen and $C_{1-4}$ alkyl; and $R^4$ is $C_{1-4}$ alkyl, and the subscript n is an integer from 0-2. In one embodiment, $R^3$ is hydrogen.

In another embodiment, $R^3$ is hydrogen and the subscript n is 0.

In another embodiment, $R^1$ in Formula IV is methyl, trifluoromethyl or ethyl and the subscript m is 1.

In another embodiment the subscript m is 0.

In yet another embodiment, $R^{2a}$, $R^{2c}$, and $R^{2d}$ are each independently selected from the group consisting of fluoro, chloro, bromo, iodo, methoxy, ethoxy, trifluoromethoxy, methyl, ethyl, trifluoromethyl and 2-fluoroethoxy.

In yet another embodiment, $R^{2a}$ is hydrogen and $R^{2c}$ and $R^{2d}$ are each independently selected from the group consisting of fluoro, chloro, bromo, iodo, methoxy, ethoxy, trifluoromethoxy, methyl, ethyl, trifluoromethyl and 2-fluoroethoxy.

In one preferred embodiment, the CCR1 anagonists are of Formula IVa or IVb.

IVa

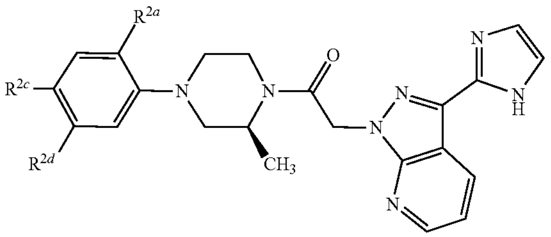

IVb

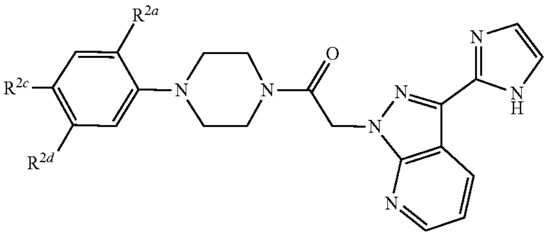

In one embodiment, $R^{2a}$ and $R^{2c}$ in Formula IVa or IVb, are each independently selected from the group consisting of fluoro, chloro, bromo and iodo; and $R^{2d}$ is selected from the group consisting of methoxy, ethoxy, trifluoromethoxy, methyl, ethyl, trifluoromethyl and 2-fluoroethoxy.

In a specific embodiment, compounds of Formula IVa or IVb are selected from the group consisting of:

4.001

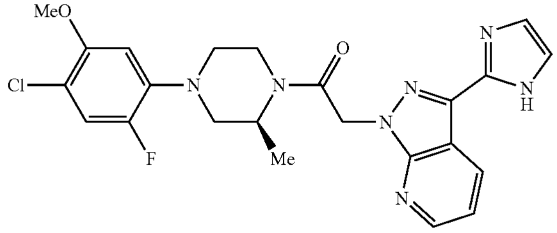

, 4.002

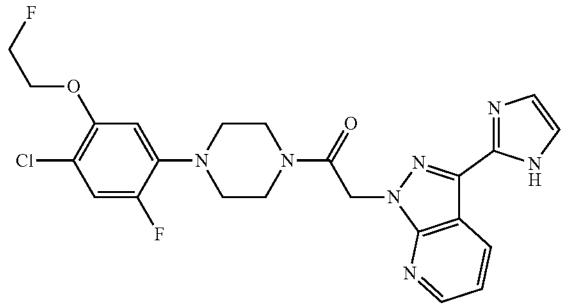

4.003

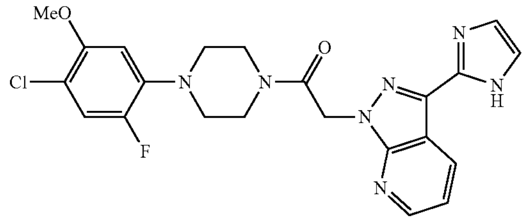

and

-continued 4.004

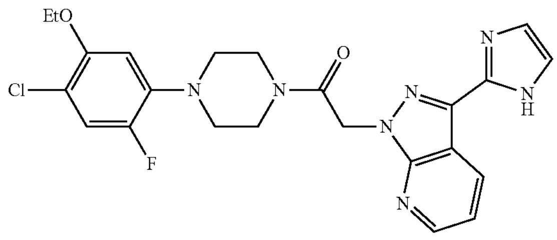

.

In another specific embodiment, the compounds of the invention are of Formula IVc or IVd:

IVc

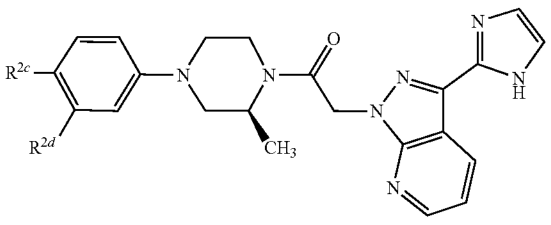

IVd

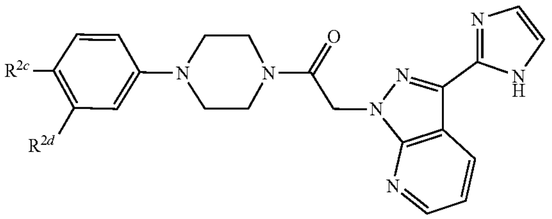

;

In Formula IVc and IVd, in certain embodiments, $R^{2c}$ is selected from the group consisting of fluoro, chloro, bromo and iodo; and $R^{2d}$ is selected from the group consisting of methoxy, ethoxy, trifluoromethoxy, methyl, ethyl, trifluoromethyl and 2-fluoroethoxy.

In a specific embodiment, compounds of Formula IVc or IVd are selected from the group consisting of:

4.005

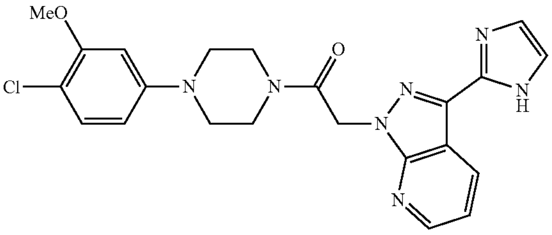

,

-continued 4.006

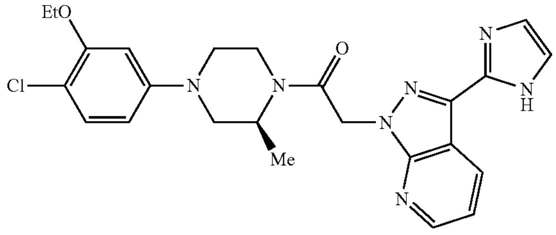

, 4.007

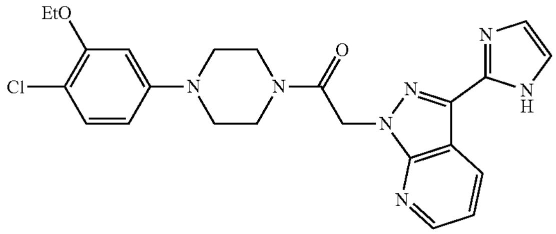

, 4.008

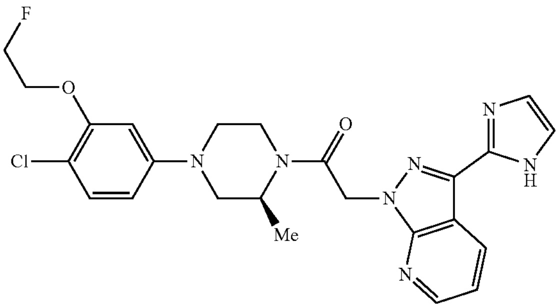

, 4.009

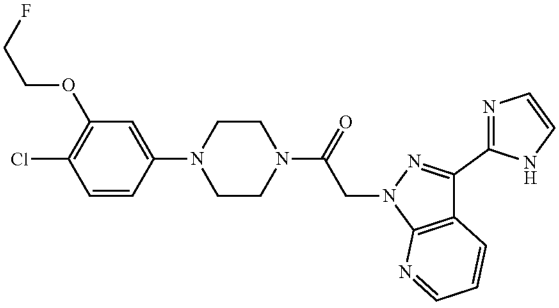

, 4.010

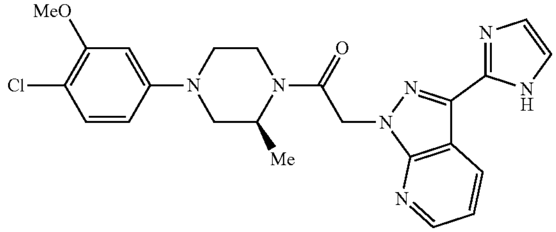

,

-continued 4.011

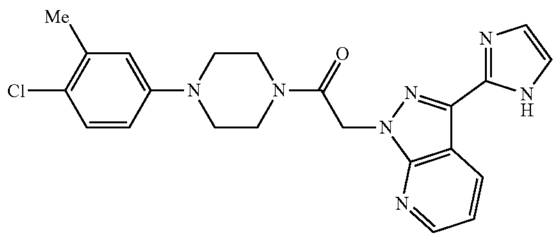

, 4.012

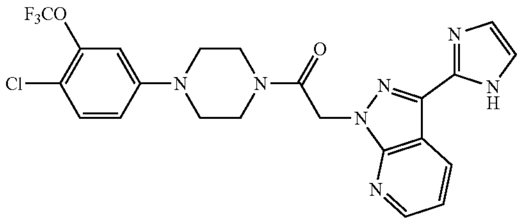

and 4.013

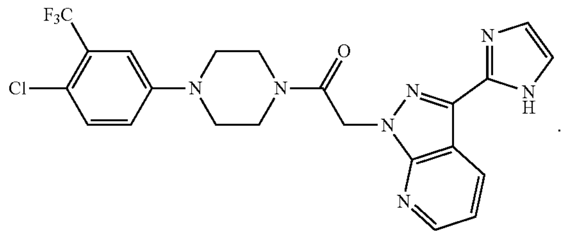

.

In yet another embodiment of the invention, the compound of Formula IVd has the following structure:

4.005

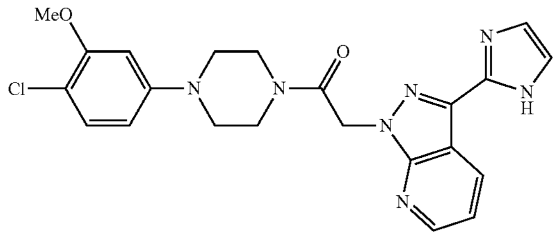

.

In other embodiments, CCR1 antagonists that are useful in the methods and compositions herein are represented by Formula V:

(V)

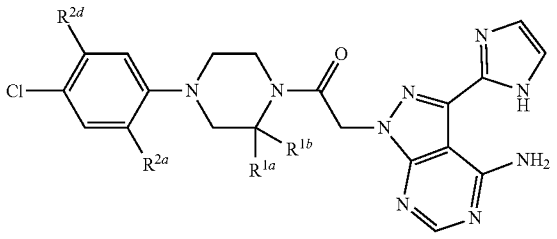

or pharmaceutically acceptable salts, hydrates or N-oxides thereof. In Formula V, $R^{1a}$ and $R^{1b}$ are each independently selected from the group consisting of H and $CH_3$; $R^{2a}$ is selected from the group consisting of H and F; and $R^{2d}$ is selected from the group consisting of H, $C_{1-4}$ alkoxy and $C_{1-4}$ haloalkoxy. In one embodiment, $R^{2a}$ is hydrogen.

In another embodiment, $R^{1a}$ and $R^{1b}$ are each H.

In another embodiment, $R^{1b}$ is methyl and $R^{1a}$ is H.

In yet another embodiment, $R^{1a}$ and $R^{1b}$ are each methyl.

In still another embodiment, $R^{2a}$ is hydrogen and $R^{2d}$ is selected from the group consisting of methoxy, ethoxy and trifluoromethoxy.

In one preferred embodiment, the compounds are of Formula Va or Vb:

Va

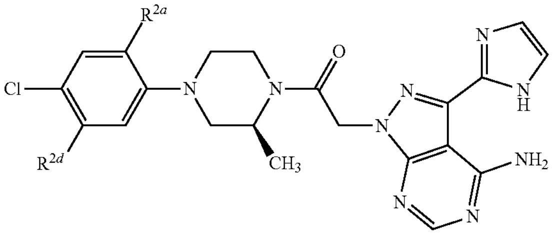

Vb

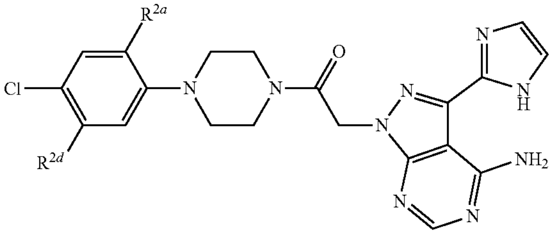

wherein $R^{2a}$ is selected from the group consisting of H and F; and $R^{2d}$ is selected from the group consisting of methoxy, ethoxy and trifluoromethoxy.

In a specific embodiment, CCR1 antagonist compounds are selected from the group consisting of:

5.001

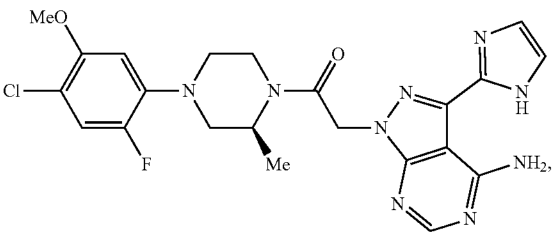

5.002

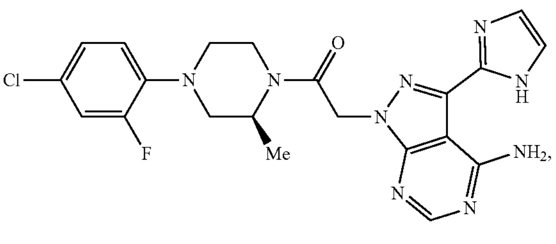

-continued
5.003
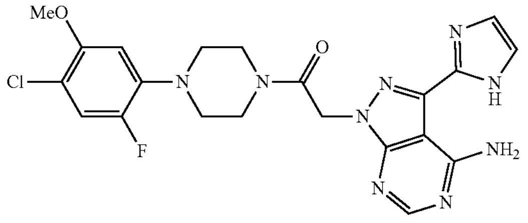
and
5.004
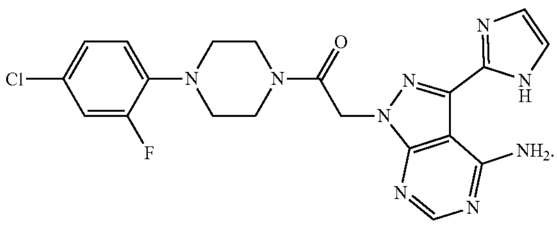
In another specific embodiment, the CCR1 antagonist compounds are selected from the group consisting of:
5.005
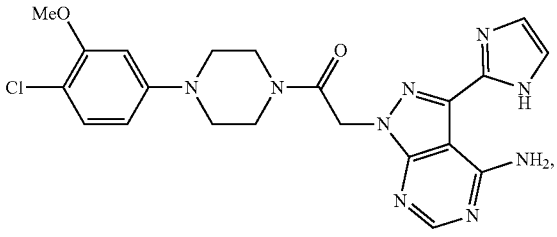
5.006
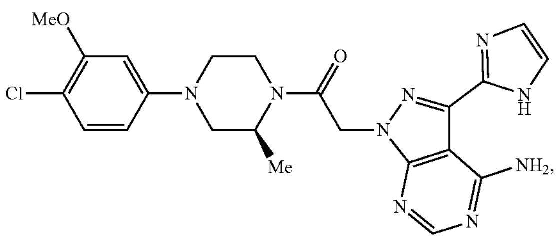
5.007
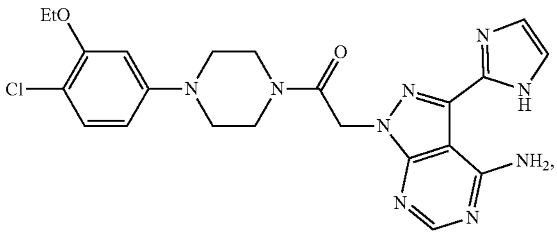
-continued
5.008
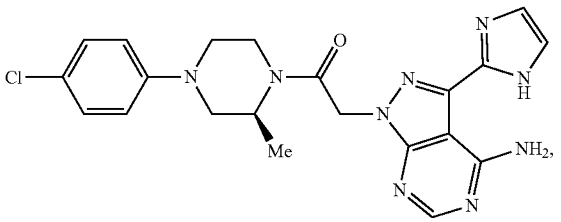
5.009
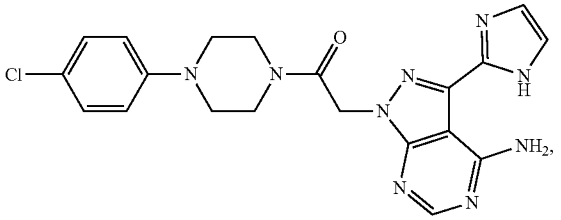
5.010
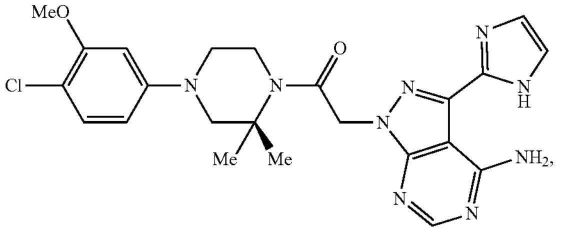
5.011
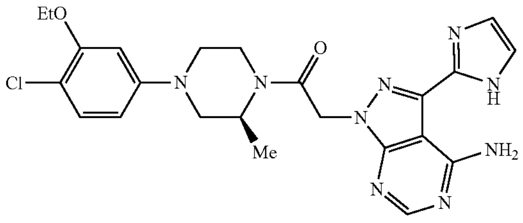
and
5.012
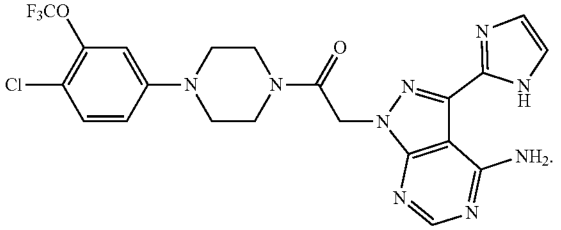
In yet another embodiment, the CCR1 antagonist compound has the structure 5.005:

5.005

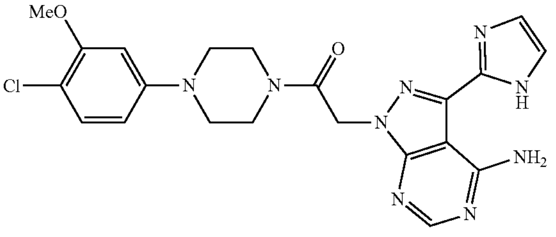

or a pharmaceutically acceptable salt thereof.

In some embodiments, the CCR1 chemokine receptor antagonist is selected from the group consisting of BL-5923, UCB-35625, BX-471, BI-638683, PS-031291, MLN-3701, AZD-4818, MLN-3897, CP-481715, F-18-CCR1, AOP-RANTES, PS-375179, and NSC-651016.

B. PD-1 Inhibitors and PD-L1 Inhibitors

The methods, compositions, and kits provided herein include immune checkpoint inhibitors such as PD-1/PD-L1 pathway inhibitors (agents).

In some embodiments, the PD-1 pathway inhibitor can be a PD-1 antagonist, PD-1 binding antagonist, small molecule PD-1 antagonist, PD-1 inhibitor, anti-PD-1 biological product (e.g., an antibody or fragment thereof that specifically binds to PD-1), PD-L1 antagonist, small molecule PD-L1 antagonist, PD-L1 binding antagonist, PD-L1 inhibitor, anti-PD-L1 biological product (e.g., an antibody or fragment thereof that specifically binds to PD-L1), and the like.

In some embodiments, a PD-L1 inhibitor can be durvalumab or atezolizumab or avelumab or BMS-936559 (MDX-1105) or ALN-PDL or TSR-042 or KD-033 or CA-170 or CA-327 or STI-1014 or MEDI-0680 or KY-1003.

In some embodiments, a PD-L1 inhibitor can be durvalumab or atezolizumab or avelumab or BMS-936559 (MDX-1105) or ALN-PDL or TSR-042 or KD-033 or CA-170 or STI-1014 or MEDI-0680 or KY-1003. Durvalumab (MEDI4736) is a human monoclonal antibody directed against PD-L1. Atrexolizumab (MPDL3280A) is a fully humanized, engineered IgG1 monoclonal antibody against PD-L1. Avelumab (MSB0010718C) is a fully humanized, engineered IgG1 monoclonal antibody against PD-L1. BMS-936559 (MDX-1105) is a fully human IgG4 monoclonal antibody against PD-L1. ALN-PDL is an inhibitory RNA (RNAi) targeting PD-L1. TSR-042 refers to an engineered chimeric antibody that is directed against the PD-1/PD-L1 pathway. KD-033 refers to a bifunctional anti-PD-L1/IL-15 fusion protein wherein the anti-PD-L1 antibody is linked at its tail to the cytokine IL-15 by the sushi domain of the IL-15 receptor. CA-170 refers to a small molecule antagonist of PD-L1 and VISTA. STI-1014 refers to an anti-PD-L1 antibody. KY-1003 is a monoclonal antibody against PD-L1. CA-327 refers to a small molecule antagonist of PD-L1 and TIM3.

In some embodiments, the PD-1 and/or PD-L1 inhibitor is selected from the group consisting of durvalumab, atezolizumab, pembrolizumab, nivolumab, AP-106, AP-105, MSB-2311, CBT-501, avelumab, AK-105, IO-102, IO-103, PDR-001, CX-072, SHR-1316, JTX-4014, GNS-1480, recombinant humanized anti-PD1 mAb (Shanghai Junshi Biosciences), REGN-2810, pelareorep, SHR-1210, PD1/PDL1 inhibitor vaccine (THERAVECTYS), BGB-A317, recombinant humanized anti-PD-1 mAb (Bio-Thera Solutions), Probody targeting PD-1 (CytomX), XmAb-20717, FS-118, PSI-001, SN-PDL01, SN-PD07, PD-1 modified TILs (Sangamo Therapeutics), PRS-332, FPT-155, jienuo mAb (Genor Biopharma), TSR-042, REGN-1979, REGN-2810, resminostat, FAZ-053, PD-1/CTLA-4 bispecific antibody (MacroGenics), MGA-012, MGD-013, M-7824, PD-1 based bispecific antibody (Beijing Hanmi Pharmaceutical), AK-112, AK-106, AK-104, AK-103, BI-754091, ENUM-244C8, MCLA-145, MCLA-134, anti-PD1 oncolytic monoclonal antibody (Transgene SA), AGEN-2034, IBI-308, WBP-3155, JNJ-63723283, MEDI-0680, SSI-361, CBT-502, anti-PD-1 bispecific antibody, dual targeting anti-PD-1/LAG-3 mAbs (TESARO), dual targeting anti-PD-1/TIM-3 mAbs (TESARO), PF-06801591, LY-3300054, BCD-100, STI-1110, pembrolizumab biosimilar, nivolumab biosimilar, PD-L1-TGF-beta therapy, KY-1003, STI-1014, GLS-010, AM-0001, GX-P2, KD-033, PD-L1/BCMA bispecific antibody (Immune Pharmaceuticals), PD-1/Ox40 targeting bispecific antibody (Immune Pharmaceuticals), BMS-936559, anti-PD-1NEGF-A DARPins (Molecular Partners), mDX-400, ALN-PDL, PD-1 inhibitor peptide (Aurigene), siRNA loaded dendritic cell vaccine (Alnylam Pharmaceuticals), GB-226, PD-L1 targeting CAR-TNK-based immunotherapy (TNK Therapeutics/NantKwest), INSIX RA, INDUS-903, AMP-224, anti-CTLA-4/anti-PD-1 bispecific humanized antibody (Akeso Biopharma), B7-H1 vaccine (State Key Laboratory of Cancer Biology/Fourth Military Medical University), and GX-D1.

In some embodiments, a PD-1 inhibitor can be pembrolizumab or nivolumab or IBI-308 or mDX-400 or BGB-108 or MEDI-0680 or SHR-1210 or PF-06801591 or PDR-001 or GB-226 or STI-1110. Nivolumab (also known as OPDIVO™, MDX-1106, BMS-936558, and ONO-4538) is a human IgG4 monoclonal antibody against PD-1. Pembrolizumab (also known as KEYTRUDA®, lambrolizumab, and MK-34) is a humanized IgG4 kappa isotype monoclonal antibody against PD-1. IBI-308 refers to a monoclonal antibody directed to PD-1. mDX-400 refers to a mouse antibody against PD-1. BGB-108 is a humanized monoclonal antibody against PD-1. MEDI-0680 (AMP-514) is a humanized IgG4 monoclonal antibody against PD-1. SHR-1210 refers to a monoclonal antibody against PD-1. PF-06801591 is a monoclonal antibody against PD-1. PDR-001 refers to a monoclonal antibody against PD-1. GB-226 refers to a monoclonal antibody against PD-1. STI-1110 refers to a monoclonal antibody against PD-1.

The anti-PD-1 antibodies and antibody fragments described herein encompass proteins having amino acid sequences that vary from those of the described antibodies, but that retain the ability to bind PD-1.

In some embodiments, the anti-PD-1 antibodies include bispecific antibodies and antibody-like therapeutic proteins including DARTs®, DUOBODIES®, BITES®, XmAbs®, TandAbs®, Fab derivatives, and the like that bind to PD-1.

The anti-PD-L1 antibodies and antibody fragments described herein encompass proteins having amino acid sequences that vary from those of the described antibodies, but that retain the ability to bind PD-L1. Such variant antibodies and fragments thereof can comprise one or more additions, deletions, or substitutions of amino acids when compared to the parent sequence, but exhibit biological activity that is essentially equivalent or essentially bioequivalent to that of the described antibodies.

In some embodiments, the anti-PD-L1 antibodies include bispecific antibodies and antibody-like therapeutic proteins including DARTs®, DUOBODIES®, BITES®, XmAbs®, TandAbs®, Fab derivatives, and the like that bind to PD-L1.

Non-limiting examples of additional PD-1/PD-L1 pathway inhibitors are described in, e.g., Chen and Han, *Jour Clin Invest,* 2015, 125(9):3384-3391, U.S. Pat. Nos. 8,168,757; 8,354,509; 8,552,154; 8,741,295; and 9,212,224; U.S. Patent App. Publ. Nos. 2014/0341917; 2015/0203580 and 2015/0320859; International Patent App. Publ. No. WO2015/026634.

A biological product, e.g., an antibody or a fragment thereof, is considered a biosimilar if, for example, the biological product is highly similar to an already FDA-approved biological product, known as the reference product. A biosimilar has no clinically meaningful differences in terms of safety and effectiveness from the reference product. A biosimilar can also have the same mechanism of action, route of administration, dosage form, and strength as its reference product.

Two biological products, e.g., antibodies or fragments thereof, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In some embodiments, two biological products (e.g., two antibodies or fragments thereof) are bioequivalent if there are no clinically meaningful differences in their safety, purity, or potency.

In other embodiments, two biological products (e.g., two antibodies or fragments thereof) are bioequivalent if a patient can be switched one or more times between the reference product and the biological product without an expected increase in the risk of adverse effects, including a clinically significant change in immunogenicity, or diminished effectiveness, as compared to continued therapy without such switching.

In yet other embodiments, two biological products (e.g., two antibodies or fragments thereof) are bioequivalent if they both act by a common mechanism of action for the condition of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Biobetter variants of the antibodies described herein may be based on an existing reference antibody specific for an target antigen, e.g., PD-1 or PD-L1, which has undergone changes such that, for example, it has a higher binding affinity to its target antigen and/or binds to a different epitope than the reference antibody, or has more desirable therapeutic efficacy, expression and/or biophysical characteristics.

C. Pharmaceutical Compositions

The pharmaceutical compositions provided herein, such as those including compounds for modulating CCR1 activity and agents for blocking the PD-1/PD-L1 pathway can contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

Biological products such as antibodies of the present invention may be constituted in a pharmaceutical composition containing one or antibodies or a fragment thereof and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). A pharmaceutical composition of the invention may include one or more pharmaceutically acceptable salts, anti-oxidant, aqueous and nonaqueous carriers, and/or adjuvants such as preservatives, wetting agents, emulsifying agents and dispersing agents.

The pharmaceutical compositions for the administration of the compounds and agents of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example, PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds and agents of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

The compounds and agents of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique. For instance, the compound and agent can be delivers to the tumor or the microenvironment surrounding the tumor.

In some embodiments, the compounds and agents may be deposited within a medical device, such as a stent, and delivered to the treatment site for treatment of a portion of the body. Stents have been used as delivery vehicles for therapeutic agents. Intravascular stents are generally permanently implanted in coronary or peripheral vessels. Stent designs include those of U.S. Pat. Nos. 4,733,655; 4,800,882; and 4,886,062. Such designs include both metal and polymeric stents, as well as self-expanding and balloon-expandable stents. Stents may also used to deliver therapeutic agents at the site of contact with the vasculature, as disclosed in U.S. Pat. No. 5,102,417 and International Patent Application Nos. WO 91/12779 and WO 90/13332, U.S. Pat. Nos. 5,419,760 and 5,429,634, for example.

The term "deposited" means that the compound and agent are coated, adsorbed, placed, or otherwise incorporated into the device by methods known in the art. For example, the compound and agent may be embedded and released from within ("matrix type") or surrounded by and released through ("reservoir type") polymer materials that coat or span the medical device. In the later example, the compound and agent may be entrapped within the polymer materials or coupled to the polymer materials using one or more the techniques for generating such materials known in the art. In other formulations, the compound and agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the compound and agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly(L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable popolymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

In some embodiments, the compound and agent are formulated for release from the polymer coating into the environment in which the medical device is placed. Preferably, the compound and agent are released in a controlled manner over an extended time frame (e.g., weeks or months) using at least one of several well-known techniques involving polymer carriers or layers to control elution. Some of these techniques were previously described in U.S. Patent App. Publ. No. 20040243225.

D. Methods of Treating Solid Tumor Cancers

In some aspects, the present invention provides methods of treating a solid tumor cancer in a subject in need thereof by administering to the subject having the cancer, a therapeutically effect amount of a CCR1 antagonist and a therapeutically effect amount of an inhibitor of PD-1 or an inhibitor of PD-L1. The subject can be administered a CCR1 antagonist and a PD-1 inhibitor. Alternatively, the subject can be administered a CCR1 antagonist and a PD-L1 inhibitor.

In some embodiments, the CCR1 antagonist and the PD-1 or PD-L1 inhibitor described herein may be used or combined with one or more additional therapeutic agents or therapeutic treatments (including but not limited to radiotherapy).

The "subject" is defined herein to include animals such as mammals, including, but not limited to, humans, other primates, cows, sheep, goats, horses, dogs, cats, rabbits, rats, mice and the like. The compounds, agents and compositions described herein are useful for treating a wide variety of cancers including solid tumor cancers.

The compositions, methods and kits described herein can be used to treat a subject diagnosed with a cancer or a tumor.

In some embodiments, the tumor can be a malignant or potentially malignant neoplasm or tissue mass of any size, and includes primary tumors and secondary neoplasms. A solid tumor can be an abnormal growth or mass of tissue that does not contain cysts or liquid areas.

In some embodiments, administering the compounds, agents and compositions of the present invention can decrease or reduce tumor burden, tumor load, tumor size, and/or the number of tumors in a subject. In some cases, the compounds, agents and compositions can prevent or minimize tumor metastasis. In other cases, the compounds, agents and compositions can promote or increase necrosis of the tumor.

In some embodiments, administering the compounds, agents and compositions of the present invention can lead to partial response or complete response (progression-free survival), delay progressive disease, and/or improve overall survival. In some cases, the compounds, agents and compositions can increase the durability of overall response to treatment, promote tumor regression, cancer regression, or disease stabilization, and/or provide a clinical benefit. In other cases, the compounds, agents and compositions can decrease the severity of at least one disease symptom, increase the frequency and duration of disease symptom-free periods, or prevent impairment or disability due to the cancer. In some instances, cancer development or cancer recurrence can be decreased.

A subject in need of the treatment may have a cancer or a solid tumor cancer including, but not limited to, adenocarcinoma, bladder cancer, breast cancer, triple negative breast cancer, colorectal cancer, colon cancer, liver cancer, lung cancer, non-small cell lung cancer, cancer of the small intestine, renal cancer, renal cell carcinoma, cancer of the esophagus, sarcoma, melanoma, multiple myeloma, bone cancer, pancreatic cancer, prostate cancer, stomach cancer, skin cancer, head and neck cancer, cutaneous or intraocular malignant melanoma, gastric cancer, bladder cancer, urothelial bladder cancer, uterine cancer, ovarian cancer, rectal cancer, cancer of the anal region, testicular cancer, uterine cancer, carcinoma of the fallopian tubes, carcinoma of the endometrium, carcinoma of the cervix, carcinoma of the vagina, carcinoma of the vulva, metastatic Merkel cell carcinoma, Hodgkin's lymphoma, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, carcinoma of the renal pelvis, neoplasm of the central nervous system (CNS), primary CNS lymphoma, glioblastoma, glioma, tumor angiogenesis, spinal axis tumor, brain stem glioma, pituitary adenoma, Kaposi's sarcoma, epidermoid cancer, squamous cell cancer, T-cell lymphoma, an environmentally induced cancer, any combination of said cancers, metastatic lesions of said cancers, an advanced cancer or malignancy, and an advanced solid tumor.

Additional examples of solid tumor cancers include, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, squamous cell carcinoma, basal cell carcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In some embodiments, the CCR1 antagonist and the PD-1 or PD-L1 inhibitor may be used or combined with one or more additional therapeutic agents or therapeutic treatments (including but not limited to chemotherapy, radiotherapy, and other treatments for cancer).

In some embodiments, the CCR1 antagonist and the PD-1 or PD-L1 inhibitor described herein may be used or combined with one or more of a chemotherapeutic agent, an anti-cancer agent, an anti-angiogenic agent, an antiproliferative/antimitotic agent, a poly(ADP-ribose) polymerase inhibitor, a DNA damaging agent including platinum drugs, an anti-fibrotic agent, an anti-hormonal agent, an immunotherapeutic agent, a therapeutic antibody, a bispecific antibody, an "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, a gene modifier or editor such as CRISPR (including CRISPR/Cas9), zinc finger nucleases or synthetic nucleases (TALENs), a CAR (chimeric antigen receptor) T-cell immunotherapeutic agent, or any combination thereof.

In some embodiments, these therapeutic agents are in the form of compounds, antibodies, polypeptides, or polynucleotides.

In some embodiments, the CCR1 antagonist and the PD-1 or PD-L1 inhibitor described herein are combined with one or more of an inhibitor, agonist, antagonist, ligand, modulator, stimulator, blocker, activator or suppressor of: Hedgehog protein, FGF receptor, Placenta growth factor, tyrosine kinase (including but not limited to Axl, MET, Abl, Bcr protein, EPH family, Fyn, Kit, Ltk, Lck, Src, Yes, Flt3, RET, Raf, Erbb, Erbb4, Erbb2, Jak, Jak1, Jak2, Btk, EGFR), DHFR, Epidermal growth factor, Cyclin-dependent kinase, Interferon beta, VEGF ligand, PDGF-B ligand, VEGF, CSF-1, Tubulin, mTOR, HDAC, PARP, Poly ADP ribose polymerase, Proteasome, Cyclooxygenase 2, GNRH, Estrogen receptor, Somatostatin receptor, Aromatase, Thymidylate synthase, Transferase, Cytotoxic T-lymphocyte protein-4, Macrophage mannose receptor 1, MEK-1 protein kinase, MEK-2 protein kinase, Thymidylate synthase, GCSF receptor, CSF2 gene, Retinoid X receptor, DNA polymerase, Topoisomerase II, Dihydropyrimidine dehydrogenase, Orotate phosphoribosyltransferase, DNA gyrase, Cytosine DNA methyltransferase, Topoisomerase I, Chorionic gonadotropin, Luteinizing hormone receptor, Interleukin-2 ligand, Interleukin-2, Estradiol 17 beta dehydrogenase, Glucocorticoid, Progesterone receptor, Dopamine D2 receptor, IL17 gene, Interleukin 17E, Neurokinin receptor, Retinoid X receptor, Ornithine decarboxylase, Interferon alpha 2, interleukin-2 ligand, interleukin-2, Albumin, microtubule, Cyclin G1 Thymidylate synthase, a checkpoint inhibitor, CTLA-4, 4-1BB (CD137), 4-1BBL (CD137L), B7-H3, B7-H4, BTLA, HVEM, TIM3, GAL9, LAG3, TIM3, B7H3, B7H4, VISTA, KIR, 2B4 CD160 (also referred to as BY55) CGEN-15049, OX40, or any combination thereof.

In some embodiments, the CCR1 antagonist and the PD-1 or PD-L1 inhibitor described herein may be used or combined with one or more of sonidegib, nintedanib, aflibercept, sorafenib, eribulin mesylate, pralatrexate, cetuximab, palbociclib, bevacizumab, recombinant interferon beta-1a, dasatinib, ramucirumab, pazopanib, trastuzumab emtansine, everolimus, sunitinib, perflubutane, zoledronic acid, ruxolitinib, ibrutinib, panobinostat, lapatinib, olaparib, bortezomib, celecoxib, gefitinib, goserelin acetate, raloxifene, octreotide acetate, octreotide, anastrozole, gemcitabine, letrozole, pemetrexed di sodium, cabozantinib, ipilimumab, technetium Tc 99m tilmanocept, cobimetinib, paclitaxel, pertuzumab, capecitabine, erlotinib, filgrastim, talimogene laherparepvec, trastuzumab, bazedoxifene, nimotuzumab, trabectedin, bexarotene, doxorubicin, docetaxel, CS-055, abiraterone, vorinostat, afatinib, leuprolide acetate, vandetanib, triptorelin pamoate, tegafur, gimeracil, oteracil potassium, pixantrone, carboplatin, exemestane, mitoxantrone, technetium Tc 99m tetrofosmin, ganirelix acetate, decitabine, irinotecan, bosutinib, epirubicin, apatinib, temsirolimus, choriogonadotropin alfa, vinorelbine, tamoxifen, triptorelin acetate, triptorelin, aldesleukin, mifepristone, vinflunine, gadobutrol, octafluoropropane, talaporfin, miltefosine, bromocriptine, DaunoXome, cetrorelix, pamidronate, Virulizin, DLBS-1425, 99mTc-sestamibi, arcitumomab, nafarelin, alitretinoin, formestane, trilostane, pirarubicin, eflornithine, histrelin, 111In-satumomab pendetide, interferon alpha-2b, interleukin-2, recombinant human interleukin-2, gadofosveset, Glutoxim, Rexin-G, doxifluridine, Prosorba, fadrozole, ipilimumab, tremelimumab, AGEN-1884, ADC-1015, PSI-001, JHL-1155 and lobaplatin, or any combination thereof.

In some embodiments, the CCR1 antagonist and either the PD-1 inhibitor or the PD-L1 inhibitor of the present invention can be administered in combination with other appropriate anti-cancer therapeutic agents, including, e.g., chemotherapeutic agents, radiation, biologics, immunotherapies, etc. Selection of the appropriate agents for use in combination therapy may be made by one of ordinary skill in the art, according to conventional pharmaceutical principles. The combination of therapeutic agents may act synergistically to effect the treatment or prevention of the various disorders such as, e.g., cancer. Using this approach, one may be able to achieve therapeutic efficacy with lower dosages of each agent, thus reducing the potential for adverse side effects.

In some embodiments, the CCR1 antagonist and the PD-1 or PD-L1 inhibitor described herein and one or more additional therapeutic agent are administered simultaneously, separately, or sequentially.

E. Methods of Administration

Depending on the cancer and the subject's condition or disease status, the compounds, agents, and compositions of the present invention may be administered by oral, parenteral (e.g., intramuscular, intraperitoneal, intravenous, ICV, intracistemal injection or infusion, subcutaneous injection, or implant), by implantation (e.g., as when the compound is coupled to a stent device), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment of cancers, e.g., solid tumors which require chemokine receptor modulation, an appropriate dosage level of a CCR1 antagonist will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

An appropriate dosage level of a PD-1 inhibitor or a PD-L1 inhibitor will generally be about 0.0001 to about 100 mg/kg, usually from about 0.001 to about 20 mg/kg, and more usually from about 0.01 to about 10 mg/kg, of the subject's body weight. Preferably, the dosage is within the range of 0.1-10 mg/kg body weight. For example, dosages can be 0.1, 0.3, 1, 3, 5 or 10 mg/kg body weight, and more preferably, 0.3, 1, 3, or 10 mg/kg body weight. The dosing schedule can typically be designed to achieve exposures that result in sustained receptor occupancy (RO) based on typical pharmacokinetic properties of an antibody. An exemplary treatment regime entails administration once per week, once every two weeks, once every three weeks, once every four weeks, once a month, once every 3 months or once every three to 6 months. The dosage and scheduling may change during a course of treatment. For example, a dosing schedule may comprise administering an antibody: (i) every two weeks in 6-week cycles; (ii) every four weeks for six dosages, then every three months; (iii) every three weeks; (iv) 3-10 mg/kg body weight once followed by 1 mg/kg body weight every 2-3 weeks. Considering that an IgG4 antibody typically has a half-life of 2-3 weeks, a preferred dosage regimen for an anti-PD-1 or anti-PD-L1 antibody comprises 0.3-10 mg/kg body weight, preferably 3-10 mg/kg body weight, more preferably 3 mg/kg body weight via intravenous administration, with the antibody being given every 14 days in up to 6-week or 12-week cycles until complete response or confirmed progressive disease.

In some embodiments, two or more antibodies with different binding specificities are administered simultaneously, in which case the dosage of each antibody administered falls within the ranges indicated. The antibody can be administered on multiple occasions. Intervals between single dosages can be, for example, weekly, every 2 weeks, every 3 weeks, monthly, every three months or yearly. Intervals can also be irregular as indicated by measuring blood levels of antibody to the target antigen in the patient. In some methods, dosage is adjusted to achieve a plasma antibody concentration of about 1-1000 mg/ml and in some methods about 25-300 mg/ml.

Alternatively, an antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions may be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition can be administered via one or more routes of administration using one or more of a variety of methods well known in the art. As will be appreciated by the skilled artisan, the route and/or mode of administration will vary depending upon the desired results.

The therapeutic compound and agent in the combination therapy disclosed herein may be administered either alone or in a pharmaceutical composition which comprises the therapeutic compound and agent and one or more pharmaceutically acceptable carriers, excipients and diluents.

In some embodiments, the therapeutic compound and agent are each provided in an amount that would be sub-therapeutic if provided alone or without the other. Those of skill in the art will appreciate that "combinations" can involve combinations in treatments (i.e., two or more drugs can be administered as a mixture, or at least concurrently or at least introduced into a subject at different times but such that both are in a subject at the same time).

Likewise, compounds, agents and compositions of the present invention may be used in combination with other drugs that are used in the treatment, prevention, suppression or amelioration of cancer. Such other drugs may be administered, by a route and in an amount commonly used therefor, contemporaneously or sequentially with a compound, agent or composition of the present invention. When a compound, agent or composition of the present invention is used contemporaneously with one or more other drugs, a pharmaceutical composition containing such other drugs in addition to the compound, agent or composition of the present invention is preferred. Accordingly, pharmaceutical compositions can include those that also contain one or more other active ingredients or therapeutic agents, in addition to a compound, agent or composition of the present invention.

The compounds, agents and compositions disclosed herein can be provided at a dosage level and frequency of dosage to provide a synergistic effect of the CCR1 antagonist in combination with the PD-1 inhibitor or the PD-L1 inhibitor.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Combination therapy includes co-administration of the CCR1 antagonist and the PD-1 or PD-L1 pathway inhibitor, sequential administration of the CCR1 antagonist and the PD-1 or PD-L1 pathway inhibitor, administration of a composition containing the CCR1 antagonist and the PD-1 or PD-L1 pathway inhibitor, or simultaneous administration of separate compositions such that one composition contains the CCR1 antagonist and another composition contains the PD-1 or the PD-L1 pathway inhibitor.

F. Kits

In some aspects, provided herein are kits containing a CCR1 chemokine receptor antagonist described herein and either a PD-1 inhibitor or a PD-L1 inhibitor described herein. Such kits are useful for treating a subject with a cancer such as a solid tumor cancer. The kit can contain a pharmaceutical composition containing a CCR1 chemokine receptor antagonist and a PD-1 inhibitor or a PD-L1 inhibitor. The kit can contain a pharmaceutical composition containing a CCR1 chemokine receptor antagonist and a PD-1 inhibitor. The kit can contain a pharmaceutical composition containing a CCR1 chemokine receptor antagonist and a PD-L1 inhibitor. The CCR1 chemokine receptor antagonist can be 1.001, 3.002, 4.005, 5.005, or 3.001, an analog thereof, or a derivative thereof.

In some embodiments, the CCR1 chemokine receptor antagonist is selected from the group consisting of BL-5923, UCB-35625, BX-471, BI-638683, PS-031291, MLN-3701, AZD-4818, MLN-3897, CP-481715, F-18-CCR1, AOP-RANTES, PS-375179, and NSC-651016. The PD-1 inhibitor can be pembrolizumab, nivolumab, IBI-308, mDX-400, BGB-108, MEDI-0680, SHR-1210, PF-06801591, PDR-001, GB-226, STI-1110, a biosimilar thereof, a biobetter thereof, or a bioequivalent thereof. The PD-1 inhibitor can be pembrolizumab, nivolumab, IBI-308, mDX-400, BGS-108, MEDI-0680, SHR-1210, PF-06801591, PDR-001, GB-226, or STI-1110. The PD-L1 inhibitor can be durvalumab, atezolizumab, avelumab, BMS-936559, ALN-PDL, TSR-042, KD-033, CA-170, STI-1014, KY-1003, a biosimilar thereof, a biobetter thereof, or a bioequivalent thereof. The PD-L1 inhibitor can be durvalumab, atezolizumab, avelumab, BMS-936559, ALN-PDL, TSR-042, KD-033, CA-170, STI-1014, or KY-1003. The PD-L1 inhibitor can be durvalumab, atezolizumab, avelumab, BMS-936559, ALN-PDL, TSR-042, KD-033, CA-170, CA-327, STI-1014, KY-1003, a biosimilar thereof, a biobetter thereof, or a bioequivalent thereof. The PD-L1 inhibitor can be durvalumab, atezolizumab, avelumab, BMS-936559, ALN-PDL, TSR-042, KD-033, CA-170, CA-327, STI-1014, or KY-1003.

In some embodiments, the PD-1 and/or PD-L1 inhibitor is selected from the compounds disclosed in WO14151634, WO15160641, WO16039749, WO16077518, WO16100608, WO16149351, WO2016057624, WO2016100285, US2016194307, US2016222060, US2015291549, US2016194307 and US2014294898 (BRISTOL MYERS SQUIBB CO) which are thereby incorporated by reference.

In some embodiments, the PD-1 or PD-L1 inhibitor is selected from the compounds disclosed in U.S. Provisional Patent Application Nos. 62/355,119 or 62/440,100 which are hereby incorporated by reference.

In some embodiments, the PD-1 and/or PD-L1 inhibitor is selected from the group consisting of:

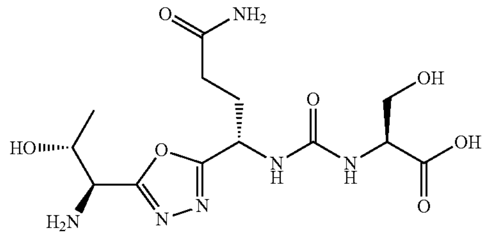

-continued

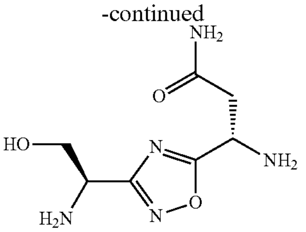

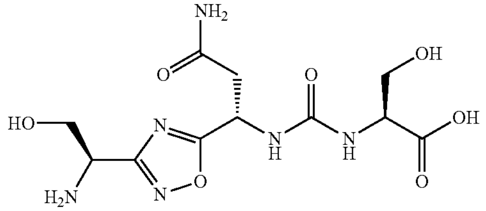

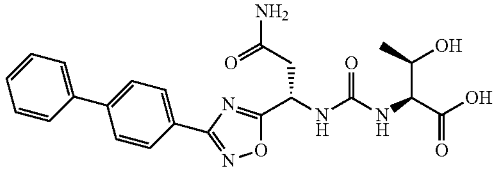

and

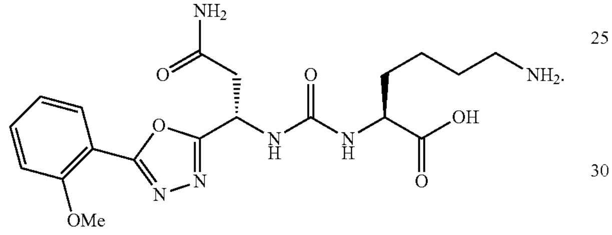

In some embodiments, the PD-1 anchor PD-L1 inhibitor is selected from the compounds disclosed in WO16142886, WO16142894, WO16142852, WO16142833, WO15033301, WO15033299, WO11161699, WO12168944, WO13132317, WO13144704, WO15033303, WO15036927, WO15044900, WO16142835, US2015073024, U.S. Pat. Nos. 8,907,053, 9,044,442, 9,096,642, 9,233,940, and US2016194295 (Aurigene discovery tech ltd) which are thereby incorporated by reference.

In some embodiments, the PD-1 and/or PD-L1 inhibitor is selected from the group consisting of durvalumab, atezolizumab, pembrolizumab, nivolumab, AP-106, AP-105, MSB-2311, CBT-501, avelumab, AK-105, IO-102, IO-103, PDR-001, CX-072, SHR-1316, JTX-4014, GNS-1480, recombinant humanized anti-PD1 mAb (Shanghai Junshi Biosciences), REGN-2810, pelareorep, SHR-1210, PD1/PDL1 inhibitor vaccine (THERAVECTYS), BGB-A317, recombinant humanized anti-PD-1 mAb (Bio-Thera Solutions), Probody targeting PD-1 (CytomX), XmAb-20717, FS-118, PSI-001, SN-PDL01, SN-PD07, PD-1 modified TILs (Sangamo Therapeutics), PRS-332, FPT-155, jienuo mAb (Genor Biopharma), TSR-042, REGN-1979, REGN-2810, resminostat, FAZ-053, PD-1/CTLA-4 bispecific antibody (MacroGenics), MGA-012, MGD-013, M-7824, PD-1 based bispecific antibody (Beijing Hanmi Pharmaceutical), AK-112, AK-106, AK-104, AK-103, BI-754091, ENUM-244C8, MCLA-145, MCLA-134, anti-PD1 oncolytic monoclonal antibody (Transgene SA), AGEN-2034, IBI-308, WBP-3155, JNJ-63723283, MEDI-0680, SSI-361, CBT-502, anti-PD-1 bispecific antibody, dual targeting anti-PD-1/LAG-3 mAbs (TESARO), dual targeting anti-PD-1/TIM-3 mAbs (TESARO), PF-06801591, LY-3300054, BCD-100, STI-1110, pembrolizumab biosimilar, nivolumab biosimilar, PD-L1-TGF-beta therapy, KY-1003, STI-1014, GLS-010, AM-0001, GX-P2, KD-033, PD-L1/BCMA bispecific antibody (Immune Pharmaceuticals), PD-1/Ox40 targeting bispecific antibody (Immune Pharmaceuticals), BMS-936559, anti-PD-1/VEGF-A DARPins (Molecular Partners), mDX-400, ALN-PDL, PD-1 inhibitor peptide (Aurigene), siRNA loaded dendritic cell vaccine (Alnylam Pharmaceuticals), GB-226, PD-L1 targeting CAR-TNK-based immunotherapy (TNK Therapeutics, NantKwest), INSIX RA, INDUS-903, AMP-224, anti-CTLA-4/anti-PD-1 bispecific humanized antibody (Akeso Biopharma), B7-H1 vaccine (State Key Laboratory of Cancer Biology/Fourth Military Medical University), and GX-D1.

In some instances, the kit includes written materials e.g., instructions for use of the compound, agent, antibody or pharmaceutical compositions thereof. Without limitation, the kit may include buffers, diluents, filters, needles, syringes, and package inserts with instructions for performing any methods disclosed herein.

G. Metastasis

In some embodiments, a method of decreasing or preventing metastasis in a subject having a solid tumor cancer, comprising administering to the subject in need thereof a therapeutically effective amount of a CCR1 chemokine receptor antagonist, is provided.

In some embodiments, the metastasis is lung metastasis.

In some embodiments, the CCR1 chemokine receptor antagonist has the formula (IIIb1a):

(IIIb1a)

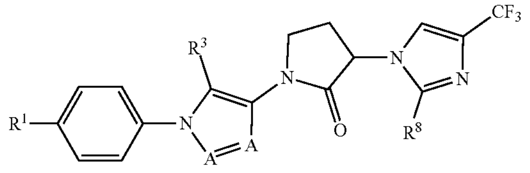

wherein each A is N or CH and at least one A is N; $R^1$ is halogen; $R^3$ is selected from the group consisting of $C_{1-8}$ alkyl, $C_{3-8}$ cycloalkyl and $C_{2-8}$ alkenyl; and $R^8$ is $C_{1-8}$ alkyl; or a pharmaceutically acceptable salt thereof.

In some embodiments, the CCR1 chemokine receptor antagonist is selected from the group consisting of:

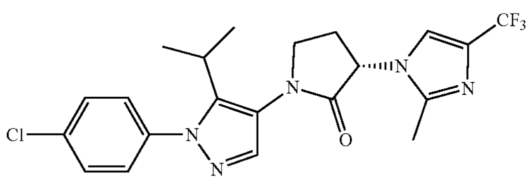

and

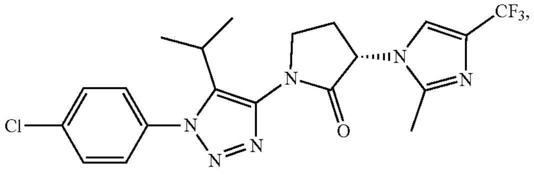

or a pharmaceutically acceptable salt thereof.

In some embodiments, the CCR1 chemokine receptor antagonist is selected from the group consisting of:

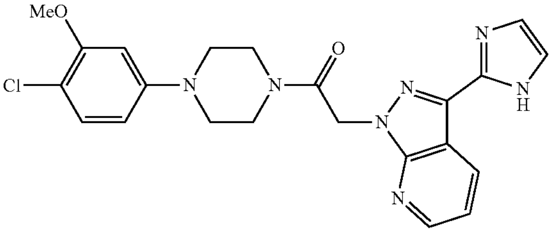
,
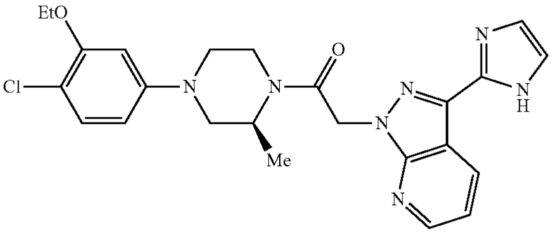
,
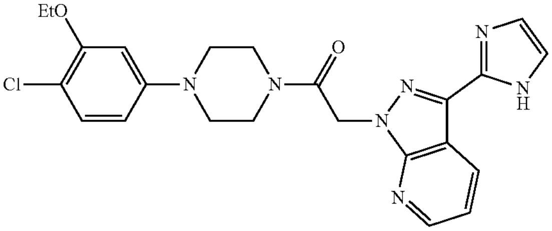
,
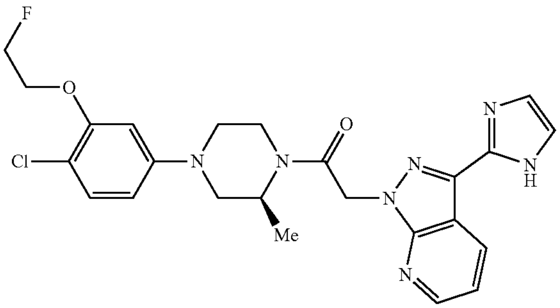
,
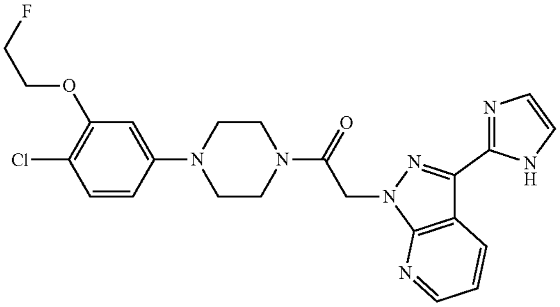
,
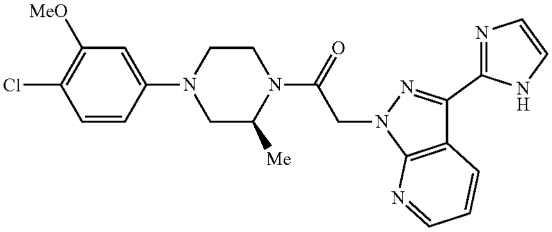
,
-continued
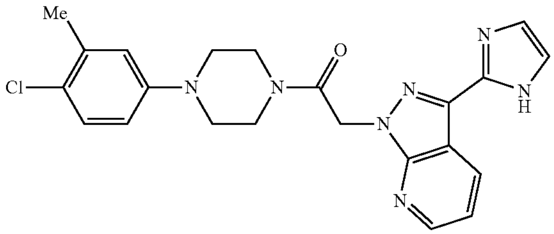
,
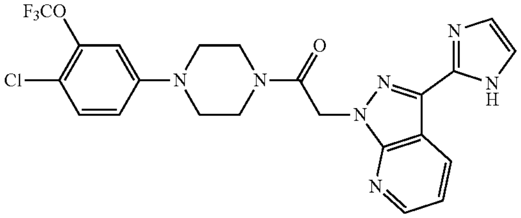
and
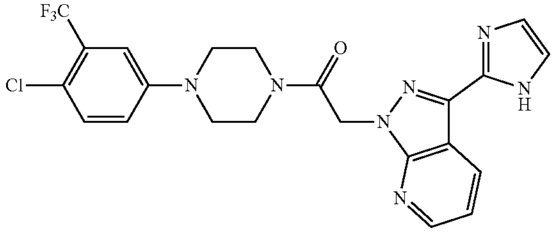
,
or a pharmaceutically acceptable salt thereof.
In some embodiments, the CCR1 chemokine receptor antagonist is selected from the group consisting of:
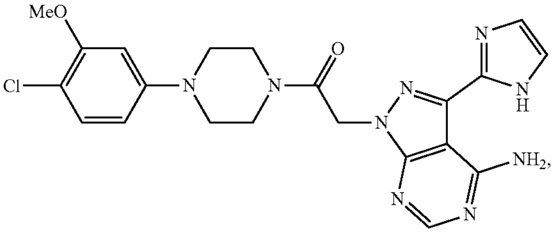
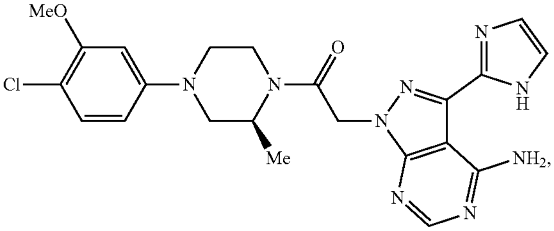
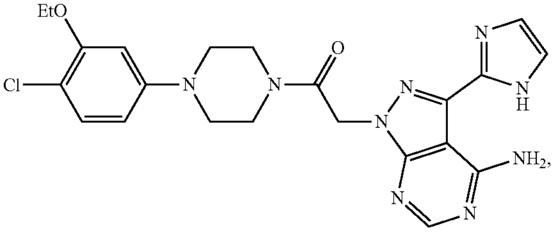

-continued

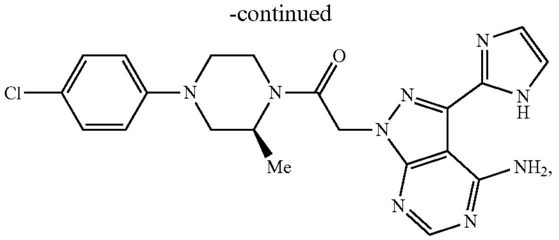

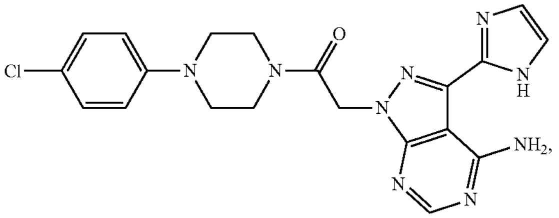

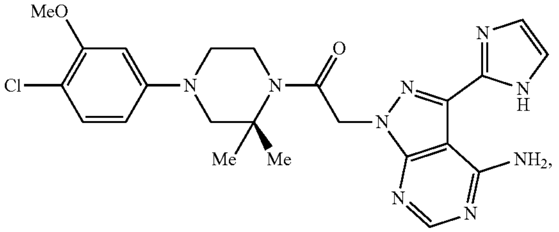

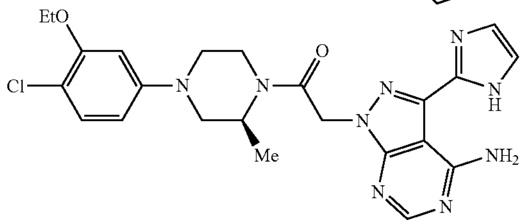

and

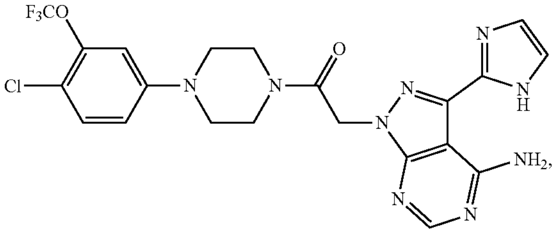

or a pharmaceutically acceptable salt thereof.

In some embodiments, the CCR1 chemokine receptor antagonist is selected from the group consisting of BL-5923, UCB-35625, BX-471, BI-638683, PS-031291, MLN-3701, AZD-4818, MLN-3897, CP-481715, F-18-CCR1, AOP-RANTES, PS-375179, and NSC-651016.

In some embodiments, the subject is a human subject.

In some embodiments, the solid tumor cancer is selected from the group consisting of brain cancer, breast cancer, triple negative breast cancer, bladder cancer, bone cancer, colorectal cancer, lung cancer, kidney cancer, liver cancer, stomach cancer, prostate cancer, sarcoma, melanoma, carcinoma, and lymphoma.

In some embodiments, the solid tumor cancer is triple negative breast cancer.

In some embodiments, the CCR1 antagonist is administered with one or more additional therapeutic agent.

In some embodiments, the one or more additional therapeutic agent is a a PD-1 inhibitor or a PD-L1 inhibitor.

In some embodiments, the PD-1 inhibitor is selected from the group consisting of pembrolizumab, nivolumab, IBI-308, mDX-400, BGB-108, MEDT-0680, SHR-1210, PF-06801591, PDR-001, GB-226, STI-1110, biosimilars thereof, biobetters thereof, and bioequivalents thereof.

In some embodiments, the PD-L1 inhibitor is selected from the group consisting of durvalumab, atezolizumab, avelumab, BMS-936559, ALN-PDL, TSR-042, KD-033, CA-170, CA-327, STI-1014, KY-1003, biosimilars thereof, biobetters thereof, and bioequivalents thereof.

In some embodiments, the PD-1 and/or PD-L1 inhibitor is selected from the compounds disclosed in WO14151634, WO15160641, WO16039749, WO16077518, WO16100608, WO16149351, WO2016057624, WO2016100285, US2016194307, US2016222060, and US2014294898 (BRISTOL MYERS SQUIBB CO) which are thereby incorporated by reference.

In some embodiments, the PD-1 or PD-L1 inhibitor is selected from the compounds disclosed in U.S. Provisional Patent Application Nos. 62/355,119 or 62/440,100 which are hereby incorporated by reference.

In some embodiments, the PD-1 and/or PD-L1 inhibitor is selected from the group consisting of:

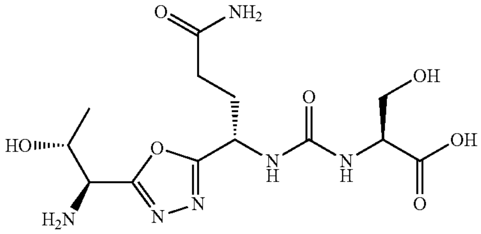

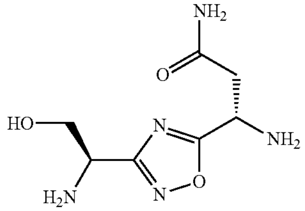

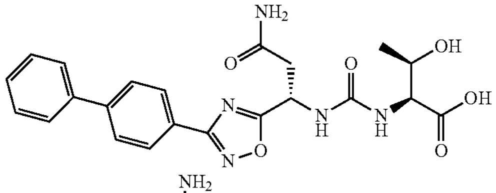

and

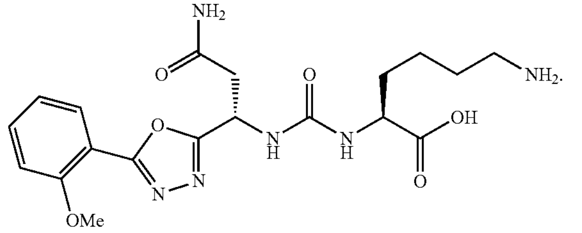

In some embodiments, the PD-1 anchor PD-L1 inhibitor is selected from the compounds disclosed in WO16142886, WO16142894, WO16142852, WO16142833, WO15033301, WO15033299, WO11161699, WO12168944, WO13132317, WO13144704, WO15033303, WO15036927, WO15044900, WO16142835, US2015073024, U.S. Pat. Nos. 8,907,053, 9,044,442, 9,096,642, 9,233,940, and US2016194295 (Aurigene discovery tech ltd) which are thereby incorporated by reference.

In some embodiments, the PD-1 and/or PD-L1 inhibitor is selected from the group consisting of durvalumab, atezolizumab, pembrolizumab, nivolumab, AP-106, AP-105, MSB-2311, CBT-501, avelumab, AK-105, IO-102, IO-103, PDR-001, CX-072, SHR-1316, JTX-4014, GNS-1480, recombinant humanized anti-PD1 mAb (Shanghai Junshi Biosciences), REGN-2810, pelareorep, SHR-1210, PD1/PDL1 inhibitor vaccine (THERAVECTYS), BGB-A317, recombinant humanized anti-PD-1 mAb (Bio-Thera Solutions), Probody targeting PD-1 (CytomX), XmAb-20717, FS-118, PSI-001, SN-PDL01, SN-PD07, PD-1 modified TILs (Sangamo Therapeutics), PRS-332, FPT-155, jienuo mAb (Genor Biopharma), TSR-042, REGN-1979, REGN-2810, resminostat, FAZ-053, PD-1/CTLA-4 bispecific antibody (MacroGenics), MGA-012, MGD-013, M-7824, PD-1 based bispecific antibody (Beijing Hanmi Pharmaceutical), AK-112, AK-106, AK-104, AK-103, BI-754091, ENUM-244C8, MCLA-145, MCLA-134, anti-PD1 oncolytic monoclonal antibody (Transgene SA), AGEN-2034, IBI-308, WBP-3155, JNJ-63723283, MEDT-0680, SSI-361, CBT-502, anti-PD-1 bispecific antibody, dual targeting anti-PD-1/LAG-3 mAbs (TESARO), dual targeting anti-PD-1/TIM-3 mAbs (TESARO), PF-06801591, LY-3300054, BCD-100, STI-1110, pembrolizumab biosimilar, nivolumab biosimilar, PD-L1-TGF-beta therapy, KY-1003, STI-1014, GLS-010, AM-0001, GX-P2, KD-033, PD-L1/BCMA bispecific antibody (Immune Pharmaceuticals), PD-1/Ox40 targeting bispecific antibody (Immune Pharmaceuticals), BMS-936559, anti-PD-1/VEGF-A DARPins (Molecular Partners), mDX-400, ALN-PDL, PD-1 inhibitor peptide (Aurigene), siRNA loaded dendritic cell vaccine (Alnylam Pharmaceuticals), GB-226, PD-L1 targeting CAR-TNK-based immunotherapy (TNK Therapeutics/NantKwest), INSIX RA, INDUS-903, AMP-224, anti-CTLA-4/anti-PD-1 bispecific humanized antibody (Akeso Biopharma), B7-H1 vaccine (State Key Laboratory of Cancer Biology/Fourth Military Medical University), and GX-D1.

IV. Examples

The following examples are offered to illustrate, but not to limit, the claimed invention.

The small molecule CCR1 antagonist used is Compound 3.002 and the anti-PD-L1 monoclonal antibody is BioLegend® 10F.9G2.

Example 1

Combination Therapy of Chemokine Receptor Inhibition Plus PD-L1

Blockade Potentiates Anti-Tumor Effects in Murine Model of Breast Cancer Trafficking and expansion of myeloid derived suppressor cells (MDSCs) play a major role in immune suppression of tumor. MDSCs express chemokine receptors which likely mediate their recruitment to the tumor microenvironment. Suppression of T cells is also mediated by the interaction of programmed death-1 (PD-1) and its ligands which are abundantly expressed in cancer cells and immune infiltrates, including MDSCs.

Breast cancer is one of the leading causes of cancer related death. There were estimated 231,840 new cases in 2015. Targeted therapies are successful for some subtypes of breast cancer, for example, trastuzumab (Herceptin®) for HER2+ subtype, and hormonal therapy for estrogen receptor (ER)+ or progesterone receptor (PR)+ subtypes. Unfortunately, there are no effective targeted therapies for triple negative breast cancer (TNBC; HER2-ER-PR-). TNBC is more immunogenic than other types. Triple negative breast cancer is highly mutagenic and produces neoantigens that can induce an immune response. Immune-modulating therapy may be effective for treating this and similar cancers.

This example shows that targeting both pathways through administration of a small molecule chemokine receptor antagonist (Compound 3.002 which blocks CCR1) and an anti-PD-L1 monoclonal antibody (BioLegend® 10F.9G2) significantly reduced tumor burden in an orthotopic breast cancer mouse model.

Analysis of human breast cancer patient samples from The Cancer Genome Atlas (TCGA) database revealed that the CCR1 ligands, MCP-7 (CCL7) and RANTES (CCL5) are present at significantly higher levels in breast cancers as compared to normal breast tissue. Furthermore, CCR1 and its ligands, as well as PD-L1 are significantly higher in triple negative breast cancer samples than in the other breast cancer subtypes.

Figure 1B:
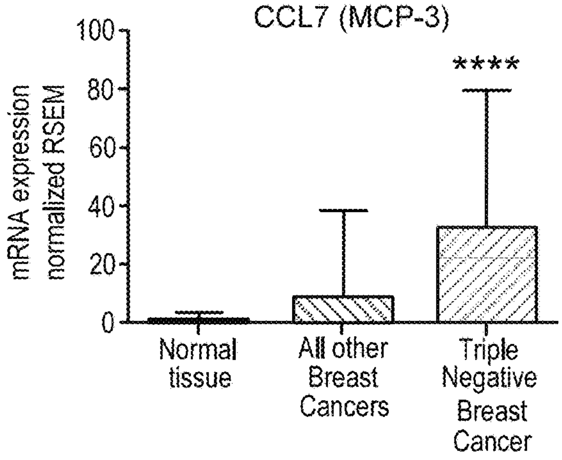
Figure 1C:
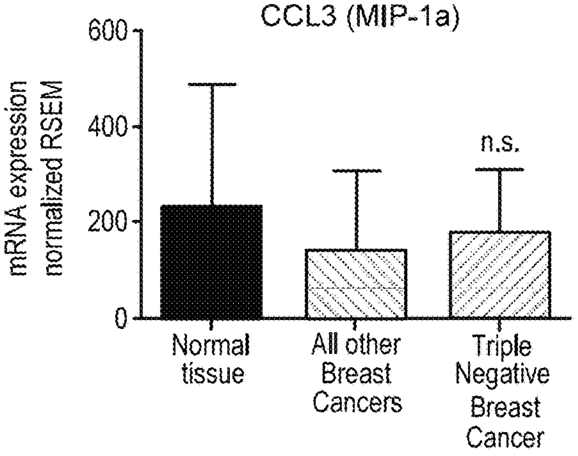
Figure 1D:
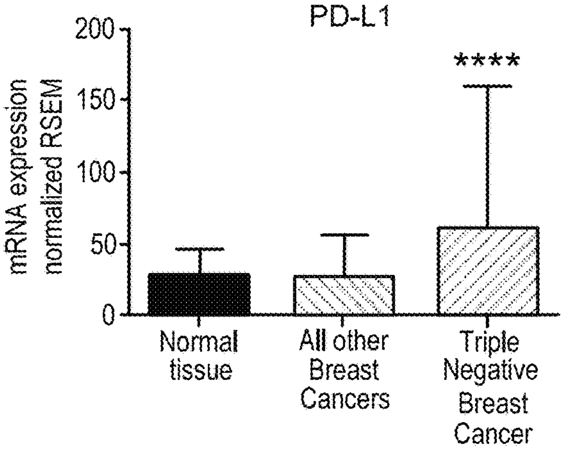

Higher expression levels of the chemokine receptor CCR1 ligands—CCL5 (RANTES; FIG. 1A) and CCL7 (MCP-3; FIG. 1B), as well as the PD-1 ligand (PD-L1; FIG. 1D) were detected in tissue samples from human patients with triple negative breast cancer compared to samples of normal tissue and tissue sample from all other types of breast cancers. The elevated expression was statistically significant. mRNA expression of the CCR1 ligand CCL3 (MIP-1$\alpha$; FIG. 1C) was not elevated in the breast cancer samples, e.g., triple negative breast cancer samples.

Figure 1E:
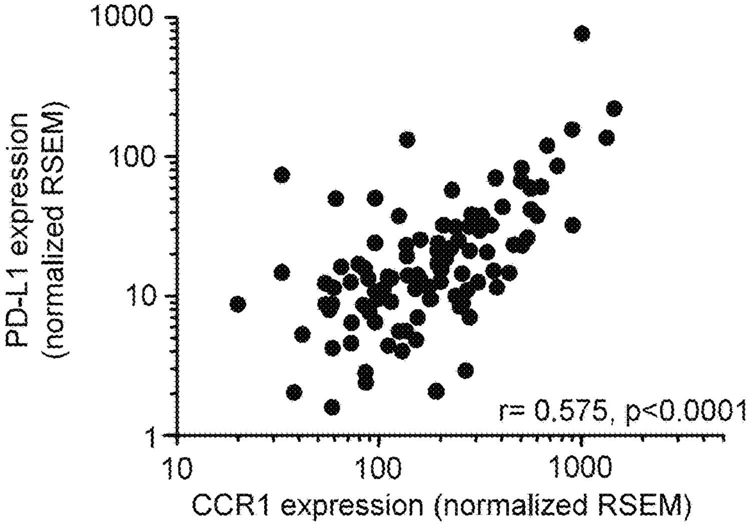
Figure 2:
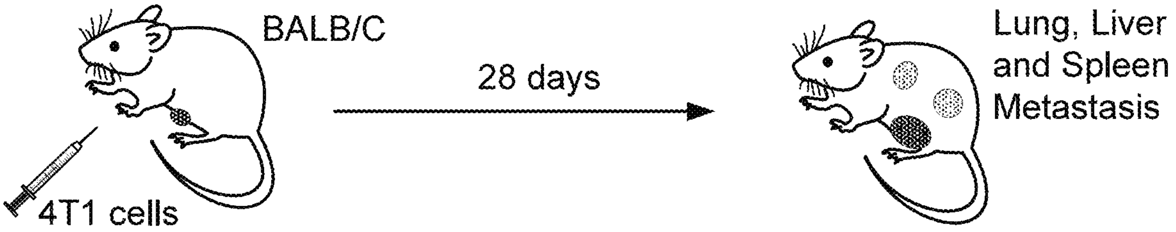
FIG. 2 depicts the 4T1 mammary carcinoma mouse model which can be used as a murine triple negative breast cancer model.

The expression of CCR1 and PD-L1 were well correlated in human breast cancer patient samples (FIG. 1E). Each dot of the graph represents a breast tumor sample from an individual patient with breast cancer. In FIG. 1E, "r" represents the Pearson correlation coefficient.

In this study, a murine triple negative breast cancer model (the 4T1 mammary carcinoma mouse model) was used to investigate the therapeutic effect of CCR1 blockage in combination with PD-L1 monoclonal antibody.

$5\times10^4$ 4T1 breast cancer cells were orthotopically injected into the mammary gland of 6-8 week female BALB/C mice. 13 days post-implantation, the mice were randomized based on the tumor volume, so that each group had similar average volume around 150 $mm^3$. The tumor volumes were measured by caliper measurement and calculated by width$\times$(length)$^2$/2. On day 13 post-implantation, CCR1 antagonist 3.002 was dosed for the following 10 days, at 15 mg/kg through oral gavage, twice a day. Anti-PD-L1 monoclonal antibody (BioLegend, 10F.9G2) was dosed on day 13, 17 and 20 intraperitoneally, 200 μg per mouse. The same volume of vehicle (PEG400) and the same amount of isotype control antibody (Rat IgG, BioLegend) were dosed in the mice of the vehicle group. The tumor volumes were measured three times a week until day 23 post-implantation (FIGS. 3A-3D). Mice receiving the combined treatment exhibited reduced tumor progression (FIG. 3D) compared to mice receiving CCR1 antagonist alone (FIG. 3B), mice receiving PD-L1 mAb (FIG. 3C), and mice receiving vehicle (FIG. 3A).

On day 23 post-implantation, mice were sacrificed and tumors and lungs were harvested. The gross wet weights of tumors were measured. FIG. 3E shows that mice administered a therapy include a CCR1 antagonist in conjunction with an anti-PD-L1 monoclonal antibody had the lowest tumor weights.

Primary Tumor growth was not significantly changed by either agent alone (FIGS. 3B and 3C), but the combination of CCR1 inhibitor plus anti-PD-L1 antibody (FIG. 3D)

resulted in significantly reduced tumor burden. Tumor weight was significantly reduced in mice receiving combination therapy (FIG. 3E).

Figure 4A:
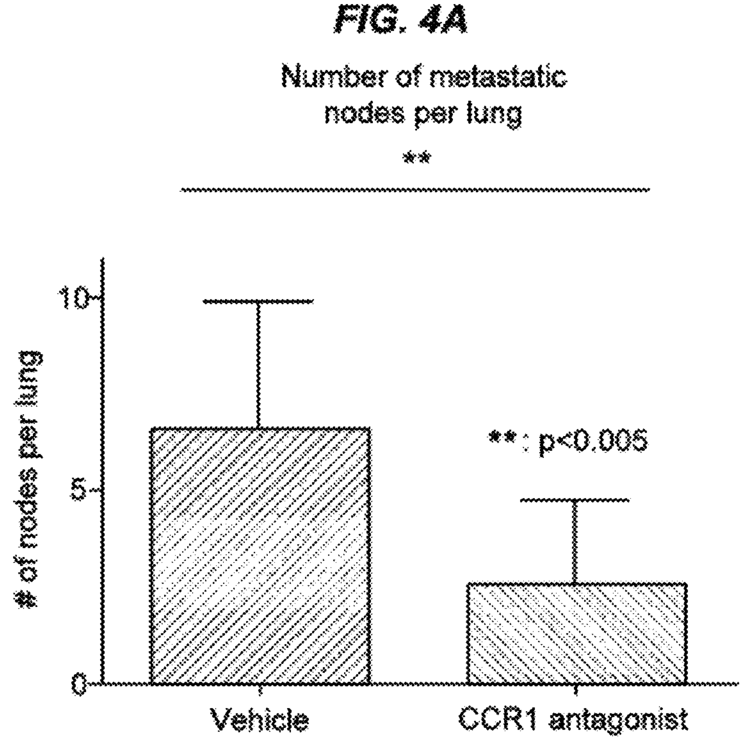
FIGS. 4A and 4B show that the CCR1 antagonist decreased lung metastasis in 4T1 tumor bearing mice.
Figure 4B:
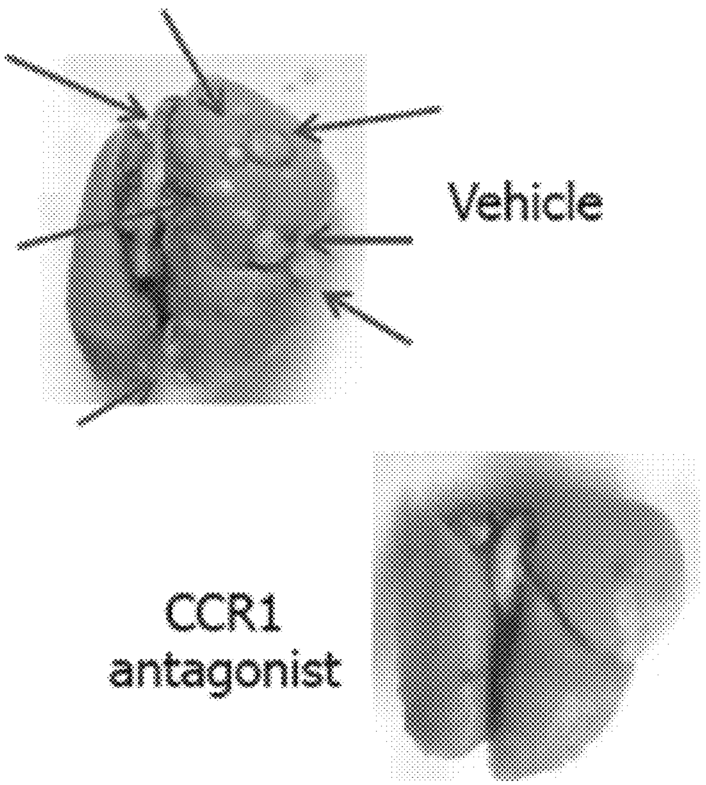

Lungs were fixed with Bouin's solution overnight and the numbers of surface metastasis nodes were counted by naked eye. (FIG. 4A). Student t-test was performed for the statistical analysis. *; $p<0.05$, ; $p<0.005$, ; $p<0.0001$. Mice administered CCR1 antagonist alone had fewer metastatic nodes per lung compared to mice treated with vehicle (FIG. 4**B).

Lung metastasis decreased statistically upon administration of the CCR1 antagonist alone to the 4T1 mouse model. FIG. 4A shows that the number of metastatic nodes per lung was reduced in mice receiving CCR1 antagonist treatment compared to vehicle.

Myeloid derived suppressor cells (MDSCs) rapidly expand during inflammation, infection, and cancer, and inhibit immune responses. MDSCs are strongly implicated in suppressing tumor-induced immune response. There are two major types of MDSCs, as shown in Table 1.

TABLE 1

| | Granulocytic-MDSC (G-MD SC) | Monocytic-MDSC (M-MDSC) |
|---|---|---|
| Mouse cell surface marker | $CD11b^{pos}Ly6G^{high}Ly6C^{low}$ | $CD11b^{pos}Ly6G^{neg}Ly6C^{high}$ |
| Human cell surface marker | $CD11b^{pos}CD15^{pos}CD14^{neg}$ | $CD11b^{pos}CD14^{pos}HLA\text{-}DR^{low}$ |
| Origin | Granulocytic immature myeloid cells | Monocytic immature myeloid cells |
| Chemokine receptors previously reported | G-MDSCs are CXCR2+ and some are CCR1+ | M-MDSCs are CCR2+ |

Figure 5A:
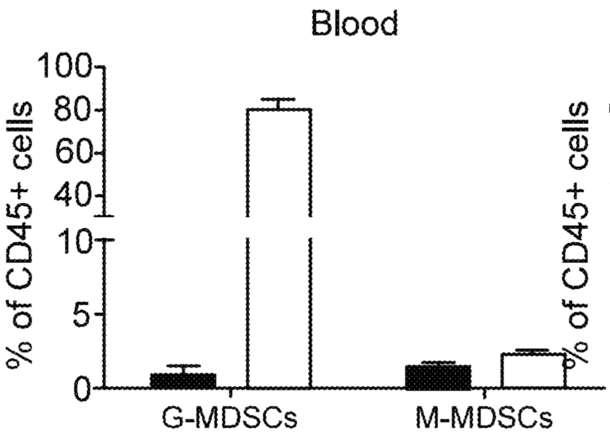
FIGS. 5A-5C show that granulocytic myeloid derived suppressor cells (G-MDSCs) are present in 4T1 tumor bearing mice. G-MDSCs are dramatically increased in blood (FIG. 5A) and the spleen (FIG. 5B) of these mice. Slight increases of monocytic myeloid derived suppressor cells (M-MDSCs) were also seen in blood and the spleen. The majority of the immune cells infiltrating the 4T1 tumors are G-MDSCs (FIG. 5C).
Figure 5B:
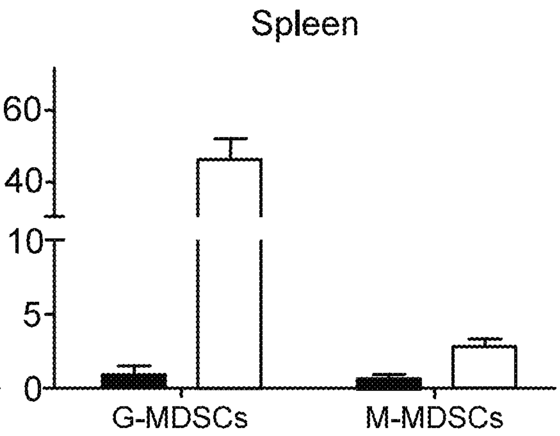
Figure 5C:
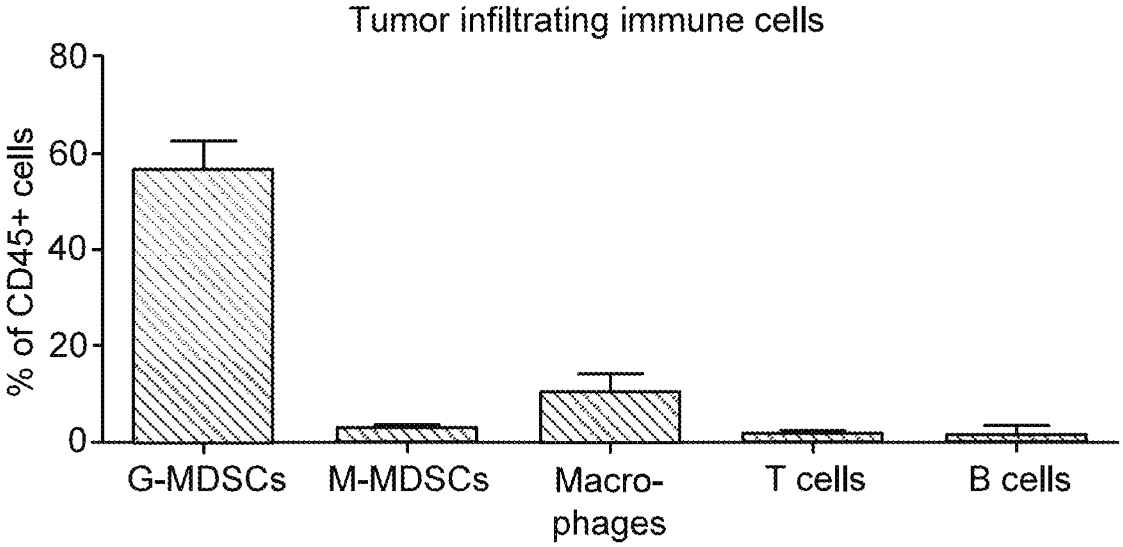
Figure 6A:
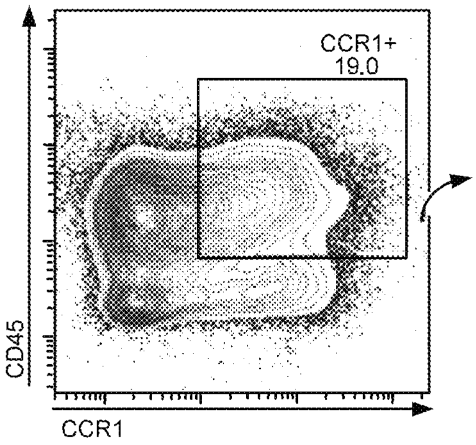
FIGS. 6A and 6B show that the majority of CCR1 expressing cells in the spleen of 4T1 tumor bearing mice are G-MDSCs. Flow cytometry analysis is provided in FIG. 6A.
Figure 6B:
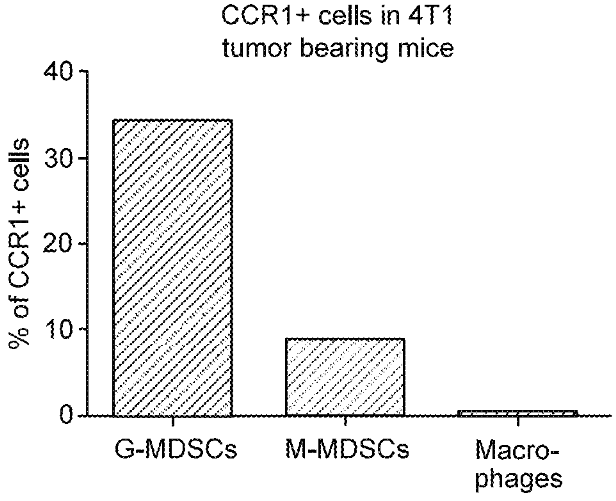
Figure 7A:
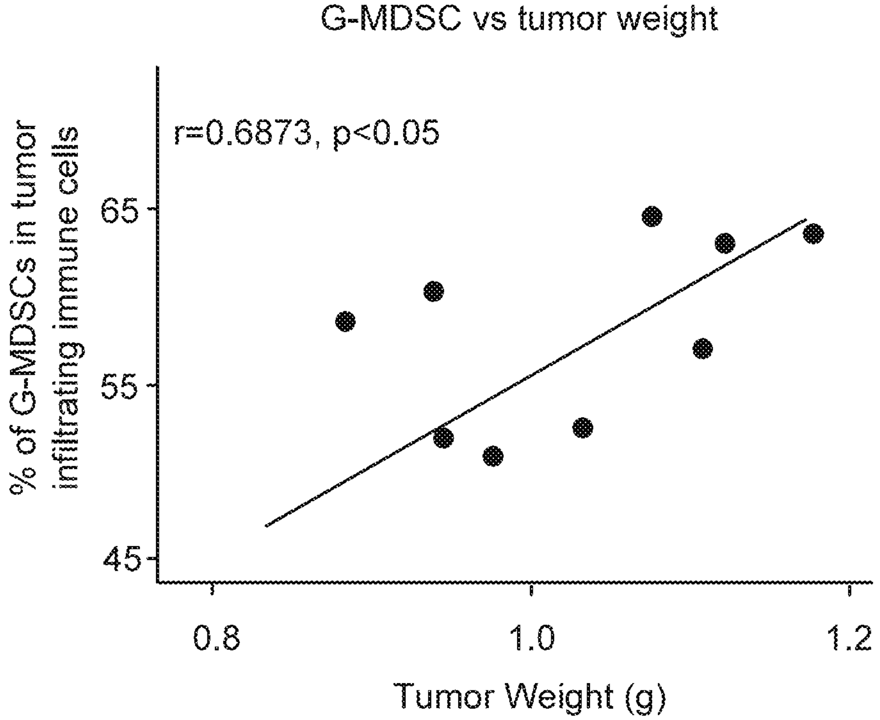
FIGS. 7A and 7B illustrate a correlation between tumor weight and the proportion of G-MDSCs and CD8-positive T cells.
Figure 7B:
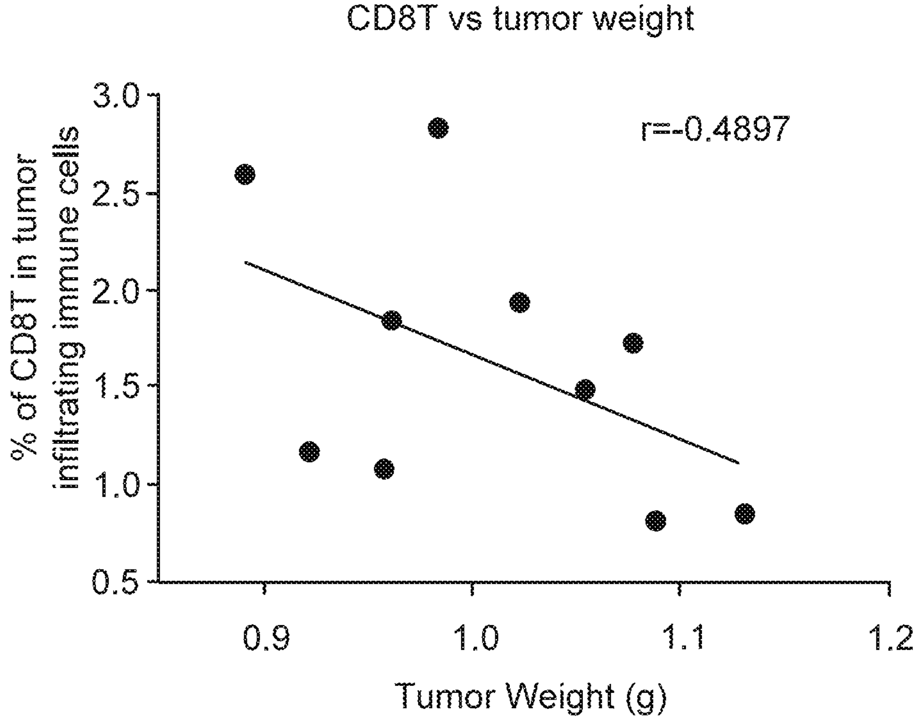

Orthotropic breast cancer cell engraftment induced robust expansion of $CD11b^{pos}Ly6G^{hi}Ly6C^{hi}$ MDSCs or G-MDSCs, a subpopulation of which express CCR1. FIG. 5A shows a dramatic increase in G-MDSCs in blood (FIG. 5A) and the spleen (FIG. 5B) of 4T1 tumor bearing mice. The majority of immune cells that infiltrate 4T1 tumors were G-MDSCs (FIG. 5C). Also, the majority of CCR1-expressing cells in the spleen of 4T1 tumor mice were G-MDSCs. FACS analysis as depicted in FIG. 6A shows a population $CD45^{pos}$ and $CCR1^{pos}$ cells from the spleen. This population was further analyzed to determine the percentage of G-MDSCs ($CD11b^{pos}Ly6G^{high}Ly6\ C^{high}$), M-MDSCs ($CD11b^{pos}Ly6^{neg}Ly6C^{high}$), and macrophages ($CD11b^{pos}Ly6G^{neg}Ly6C^{neg}F4/80^{pos}$) in these cells. The analysis also revealed that tumors with more C-MDSCs and less T cell infiltration were larger. For instance, FIG. 7A shows that tumor weight correlated with an increasing proportion of G-MDSCs in the tumor infiltrating immune cells. FIG. 7B shows that tumor weight also correlated with a reduced percentage of CD8+ T cell in the tumor infiltrating immune cells.

Figure 8A:
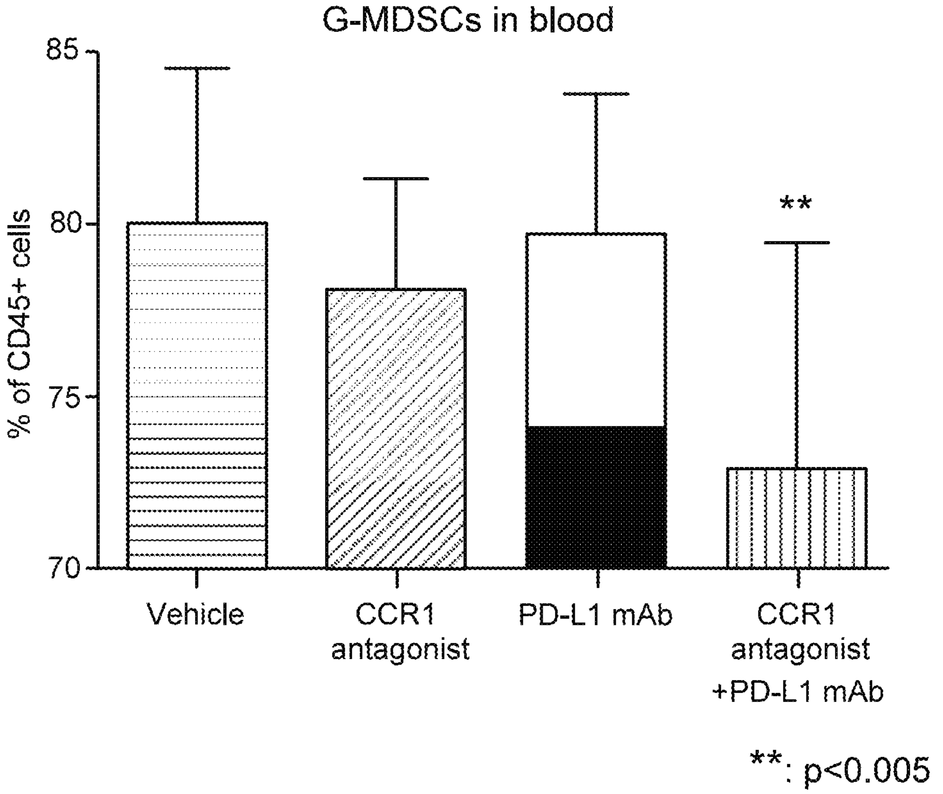
FIGS. 8A and 8B show that the combination therapy of a CCR1 antagonist and PD-L1 mAb decreases G-MDSC levels (FIG. 8A), but not M-MDSC levels (FIG. 8B) in blood of 4T1 tumor bearing mice.
Figure 8B:
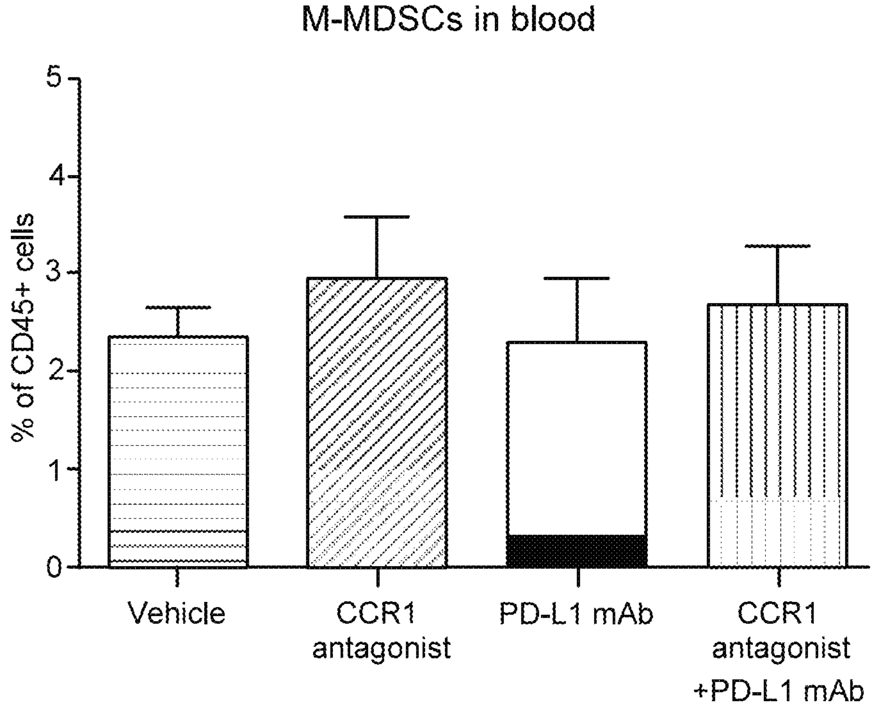

The number or percentage of G-MDSCs in the tumor infiltrating cells of the blood of 4T1 tumor mice was dramatically decreased after the mice were treated with a combination therapy of a small molecule CCR1 antagonist (3.002) and a PD-L1 mAb (FIG. 8A). The combination therapy did not affect the number or percentage of M-MDSCs in the blood (FIG. 8B).

Figure 9A:
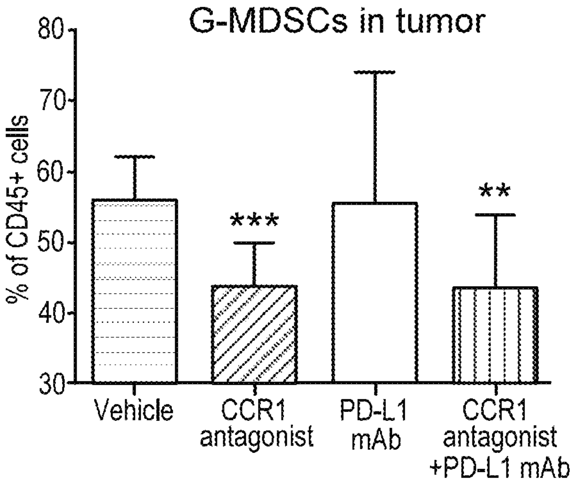
FIGS. 9A-9D show the levels of G-MDSCs, M-MDSCs, CD8 T cells, and B cells infiltrating 4T1 tumors following administration of vehicle, CCR1 antagonist, PD-L1 mAb, and combination therapy.
Figure 9B:
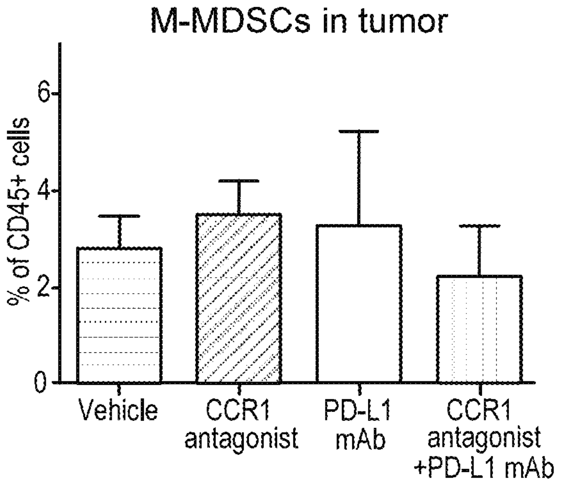
Figure 9C:
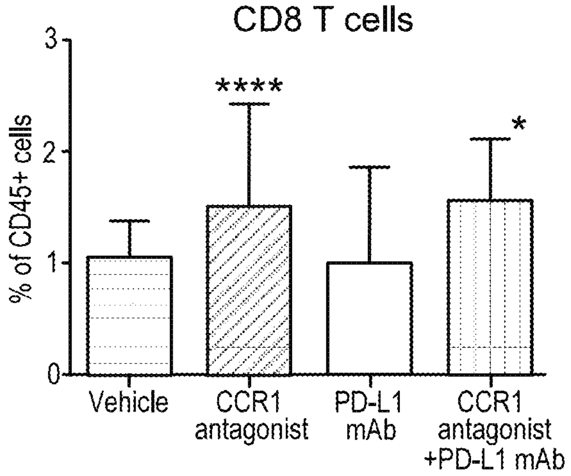
Figure 9D:
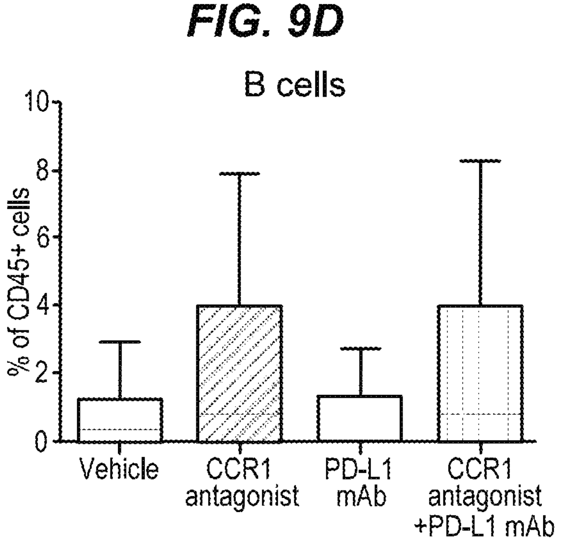

Analysis of the tumor infiltrating cells revealed that 3.002 alone or in combination with a PD-L1 mAb significantly reduced the number of G-MDSCs in the primary tumors (FIG. 9A). The results show that CCR1 blockade of G-MDSC trafficking translates into reduced tumor burden. The treatment regimens did not change the number or percentage of M-MDSCs in the primary tumors (FIG. 9B). Treatment with the CCR1 antagonist alone or in combination with a PD-L1 mAb significantly increased the percentage of CD8+ T cells (FIG. 9C). In some 4T1 tumors, 3.002 alone or in combination with a PD-L1 mAb also increased B cell infiltration.

Figure 10:
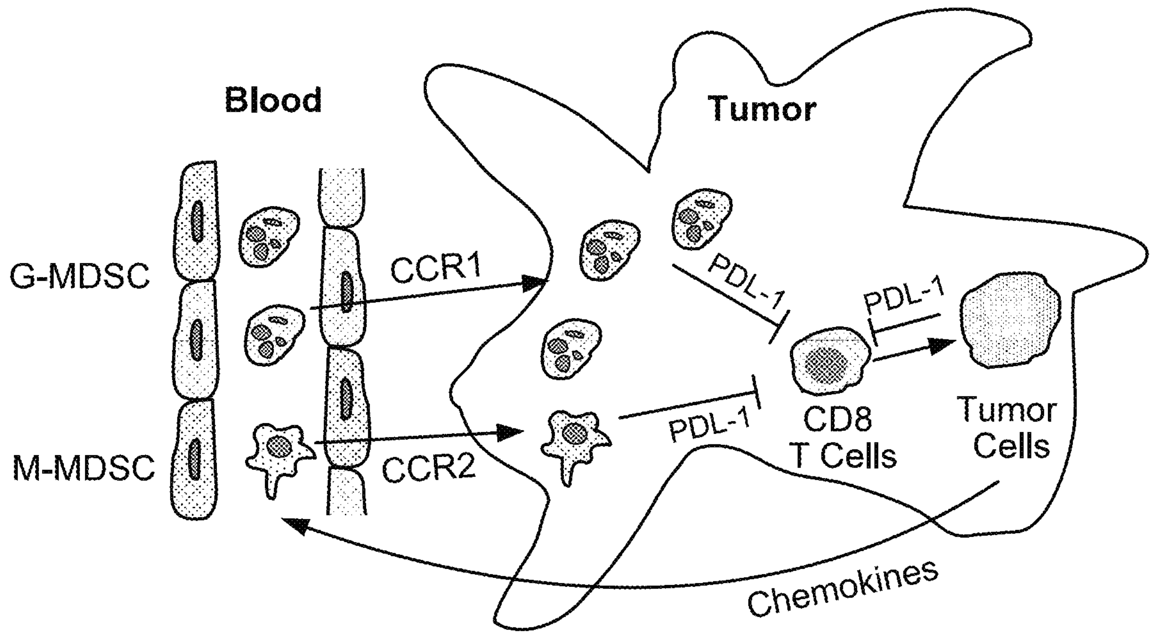
FIG. 10 depicts a schematic diagram of CCR1-mediated G-MDSC recruitment to a tumor microenvironment.

In summary, the data shows that CCR1 mediates G-MDSC recruitment to the tumor or the tumor microenvironment, and promotes tumor progression (FIG. 10). CCR1 receptor ligands and PD-L1 expression are significantly elevated in human breast cancer tumors, and particularly in triple negative breast cancers. G-MDSCs are increased in mice bearing 4T1 triple negative breast tumors and are positively correlated with larger tumors. Administration of the small molecule CCR1 antagonist, 3.002, in combination with a PD-L1 mAb significantly reduces primary tumor progression. Administration of the small molecule CCR1 antagonist, 3.002 significantly reduces lung metastasis. Also, the CCR1 antagonist and PD-L1 mAb decrease circulating and tumor infiltrating G-MDSCs and increase CD8 T cell and B cell infiltration in 4T1 triple negative tumors. This combination therapy potentiates the anti-tumor immune response. Thus, combination therapy that includes a CCR1 antagonist and a PD-L1 mAb may have therapeutic efficacy in treating human patients with triple negative breast cancer.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for treating a subject having a solid tumor expressing PD-1, said method comprising administering to the subject in need thereof a therapeutically effective amount of a CCR1 chemokine receptor antagonist, and a therapeutically effective amount of a PD-1 inhibitor, wherein the CCR1 chemokine receptor antagonist has the formula (IIIb1a):

(IIIb1a)

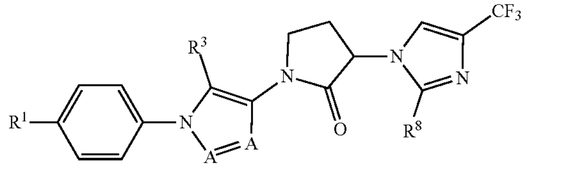

wherein each A is N or CH and at least one A is N; $R^1$ is halogen; $R^3$ is selected from the group consisting of $C_{1-8}$ alkyl, $C_{3-8}$ cycloalkyl and $C_{2-8}$ alkenyl; and $R^8$ is $C_{1-8}$ alkyl; or a pharmaceutically acceptable salt thereof, and wherein the solid tumor is triple negative breast cancer.

2. The method of claim 1, wherein the CCR1 chemokine receptor antagonist is selected from the group consisting of:

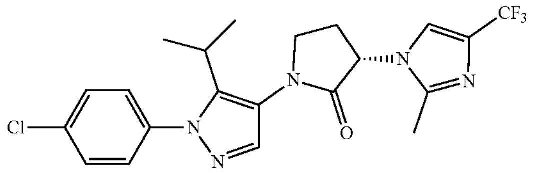

and

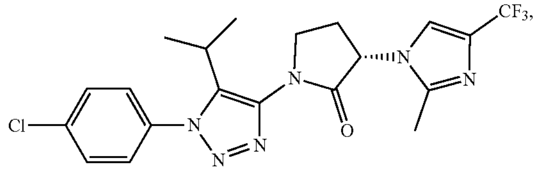

or a pharmaceutically acceptable salt thereof.

3. The method of claim 1, wherein the PD-1 inhibitor is selected from the group consisting of pembrolizumab, nivolumab, IBI-308, mDX-400, BGB-108, MEDI-0680, SHR-1210, PF-06801591, PDR-001, GB-226, and STI-1110.

4. The method of claim 1, wherein the CCR1 chemokine receptor antagonist and the PD-1 inhibitor are administered concomitantly.

5. The method of claim 4, wherein the CCR1 chemokine receptor antagonist and the PD-1 inhibitor are administered in a combination formulation.

6. The method of claim 1, wherein the CCR1 chemokine receptor antagonist and the PD-1 inhibitor are administered sequentially.

7. The method of claim 6, wherein the CCR1 chemokine receptor antagonist is administered prior to administration of the PD-1 inhibitor.

8. The method of claim 6, wherein the CCR1 chemokine receptor antagonist is administered after the administration of the PD-1 inhibitor.

9. The method of claim 1, wherein the CCR1 chemokine receptor antagonist is administered orally and the PD-1 inhibitor is administered intravenously.

10. The method of claim 1, wherein the subject is a human subject.

* * * * *